US008507239B2

(12) United States Patent
Lubys et al.

(10) Patent No.: US 8,507,239 B2
(45) Date of Patent: Aug. 13, 2013

(54) RESTRICTION ENDONUCLEASES AND THEIR APPLICATIONS

(75) Inventors: Arvydas Lubys, Vilnius (LT); Jolanta Vitkute, Vilnius (LT); Judita Lubiene, Vilnius (LT); Arvydas Janulaitis, Vilnius (LT)

(73) Assignee: Fermentas UAB, Vilnius (LT)

( * ) Notice: Subject to any disclaimer, the term of this patent is extended or adjusted under 35 U.S.C. 154(b) by 125 days.

(21) Appl. No.: 13/032,849

(22) Filed: Feb. 23, 2011

(65) Prior Publication Data

US 2011/0207139 A1 Aug. 25, 2011

(30) Foreign Application Priority Data

Feb. 23, 2010 (GB) .................................. 1003036.9

(51) Int. Cl.
*C12N 9/16* (2006.01)
(52) U.S. Cl.
USPC ........................................................ 435/196
(58) Field of Classification Search
USPC ........................................................ 435/196
See application file for complete search history.

(56) References Cited

U.S. PATENT DOCUMENTS

| 5,789,166 | A | 8/1998 | Bauer et al. |
| 2005/0153316 | A1 | 7/2005 | Jeddeloh et al. |
| 2005/0158739 | A1 | 7/2005 | Jeddeloh et al. |
| 2005/0272065 | A1 | 12/2005 | Lakey et al. |
| 2006/0228786 | A1 | 10/2006 | Salerno |
| 2006/0275806 | A1 | 12/2006 | Schwartz et al. |
| 2009/0004646 | A1 | 1/2009 | Schuster et al. |
| 2010/0167942 | A1* | 7/2010 | Zheng et al. ..................... 506/8 |

FOREIGN PATENT DOCUMENTS

| RU | 2270859 | 2/2006 |
| WO | 2005/040399 | 5/2005 |
| WO | 2010075375 | 7/2010 |

OTHER PUBLICATIONS

Pingoud et al., Cell. Mol. Life Sci. 62: 685-707 (2005).*
Zheng et al., Nucl. Acids Res. 38(16): 5527-5534 (2010).*
Partial European Search Report of EP 11155622, dated Jul. 27, 2011 and mailed Aug. 17, 2011.
Document No. XP-002653522 from Partial European Search Report of EP 11155622, Database UniProt A3PUQ5, Apr. 3, 2007.
Document No. XP-002653523 from Partial European Search Report of EP 11155622, SgeI product data from Fermentas website, Mar. 16, 2010.
DpnI product data New England Biolabs, Dec. 22, 2008, available at http://www.neb.com/nebecomm/products/faqproductR0176.asp.
SibEnzyme® product data, Jan. 15, 2010, available at www.sibenzyme.com/products.
Altschul SF et al., "Basic Local Alignment Search Tool," J. Mol. Biol., vol. 215 (1990), pp. 403-410.
Arber,W., "Genetic Variation: molecular mechanisms and impact on microbial evolution," FEMS Microbiol. Rev., vol. 24 (2000), pp. 1-7.
Barras,F and Marinus, MG, "The Great GATC: DNA methylation in *E. coli*," Trends Genet. vol. 5, No. 5, (1989), pp. 139-143.

(Continued)

*Primary Examiner* — Patricia A Leith
*Assistant Examiner* — Erin M Bowers
(74) *Attorney, Agent, or Firm* — Thompson Hine LLP

(57) ABSTRACT

Provided is a methylation-specific restriction endonuclease for a DNA duplex substrate, which endonuclease recognizes in a strand of the duplex a 2 to 6 nucleotide recognition sequence comprising a 5-methylcytosine, and cleaves each strand of the duplex at a fixed position outside the recognition sequence.

40 Claims, 19 Drawing Sheets

(56) References Cited

OTHER PUBLICATIONS

Beletskaya IV et al., DNA methylation at the CfrBI site is involved in expression control in the CfrBI restriction-modification system, Nucl. Acids Res. vol. 28, No. 19 (2000), pp. 3817-3822.
Bichet A, et al., "The "Bringer" strategy: a very fast and highly efficient method for construction of mutant libraries by error-prone polymerase chain reaction of ring-closed plasmids," Appl Biochem Biotechnol. 2004 117(2):115-22.
Bird A., The essentials of DNA methylation. Cell, 70 (1992), pp. 5-8.
Birnboim HC and Doly J, A rapid alkaline extraction procedure for screening recombinant plasmid DNA. Nucleic Acids Res., (1979) vol. 7, No. 6, pp. 1513-1523.
Christensen LL and Josephsen J. "The Methyltransferase from the LlaDII Restriction-Modification System Influences the Level of Expression of Its Own Gene," J. Bacteriol., Jan. 2004; 186(2), pp. 287-295.
Clark SJ et al., High sensitivity mapping of methylated cytosines. Nucleic Acids Res. Aug. 11, 1994 22(15), pp. 2990-2997.
Cokus S. J. et al. Shotgun bisulphite sequencing of the *Arabidopsis* genome reveals DNA methylation patterning. Nature, vol. 452, pp. 215-219 (2008).
Edelheit O., et al., Simple and efficient site-directed mutagenesis using two single-primer reactions in parallel to generate mutants for protein structure-function studies. *BMC Biotechnol.* 2009 9:61, available at http://www.biomedcentral.com/1472-6750/9/61, pp. 1-8.
Fazzari MJ and Greally JM., Epigenomics: beyond CpG islands. Nat Rev Genet, vol. 5 (2004), pp. 446-455.
Finnegan EJ, The role of DNA methylation in plant development. In: Russo V., et al., editors. *Epigenetic Mechanisms of Gene Regulation*. Cold Spring Harbor Laboratory Press; Cold Spring Harbor, NY: 1996. pp. 127-140.
Geier GE and Modrich, P, Recognition Sequence of the dam Methylase of *Escherichia coli* K12 and Mode of Cleavage of Dpn I Endonuclease, J. Biol. Chem., vol. 254, No. 4 (1979), pp. 1408-1413.
Genbank Entry CP000580.1-ABN96632.1 restriction endonuclease (*Mycobacterium* sp. JLS), submitted Feb. 20, 2007.
Godon, JJ et al., Molecular Microbial Diversity of an Anaerobic Digestor as Determined by Small- Subunit rDNA Sequence Analysis. Appl. Environ. Microbiol., vol. 63, No. 7 (1997), pp. 2802-2813.
Grunau, C., et al., Bisulfite genomic sequencing: systematic investigation of critical experimental parameters, Nucleic Acids Res. vol. 29, No. 13 (2001), e65 , pp. 1-7.
Kobayashi,I, Behaviour of restriction-modification systems as selfish mobile elements and their impact on genome evolution. (2001), Nucleic Acid Res., vol. 29, No. 18, 3742-3756.
Larkin M.A., et al., Clustal W and Clustal X version 2.0, Bioinformatics, vol. 23, No. 21 (2007), pp. 2947-2948.
Li J., et al. Hairpin Fluorescence DNA probe for real-time monitoring of DNA Methylation, Anal. Chem. (2007) 79(3), pp. 1050-1056.
Li J., et al., "Site-directed mutagenesis by combination of homologous recombination and DpnI digestion of the plasmid template in *Escherichia coli*," Anal. Biochem., 2008 vol. 373 No. 2, pp. 389-391.
Li S and Wilkinson, MF, Site-directed mutagenesis: a two-step method using PCR and DpnI. *Biotechniques*. 1997 vol. 23, No. 4, pp. 588-590.
Lister, R. et al., Highly integrated single-base resolution maps of the epigenome in *Arabidopsis*. Cell, vol. 133, pp. 1-14 (2008), plus Supplemental Data, Cell, vol. 133 (2008), pp. 1-28.
Lister R., et al., Human DNA methylomes at base resolution show widespread epigenomic differences, Nature, (2009) vol. 462, pp. 315-322.
Liu H and Naismith, JH, An efficient one-step site-directed deletion, insertion, single and multiple-site plasmid mutagenesis protocol. BMC Biotechnol. 2008 8:91, available at http://www.biomedcentral.com/1472-6750/8/91, pp. 1-10.
MacNeil D.J., "Characterization of a Unique Methyl-specific Restriction System in *Streptomyces avermitilis*" Journal of Bacteriology, vol. 170, No. 12, 1988, 5607-5612.
McClelland et al., Site-specific cleavage of DNA at 8- and 10-base-pair sequences. Proc. Natl Acad. Sci., 1984 81(4): 983-987.
Messer,W., and Noyer-Weidner, M., Timing and Targeting: The Biological Functions of Dam Methylation in *E. coli*, Cell, vol. 54 (1988), pp. 735-737.
Messing J et al., Filamentous coliphage M13 as a cloning vehicle: Insertion of a HindII fragment of the Iac regulatory region in M13 replicative form in vitro, Proc. Natl. Acad. Sci., vol. 74, No. 9 (1977), pp. 3642-3646.
Messing et al., A system for shotgun DNA sequencing, Nucleic Acids Res., vol. 9, No. 2 (1981), pp. 309-321.
Mishra RN et al., "Directional genome walking using PCR," Biotechniques, vol. 33, No. 4 (2002), pp. 830-832, 834.
Modrich,P., Methyl-directed DNA mismatch correction, J. Biol. Chem., vol. 264 (1989), pp. 6597-6600.
Naito, T et al., Selfish behavior of restriction-modification systems, Science, vol. 267 (1995), pp. 897-899.
Ochman H., et al. Genetic applications of an inverse polymerase chain reaction. Genetics, vol. 120 (1988), pp. 621-623.
Patel, Y. et al., Cleavage at the twelve-base-pair sequence 5'TCTAGATCTAGA-3' using M.XbaI (TCTAGm6A) methylation and DpnaI (Gm6A/TC) cleavage. Nucleic Acids Res. 1990 18(6): 1603-1607.
Phalke et al., Retrotranspoon silencing and telomere integrity in somatic cells of *Drosophila* depends on the cytosine-5 methyltransferase DNMT2, Nature Genetics Advanced Online Publication, May 3, 2009, pp. 1-7; Supplement, Nature Genetics, vol. 41, 696-702 (2009), 1-29.
Raleigh,E.A., et al., *Escherichia coli* K-12 restricts DNA containing 5-methylcytosine. Proc. Natl Acad. Sci. USA, vol. 83, 9070-9074 (1986).
Reisenauer A. and Shapiro L., DNA methylation affects the cell cycle transcription of the CtrA global regulator in Caulobacter, EMBO J., vol. 21, No. 18 (2002), pp. 4969-4977.
Roberts,D. et al., IS10 Transposition Is Regulated by DNA Adenine Methylation, Cell, vol. 43, (1985), pp. 117-130.
Roberts R.J., and Halford S.E. Type II Restriction Nucleases, Nucleases 2nd Edition, Cold Spring Harbor Laboratory Press,( Linn, S., Lloyd S., Roberts, R., eds) (1993), pp. 35-88.
Roberts R.J. et al. A nomenclature for restriction enzymes, DNA methyltransferases, homing endonucleases and their genes. Nucleic Acids Res. vol. 31, No. 7 (2003), pp. 1805-1812.
Sanchez J.A. et al. The efficiency and timing of plasmid DNA replication in *Xenopus* eggs: correlations to the extent of prior chromatin assembly. J. Cell. Science, vol. 103 (1992), pp. 907-918.
Shareef M.M. et al. A noncommercial polymerase chain reaction-based method to approach one hundred percent recombinant clone selection efficiency. Anal. Biochem., vol. 382 (2008), pp. 75-76.
Srikhanta, Y.N. et al. The phasevarion: A genetic system controlling coordinated, random switching of expression of multiple genes. Proc. Nat. Acad. Sci. vol. 102, No. 15 (2005), pp. 5547-5551.
Stewart, F.J. and Raleigh, E.A. Dependence of McrBC Cleavage on Distance between Recognition Elements. Biol. Chem. vol. 379 (1998), pp. 611-616.
Striebel HM & Kessler C., Novel specific endonuclease activity recognizing a 10-bp sequence. Gene, vol. 172 (1996), pp. 47-48.
Tost J, editor. Methods in Molecular Biology. Humana Press, vol. 507: DNA Methylation: Methods and Protocols, 2009, 3-45, 55-64, 65-75, 77-87, 89-106, 107-116, 117-130, 131,148, 149-163, 177-205, 207-227, 229-240, 241-255, 271-280, 281-303, 325-337, 339-346.
Vovis G.F & Lacks, S. Complementary action of restriction enzymes endo R-DpnI and Endo R-DpnII on bacteriophage f1 DNA. J Mol Biol. vol. 115 (1977), pp. 525-538.
Wei D. et al. An improvement of the site-directed mutagenesis method by combination of megaprimer, one-side PCR and DpnI treatment. Anal Biochem. vol. 331 (2004), pp. 401-403.
Wilson,G.G. Organization of restriction-modification systems. Nucleic Acid Res., vol. 19, No. 10 (1991), pp. 2539-2566.
Wilson W.W., et al., Creation of the ultra-rare restriction sites in intact eucaryotic chromosomes mediated by bacterial methylases: an approach to sequencing and analyzing tumor and normal genomes. Anticancer Res. vol. 13 (1993), pp. 17-20.

Wobbe C.R. et al. In vitro replication of duplex circular DNA containing the simian virus 40 DNA origin site. Proc. Nat. Acad. Sci. vol. 82 (1985), pp. 5710-5714.

Wood R.J. et al. Kinetic Analysis of *Yersinia pestis* DNA Adenine Methyltransferase Activity Using a Hemimethylated Molecular Break Light Oligonucleotide. PLoS One. vol. 2, No. 8 (2007) e801, pp. 1-7.

Raleigh E.A., and Brooks J.E., Restriction Modification Systems: Where They Are and What They Do, Bacterial Genomes, Chapman & Hall, NY, (De Bruijn F.J., Lupski J.R. and Weinstock G.M., eds) (1998), pp. 78-92.

European Search Opinion for family application EP11155622.1, mailed Feb. 8, 2012 (5 pages).

Zheng et al., "A unique family of Mrr-like modification-dependent restriction endonucleases," Nucleic Acids Research, vol. 38, No. 16 (2010), pp. 5527-5534.

Great Britain Search Report (GB1003036.9), dated Jun. 22, 2010.

Tarasova et al., Substrate specificity of new methyl-directed DNA endonuclease GlaI, BMC Molecular Biology, vol. 9 (2008), pp. 1-12.

Mulligan et al., Differential binding of *Escherichia coli* McrA protein to DNA sequences that contain the dinucleotide m5CpG, Nucl. Acids Res., vol. 38 (2010), pp. 1997-2005.

Rina et al., Isolation and identification of restriction endonuclease SgrBI, Nucl. Acids Res., vol. 19, (1991), p. 6342.

Tautz et al., SgrAI, a novel class-II restriction endonuclease from *Streptomyces griseus* recognizing the octanucleotide sequence 5'-CR/CCGGYA-3', Nucl. Acid Res., vol. 18 (1990), p. 3087.

* cited by examiner

| Methyltrans-ferase | Sequence recognized and base modified | REase Ds2-324 | REase Tur2-TS24 | REase Sa27-m20 |
|---|---|---|---|---|
| M.SssI | m5CG | + | + | + |
| M.HpaII | Cm5CGG | + | + | + |
| M.HaeIII | GGm5CC | - | + | - |
| M.MvaI | C m4CWGG | - | - | - |

Turbt: 5'-biotin-TAY GCN AAR CAN AAR GAY CC - 3'

TK/LRIGQVL(R)YAKTKDPSNEV(E)(G)(G)(F)

TurN1:  5'- AAR CAN AAR GAY CCN TCN AA - 3'
TurN2:  5'- AAR CAN AAR GAY CCN AGY AA - 3'

WP1:  5'-CTA ATA CGA CTC ACT ATA GGG NNN NAT GC-3'
WP2:  5'-CTA ATA CGA CTC ACT ATA GGG NNN NGA TC-3'
WP3:  5'-CTA ATA CGA CTC ACT ATA GGG NNN NTA GC-3'
WP4:  5'-CTA ATA CGA CTC ACT ATA GGG NNN NCT AG-3'
WP5:  5'-CTA ATA CGA CTC ACT ATA GGG-3'

SEQUENCE LISTING

```
<160> NUMBER OF SEQ ID NOS: 34

<210> SEQ ID NO 1
<211> LENGTH: 434
<212> TYPE: PRT
<213> ORGANISM: Streptomyces griseoflavus

<400> SEQUENCE: 1

Met Thr Lys Trp Leu Arg Ile Gly Gln Val Leu Arg Tyr Ala Lys Thr
1               5                   10                  15

Lys Asp Pro Ser Asn Glu Val Glu Gly Gly Phe Pro Asn Phe Trp His
                20                  25                  30

Val Thr Gly Thr Pro Gly Ala Asn Arg Ala Leu Leu Glu Lys Gly Ile
            35                  40                  45

Asn Pro Ile Gly Glu Leu Asp Val Gln Ser Val Arg Arg Pro Ala
        50                  55                  60

Val Leu Ile Arg Ser Ser Pro Trp Lys Ala Gly Ser Asp Gln Thr Pro
65                  70                  75                  80

Trp His Asp Val Phe Asp Leu Glu His Gly His Val Arg Tyr Phe Gly
                85                  90                  95

Asp His Lys His Gly Leu Ala Lys Pro Thr Gly Ala Thr Glu Gly Asn
            100                 105                 110

Ala Ala Leu Leu Arg Ala Phe Glu Arg His Arg Ala Pro Ser Arg Glu
        115                 120                 125

Gln Arg Val Leu Ala Glu Pro Leu Leu Val Phe Arg Ser Val Thr Arg
    130                 135                 140

Gly Lys Ser Pro Lys Gly His Val Glu Phe Cys Gly Val Gly Leu Ile
145                 150                 155                 160

Glu Arg Ala Glu Arg Ile Val Gln Trp Gly Gly Ala Asn Arg Glu Thr
                165                 170                 175

Phe Val Asn Tyr Val Tyr Asp Phe Ala Met Leu Asp Leu Ser Glu Glu
            180                 185                 190

Gly Asp Gln Leu Asp Trp Ala Trp Ile Glu Ala Arg Arg Asn Val Glu
        195                 200                 205

Phe Thr Ala Glu Gln Ala Leu Lys Ala Ala Pro Arg Ser Trp Arg Ala
    210                 215                 220

Trp Val Glu Gly Gly His Ala Thr Leu Pro Lys Val Arg Arg Arg Val
225                 230                 235                 240
```

```
Ala Gln Thr Arg Val Val Lys Val Lys Asp Gln Lys Pro Thr Pro Gly
            245                 250                 255

Thr Ala Glu Ser Lys Asp Leu Asp Thr Ile Tyr His His Phe Asp Gly
        260                 265                 270

Arg Lys His Asp Phe Glu Ala Val Ala Ser Thr Val Ala Ala Arg Ile
    275                 280                 285

Leu Ser Phe Gly Ala Ser Tyr Arg His Gly Trp Leu Thr Arg Arg Ser
290                 295                 300

Gly Asp Gly Gly Ala Asp Phe Val Gly Arg Leu Asp Val Gly Arg Gly
305                 310                 315                 320

Leu Ala Gly Thr Ser Leu Val Val Leu Gly Gln Ala Lys Cys Val Lys
                325                 330                 335

Pro Glu Ser Thr Ile Ser Ala Glu Gln Ile Ala Arg Val Val Ala Arg
            340                 345                 350

Leu Arg Arg Gly Trp Ile Gly Val Phe Val Thr Thr Gly Ser Phe Ser
        355                 360                 365

Asp Ala Ala Gln Leu Glu Met Val Glu Asp Gln Tyr Pro Ile Ala Leu
    370                 375                 380

Val Asn Gly Arg Glu Leu Ala Arg Asp Leu Arg Met Met Ala Asn Glu
385                 390                 395                 400

His Tyr His Gly Asp Leu Ile Ala Cys Leu Asp Asp Ile His Gln Lys
                405                 410                 415

His Gly Thr Gly Thr Val Ile Thr Glu Arg Arg Pro Glu Glu Ile Leu
            420                 425                 430

Leu Glu

<210> SEQ ID NO 2
<211> LENGTH: 1305
<212> TYPE: DNA
<213> ORGANISM: Streptomyces griseoflavus

<400> SEQUENCE: 2
atgaccaaat ggttgcggat cggtcaggtg cttcgatacg cgaagaccaa agacccatcc      60
aacgaagttg aaggcggctt cccgaacttt tggcacgtaa ccgggactcc cggcgctaat     120
cgggcgctct tggagaaggg gatcaacccc attggtgagt tggacgtcca gagtgtggtg     180
cgtcgaccag cggtgctcat caggtccagt ccttggaagg ctgggagtga tcagacgccg     240
tggcacgacg tgttcgacct tgaacatgga cacgttcgct acttcgggga ccataagcat     300
ggtttggcga aacccaccgg cgctaccgag ggcaacgctg ccctgcttcg ggcattcgag     360
cggcaccgtg caccgtcaag agaacaacgt tgttggcag aaccgttgct cgtatttcgg      420
tccgtcaccc gtggtaagag ccctaagggg catgtcgagt ctgcggtgt gggcttgatc      480 gaacgtgccg agcgcatcgt tcagtggggc ggggccaacc gagagacgtt cgtcaactat     540
gtgtatgact cgccatgct tgatctctcg gaagagggag accaactcga ctgggcatgg      600
atcgaggcac ggcgcaacgt tgagttcacg gcagagcagg cgttgaaggc cgctccgcgg     660
tcttggcggg catgggttga gggtggtcac gcaaccttgc caaaggttcg acgacgtgtc     720
gctcagacgc gtgtggtgaa ggtgaaggac cagaagccaa cgccgggcac tgctgagtcg     780
aaggatctcg acacgatcta ccaccacttt gacggtcgca agcacgactt cgaggccgtc     840
gcgtccacgg tggccgctcg aatcctcagt ttcggagcct cctaccgaca tggctggctc     900
actcgtcgtt cgggtgacgg gggcgccgac ttcgttggcc gactcgatgt cggccgagga     960
ctggcaggca cgagtcttgt ggttctcggc caagccaagt gcgtgaagcc ggagagcacc    1020
```

```
atcagtgccg agcagatcgc ccgggttgtg gctcgtctgc gtcgcggctg gatcggggtg    1080
ttcgtcacga ccggatcctt ctccgacgct gcccagcttg agatggtcga ggatcagtac    1140
cccatcgcgc tggtcaacgg gcgggaacta gcccgtgatc tacggatgat ggccaacgag    1200
cactaccacg gggacttgat cgcttgcctc gatgacattc accagaagca tgggacgggc    1260
acggtcataa ctgaacgtcg gcccgaagag atcctgcttg agtag                    1305
```

<210> SEQ ID NO 3
<211> LENGTH: 427
<212> TYPE: PRT
<213> ORGANISM: Micromonospora aurantiaca

<400> SEQUENCE: 3

```
Met Arg Met Asn Ala Val Leu Arg Tyr Gly Arg Val Ala Ile Asp Leu
1               5                   10                  15

Pro Ile Ala Asp Gly Tyr Pro Asn Leu His Tyr Leu Ser Thr Gly Pro
            20                  25                  30

Ile Gly Thr Arg Val Leu Leu Glu Ser Gly Ile Asn Pro Val Arg Ser
        35                  40                  45

Ile Gly Ala Gln Gly Arg Gln Arg Arg Pro Val Ile Ala Leu Arg Ser
    50                  55                  60

Ser Pro Trp Lys Ala Gly Gly Glu Asp Thr Pro Trp His Asp Val Phe
65                  70                  75                  80

Asp Leu Asp His Gly His Val Arg Tyr Phe Gly Asp His Lys Val Ser
                85                  90                  95

Thr Asp Gly Pro Leu Gly Ser Thr Thr Gly Asn Lys Ala Leu Leu Glu
            100                 105                 110

Ala Trp Pro Gln His Arg Gly Ser Thr Pro Glu Thr Arg Ala Ala Ala
        115                 120                 125

Pro Pro Leu Leu Leu Phe Arg Ser Val Ser Val Gly Arg Ala Leu Lys
    130                 135                 140

Gly Tyr Ile Glu Phe Cys Gly Val Ala Val Leu Asp Arg Leu Glu His
145                 150                 155                 160

Val Val Gln Arg Asp Pro Ser Thr Gly Gln Ser Phe Ala Asn Tyr Ala
                165                 170                 175

Phe Asp Leu Thr Val Leu Ser Leu Ala Glu Glu Ala Glu Ala Ile Asp
            180                 185                 190

Trp Arg Trp Ile Asp Asp Arg Arg Asp Pro Gly Leu Ser Leu Gln Glu
        195                 200                 205

Thr His Arg His Ala Pro Arg Ser Trp Arg Arg Trp Val Glu His Gly
    210                 215                 220

Asp Pro Ile Leu Pro Arg Leu Arg Arg Val Ala Thr Ser Arg Val
225                 230                 235                 240

Arg Ser Lys Ser Asp Gln Arg Pro Glu Ala Gly Ser Val Glu Ala Gln
                245                 250                 255

Ile Leu Arg Arg Ile Tyr Glu Phe Tyr Gln Gly Arg Gln His Arg Phe
            260                 265                 270

Glu Leu Leu Ala Ala Arg Val Ala Ala Arg Val Phe Arg Gly Gln Gly
        275                 280                 285

Ala Val Tyr His Glu Gly Trp Leu Thr Arg Gly Ser Gly Asp Arg Gly
    290                 295                 300

Val Asp Phe Val Gly Arg Leu Asp Val Gly Ser Glu Asp Ala Ile Thr
305                 310                 315                 320

Ser Leu Val Val Leu Gly Gln Ala Lys Cys Arg Leu Asp Lys Ser Val
                325                 330                 335
```

```
Ser Ala Glu Glu Leu Ala Arg Val Val Ala Arg Leu Arg Arg Gly Trp
        340                 345                 350
Ile Gly Ala Tyr Val Thr Ile Ser Asp Tyr Ser Arg Asn Ala Gln Glu
            355                 360                 365
Glu Met Met Asp Asp Gln Tyr Pro Ile Val Leu Ile Asp Gly Arg Arg
    370                 375                 380
Leu Ala Glu Glu Val Arg Arg Met Ala Ser Asp Ser His Gly Gly Asn
385                 390                 395                 400
Leu Asn Thr Phe Leu Ser Glu Leu Ala Ser Gly Tyr Glu Glu Ala Val
                405                 410                 415
Thr Ser Arg Arg Pro Glu Glu Ile Leu Ser Leu
            420                 425

<210> SEQ ID NO 4
<211> LENGTH: 20
<212> TYPE: DNA
<213> ORGANISM: Artificial Sequence
<220> FEATURE:
<223> OTHER INFORMATION: Biotinylated primer Turbt
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 4
taygcnaarc anaargaycc                                               20

<210> SEQ ID NO 5
<211> LENGTH: 26
<212> TYPE: PRT
<213> ORGANISM: Streptomyces griseoflavus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Thr Lys Xaa Leu Arg Ile Gly Gln Val Leu Arg Tyr Ala Lys Thr Lys
1               5                   10                  15
Asp Pro Ser Asn Glu Val Glu Gly Gly Phe
            20                  25

<210> SEQ ID NO 6
<211> LENGTH: 20
<212> TYPE: DNA
<213> ORGANISM: Artificial Sequence
<220> FEATURE:
<223> OTHER INFORMATION: Primer TurNI
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
```

```
<400> SEQUENCE: 6
aarcanaarg ayccntcnaa                                              20

<210> SEQ ID NO 7
<211> LENGTH: 20
<212> TYPE: DNA
<213> ORGANISM: Artificial Sequence
<220> FEATURE:
<223> OTHER INFORMATION: Primer TurN2
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 7
aarcanaarg ayccnagyaa                                              20

<210> SEQ ID NO 8
<211> LENGTH: 29
<212> TYPE: DNA
<213> ORGANISM: Artificial Sequence
<220> FEATURE:
<223> OTHER INFORMATION: Walking primer WP1
<220> FEATURE:
<221> NAME/KEY: misc_feature
<222> LOCATION: (22)..(25)
<223> OTHER INFORMATION: n is a, c, g, or t

<400> SEQUENCE: 8
ctaatacgac tcactatagg gnnnnatgc                                    29

<210> SEQ ID NO 9
<211> LENGTH: 29
<212> TYPE: DNA
<213> ORGANISM: Artificial Sequence
<220> FEATURE:
<223> OTHER INFORMATION: Walking primer WP2
<220> FEATURE:
<221> NAME/KEY: misc_feature
<222> LOCATION: (22)..(25)
<223> OTHER INFORMATION: n is a, c, g, or t

<400> SEQUENCE: 9
ctaatacgac tcactatagg gnnnngatc                                    29

<210> SEQ ID NO 10
<211> LENGTH: 29
<212> TYPE: DNA
<213> ORGANISM: Artificial Sequence
<220> FEATURE:
<223> OTHER INFORMATION: Walking primer WP3
<220> FEATURE:
<221> NAME/KEY: misc_feature
<222> LOCATION: (22)..(25)
<223> OTHER INFORMATION: n is a, c, g, or t

<400> SEQUENCE: 10
ctaatacgac tcactatagg gnnnntagc                                    29

<210> SEQ ID NO 11
<211> LENGTH: 29
<212> TYPE: DNA
<213> ORGANISM: Artificial Sequence
<220> FEATURE:
<223> OTHER INFORMATION: Walking primer WP4
```

```
<220> FEATURE:
<221> NAME/KEY: misc_feature
<222> LOCATION: (22)..(25)
<223> OTHER INFORMATION: n is a, c, g, or t

<400> SEQUENCE: 11
ctaatacgac tcactatagg gnnnnctag                                          29

<210> SEQ ID NO 12
<211> LENGTH: 21
<212> TYPE: DNA
<213> ORGANISM: Artificial Sequence
<220> FEATURE:
<223> OTHER INFORMATION: Walking primer WP5

<400> SEQUENCE: 12
ctaatacgac tcactatagg g                                                  21

<210> SEQ ID NO 13
<211> LENGTH: 51
<212> TYPE: DNA
<213> ORGANISM: Artificial Sequence
<220> FEATURE:
<223> OTHER INFORMATION: Oligonucleotide MZ-95

<400> SEQUENCE: 13
acttcacgcc agaatacgaa agaccaggta tatgcacaaa atgagatgct t                 51

<210> SEQ ID NO 14
<211> LENGTH: 51
<212> TYPE: DNA
<213> ORGANISM: Artificial Sequence
<220> FEATURE:
<223> OTHER INFORMATION: Oligonucleotide MZ-96
<220> FEATURE:
<221> NAME/KEY: modified_base
<222> LOCATION: (25)..(25)
<223> OTHER INFORMATION: m5c

<400> SEQUENCE: 14
acttcacgcc agaatacgaa agaccaggta tatgcacaaa atgagatgct t                 51

<210> SEQ ID NO 15
<211> LENGTH: 51
<212> TYPE: DNA
<213> ORGANISM: Artificial Sequence
<220> FEATURE:
<223> OTHER INFORMATION: Oligonucleotide MZ-97

<400> SEQUENCE: 15
aagcatctca ttttgtgcat atacctggtc tttcgtattc tggcgtgaag t                 51

<210> SEQ ID NO 16
<211> LENGTH: 51
<212> TYPE: DNA
<213> ORGANISM: Artificial Sequence
<220> FEATURE:
<223> OTHER INFORMATION: Oligonucleotide MZ-98
<220> FEATURE:
<221> NAME/KEY: modified_base
<222> LOCATION: (25)..(25)
<223> OTHER INFORMATION: m5c

<400> SEQUENCE: 16
aagcatctca ttttgtgcat atacctggtc tttcgtattc tggcgtgaag t                 51

<210> SEQ ID NO 17
<211> LENGTH: 21
```

```
<212> TYPE: DNA
<213> ORGANISM: Artificial Sequence
<220> FEATURE:
<223> OTHER INFORMATION: Oligonucleotide spec-top
<220> FEATURE:
<221> NAME/KEY: misc_feature
<222> LOCATION: (1)..(1)
<223> OTHER INFORMATION: 5' biotin

<400> SEQUENCE: 17
ccacgaagac ccagaatacg a                                              21

<210> SEQ ID NO 18
<211> LENGTH: 53
<212> TYPE: DNA
<213> ORGANISM: Artificial Sequence
<220> FEATURE:
<223> OTHER INFORMATION: Oligonucleotide spec-bot
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: modified_base
<222> LOCATION: (29)..(29)
<223> OTHER INFORMATION: m5c
<220> FEATURE:
<221> NAME/KEY: misc_feature
<222> LOCATION: (30)..(30)
<223> OTHER INFORMATION: n is a, c, g, or t

<400> SEQUENCE: 18
ggtgcttctg ggtcttatgc tttctnnncn atatacgtgt tttaatcatc gaa           53

<210> SEQ ID NO 19
<211> LENGTH: 16
<212> TYPE: DNA
<213> ORGANISM: Artificial Sequence
<220> FEATURE:
<223> OTHER INFORMATION: Primer w001

<400> SEQUENCE: 19
agtttgatcm tggctc                                                    16

<210> SEQ ID NO 20
<211> LENGTH: 18
<212> TYPE: DNA
<213> ORGANISM: Artificial Sequence
<220> FEATURE:
<223> OTHER INFORMATION: Primer w002
<220> FEATURE:
<221> NAME/KEY: misc_feature
<222> LOCATION: (2)..(2)
<223> OTHER INFORMATION: n is a, c, g, or t

<400> SEQUENCE: 20
gntaccttgt tacgactt                                                  18

<210> SEQ ID NO 21
<211> LENGTH: 11
<212> TYPE: PRT
<213> ORGANISM: Streptomyces griseoflavus

<400> SEQUENCE: 21

Tyr Ala Lys Thr Lys Asp Pro Ser Asn Glu Val
1               5                   10

<210> SEQ ID NO 22
<211> LENGTH: 20
<212> TYPE: DNA
```

```
<213> ORGANISM: Artificial Sequence
<220> FEATURE:
<223> OTHER INFORMATION: Primer R1T

<400> SEQUENCE: 22
gttacgtgcc aaaagttcgg                                               20

<210> SEQ ID NO 23
<211> LENGTH: 20
<212> TYPE: DNA
<213> ORGANISM: Artificial Sequence
<220> FEATURE:
<223> OTHER INFORMATION: Primer D1T

<400> SEQUENCE: 23
gtgtgttggc agaaccgttg                                               20

<210> SEQ ID NO 24
<211> LENGTH: 19
<212> TYPE: DNA
<213> ORGANISM: Artificial Sequence
<220> FEATURE:
<223> OTHER INFORMATION: Primer d2T

<400> SEQUENCE: 24
cgtcacgacc ggatccttc                                                19

<210> SEQ ID NO 25
<211> LENGTH: 18
<212> TYPE: DNA
<213> ORGANISM: Artificial Sequence
<220> FEATURE:
<223> OTHER INFORMATION: Primer r2T

<400> SEQUENCE: 25
ccgcgacgca gacgagcc                                                 18

<210> SEQ ID NO 26
<211> LENGTH: 27
<212> TYPE: PRT
<213> ORGANISM: Streptomyces griseoflavus

<400> SEQUENCE: 26

Met Thr Lys Trp Leu Arg Ile Gly Gln Val Leu Arg Tyr Ala Lys Thr
1               5                   10                  15

Lys Asp Pro Ser Asn Glu Val Glu Gly Gly Phe
            20                  25

<210> SEQ ID NO 27
<211> LENGTH: 28
<212> TYPE: DNA
<213> ORGANISM: Artificial Sequence
<220> FEATURE:
<223> OTHER INFORMATION: Primer Turpr

<400> SEQUENCE: 27
tatttaaatg accaaatggt tgcggatc                                      28

<210> SEQ ID NO 28
<211> LENGTH: 26
<212> TYPE: DNA
<213> ORGANISM: Artificial Sequence
<220> FEATURE:
<223> OTHER INFORMATION: Primer Turgal

<400> SEQUENCE: 28
```

```
tgcggccgcc aagctcagtc ggacga                                            26
```

```
<210> SEQ ID NO 29
<211> LENGTH: 25
<212> TYPE: DNA
<213> ORGANISM: Artificial Sequence
<220> FEATURE:
<223> OTHER INFORMATION: pUC57 insert

<400> SEQUENCE: 29
ctagatatcc cgaagacttt tctcg                                             25

<210> SEQ ID NO 30
<211> LENGTH: 25
<212> TYPE: DNA
<213> ORGANISM: Artificial Sequence
<220> FEATURE:
<223> OTHER INFORMATION: pUC57 insert

<400> SEQUENCE: 30
gatccgagaa aagtcttcgg gatat                                             25

<210> SEQ ID NO 31
<211> LENGTH: 31
<212> TYPE: DNA
<213> ORGANISM: Artificial Sequence
<220> FEATURE:
<223> OTHER INFORMATION: pUC-X vector segment

<400> SEQUENCE: 31
tctagatatc ccgaagactt ttctcggatc c                                      31

<210> SEQ ID NO 32
<211> LENGTH: 31
<212> TYPE: DNA
<213> ORGANISM: Artificial Sequence
<220> FEATURE:
<223> OTHER INFORMATION: pUC-X vector segment

<400> SEQUENCE: 32
ggatccgaga aaagtcttcg ggatatctag a                                      31

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide Rand-30-1
<220> FEATURE:
<221> NAME/KEY: misc_feature
<222> LOCATION: (1)..(4)
<223> OTHER INFORMATION: n is a, c, g, or t

<400> SEQUENCE: 33
nnnnaagcgt gatagagcga ttctggctcg                                        30

<210> SEQ ID NO 34
<211> LENGTH: 26
<212> TYPE: DNA
<213> ORGANISM: Artificial Sequence
<220> FEATURE:
<223> OTHER INFORMATION: Primer Rand-30-1-rev

<400> SEQUENCE: 34
cgagccagaa tcgctctatc acgctt                                            26
```

RESTRICTION ENDONUCLEASES AND THEIR APPLICATIONS

FIELD OF THE INVENTION

The present invention relates to a methylation-specific restriction endonuclease and uses thereof including site-specific cleavage of DNA samples, determination of the level of cytosine of methylation in a DNA sample, genome-wide analysis of individual 5-methylcytosines, and whole genome-analysis of DNA methylation patterns.

BACKGROUND OF THE INVENTION

Restriction—modification (RM) systems are widespread among prokaryotic organisms (Roberts & Halford, 1993; Raleigh & Brooks, 1998). They are composed of two enzymatic activities. One of them, DNA methylation activity, ensures modification of A or C base within the specific DNA sequence. This site-specific modification protects the host DNA from the action of the other, endonucleolytic activity of the same specificity (Wilson, 1991). The biological function of complete RM systems is generally thought to be the protection of the host genome against foreign DNA, in particular bacteriophage DNA. However, at least two other hypotheses of the biological function of RM systems were proposed in the last few years. According to the hypothesis of Arber, RM enzymes are regarded as modulators of the frequency of genetic variation (Arber, 2000). An alternative hypothesis considers RM genes to be selfish mobile genetic elements, like viruses or transposons that invade genomes without necessarily providing selective advantages (Kobayashi, 2001; Naito et al, 1995). In addition, some prokaryotic DNA methyltransferases (MTases) and restriction endonucleases may execute other functions. For instance, modification of specific DNA sequences may regulate chromosomal DNA replication (Messer & Noyer-Weidner, 1988) and expression of genes (Barras & Marinus, 1989; Christensen & Josephsen, 2004; Beletskaya et al, 2000; Reisenauer & Shapiro, 2002; Srikhanta et al, 2005; Roberts et al, 1985), or may be involved in DNA mismatch repair (Modrich, 1989).

The latest classification attributes all known restriction endonucleases to four types (Roberts et al, 2003). Of these, Type II enzymes are the most important due to their unique property to recognize short specific DNA targets and cleave DNA at a fixed position either within DNA target or very close to it. This property made them indispensable in recombinant DNA technologies. Type II enzymes are very heterogeneous and are further classified into several subdivisions. One of them, Type IIM, encompasses enzymes that recognize specific methylated sequences in DNA and cleave at a fixed site. There are several enzymes which belong to this group (DpnI, GlaI, GluI, BisI, BlsI, PcsI). Of these, DpnI and its isoschizomers (i.e. restriction enzymes which recognize the same DNA target and cleave at the same position) recognize DNA targets containing the modified adenine (5'-Gm6ATC-3'), while all other listed enzymes recognize DNA targets which contain 5-methylcytosine. The key characteristics of known Type IIM enzymes are that they recognize symmetric DNA targets containing modified bases on both DNA strands, and cleave both DNA strands within the target.

Type IV restriction enzymes recognize and cleave modified DNA as well. However, in contrast to Type IIM enzymes, the Type IV representatives cleave DNA at an undefined position. In addition, the exact recognition target has been determined for only one of them, McrBC from *Escherichia coli* K-12. McrBC recognizes two RmC dinucleotides (R stands for purine, mC—for methylated cytosine, either m4C or m5C) which are separated by anywhere from 40 to 3000 base pairs. Cleavage occurs in between these two sites, but closer to one of them, approximately 30 base pairs from the methylated base (Raleigh & Wilson, 1986; Stewart & Raleigh, 1998).

The ability of methyl-dependent enzymes to differentiate between modified and non-modified DNA molecules or their regions has found many practical applications. Of note, applications differ significantly depending on both the type of restriction enzyme and the type of modified base which is recognized by particular restriction enzyme.

DpnI cleaves DNA targets which comprise a 4 nt recognition sequence containing m6A such as those modified by *Escherichia coli* enzyme Dam methyltransferase (Geier & Modrich, 1979). The Dam targets of plasmids isolated from *E. coli* dam$^+$ strains become modified and thus susceptible to DpnI cleavage. Based on this feature a simple and efficient site-directed mutagenesis method was developed, in which a pair of mutagenic primers is annealed to opposite strands of Dam-methylated plasmid DNA to be mutagenised, several rounds of linear amplification are carried out, and then parental DNA molecules are selectively cleaved by DpnI at modified Dam sites, leaving newly synthesized circular non-methylated double-stranded DNA molecules intact. The closed double-stranded DNA corresponding to the parental template molecules, but containing the desired mutation or mutations of interest, may be recovered from the transformed cells (U.S. Pat. No. 5,789,166). Later on DpnI was employed in a plethora of similar site-directed mutagenesis approaches, in all cases serving for the cleavage of parental molecules before transformation (US Patent Application 20060228786; Edelheit et al., 2009; Liu & Naismith, 2008; Li et al., 2008; Wei et al., 2004; Bichet et al., 2004; Li & Wilkinson, 1997). In addition, the ability of DpnI to cleave methylated DNA molecules was used to select for recombinant molecules (Shareef et al., 2008) and for investigation of Dam methylation kinetics (Wood et al., 2007; Li et al., 2007).

For efficient enrichment by mutagenised double-stranded DNA molecules after site-directed mutagenesis methylation-specific restriction endonucleases like DpnI need to cleave both the fully methylated parental double-stranded DNA molecules and the hemi-methylated DNA molecules, which are newly synthesized strands combined with parental strands. If not cleaved, hemi-methylated DNA molecules may be repaired back to the initial genotype after transformation, resulting in reduced efficiency of mutagenesis. However, literature reports relating to the ability of DpnI to cleave hemi-methylated GATC targets are contradictory. For instance, some authors claim that DpnI does not cleave hemi-methylated targets (Vovis & Lacks, 1977); others observed that site-specific cleavage of hemi-methylated substrates is very slow (Wood et al., 2007; http://www.neb.com) and depends on the concentration of sodium chloride, where an increase in salt concentration results in increased specificity of DpnI for the doubly-methylated substrate (Wobbe et al., 1985; Sanchez et al., 1992). DpnI therefore has its limitations: hemi-methylated DNA substrates are cleaved very slowly by DpnI, high enzyme and low salt concentrations are required to induce cleavage of such substrates. Most importantly, there remains a level of uncertainty regarding the performance of DpnI on hemi-methylated DNA substrates because it is impossible to distinguish between cleavage of fully methylated and hemi-methylated DNA substrates in reaction mixtures where both types of DNA molecules are present. Thus, a need exists for restriction enzymes which recognize hemi-methylated double-stranded DNA targets and cleave them efficiently at a fixed position, yielding reaction products which can be easily visualized by gel electrophoresis and staining.

Epigenetics is an application for which both Type II M and IV enzymes are known, where m5C-specificity is most important. Type IIM representatives (GlaI, GluI, BisI, BlsI, PcsI) cleave both DNA strands within their recognition site, which is from 4 to 6 nucleotides in length with at least one 5-methylcytosine in each DNA strand (Russian patent application RU 2270859; http://www.sibenzyme.com/products/m2_type). In contrast, the best-characterized Type IV restriction endonuclease McrBC recognizes two remote RmC dinucleotides and cleaves both DNA strands between these two sites, but closer to one of them, approximately 30 base pairs from the methylated base.

The enzymatic conversion of cytosine to 5-methylcytosine is one of most important epigenetic changes in vertebrate and plant genomes (Bird, 1992; Finnegan, 1996). It occurs mainly within the dinucleotide CG, and this epigenetic change plays important roles in transcriptional gene silencing, development, aging, cancer and other diseases (reviewed in: Jörg Tost, 2009, pp. 3-23). There are various methods available for studying DNA methylation. Some of them provide information about the degree of global genomic DNA methylation (reviewed in: Jörg Tost, 2009, pp. 23-45), the others are directed towards analysis of the DNA methylation status of specific sequences and the discovery of new methylation hot spots. In general, there are three major approaches which are used to distinguish between modified and non-modified DNA regions (however, there are many techniques which combine two out of three approaches listed below).

The first approach takes advantage of a chemical reaction using sodium bisulfite, which selectively deaminates cytosine to uracil, while m5C is resistant to this conversion (Clark et al., 1994). This chemical reaction results in primary sequence change in the DNA. The modified DNA strands could be amplified by use of polymerase chain reaction and analyzed using different techniques (reviewed in: Jörg Tost, 2009). Of these, genome-wide deep sequencing provides the most comprehensive information, revealing not only modified cytosines and their contexts, but also the level of methylation of particular cytosine within the genome in population of analyzed cells. Very recently shotgun bisulfite sequencing of the *Arabidopsis* genome revealed that only 55% of modified cytosines are located within the dinucleotide CG, while 23% are found within CHG (H stands for A, C or T) and 22%—within CHH (Lister et al., 2008), and it might be that eukaryotic DNA methyltransferases possess sequence preferences beyond the CG, CHG and CHH contexts (Cokes et al., 2008). Surprisingly, nearly one-quarter of all modified cytosines identified in human embryonic stem cells IMR90 were in the context of CHG or CHH as well, but non-CG methylation disappeared after induction of differentiation (Lister et al., 2009). The bisulfite-based approach is the "gold standard" of epigenetic studies. However, after sodium bisulfite conversion of cytosines the genome consists of only three DNA bases (U or T, A, G), therefore bioinformatics challenges will need to be overcome in order to predict the genomic location of obtained DNA sequences precisely. Furthermore, bisulfite sequencing remains time consuming and costly, especially when the methylation state of a large number of loci has to be investigated. Finally, the most critical step of bisulfite approach is the completeness of sodium bisulfite-catalyzed conversion of cytosines. However, sodium bisulfite treatment causes significant sample loss due to DNA degradation (Grunau et al., 2001). Therefore, a choice of a right balance between completeness of the modification and an acceptable loss of DNA sample is necessary. As a result, some fraction of cytosines remains unaltered, resulting in false-positive signals.

The second approach involves the use of m5C-binding proteins, allowing selective isolation of modified DNA regions. Comparison of methylation levels of individual DNA regions can be carried our using several different approaches (reviewed in: Jörg Tost, 2009). However, this type of analysis suffers from low resolution and an inability to identify the precise sequence context of methylation site(s).

The third approach is based on the use of either methylation-sensitive restriction enzymes like HpaII or NotI (recognition targets CCGG and GCGGCCGC, respectively), or methylation-specific (methylation-dependent) restriction enzymes like Type IV enzyme McrBC or any of Type IIM representatives GlaI, GluI, BisI, BlsI, PcsI. Methylation-sensitive enzymes do not cleave DNA if their recognition targets contain m5C within the CG dinucleotide. In contrast, methylation-specific enzymes will cleave modified DNA targets, leaving non modified ones intact. Detection of individual DNA fragments and evaluation of their methylation levels at particular CG targets (which are recognized and cleaved either by methylation-sensitive restriction enzyme or by methylation-specific Type IIM restriction enzyme) can be carried out directly by using Southern hybridization. Also, there are several approaches which involve amplification of DNA (pre-cleaved either with methylation-sensitive enzyme, or with methylation-specific enzyme, or with both) followed by detection of amplified fragments by means of different approaches (US Patent Application 20060275806; US Patent Application 20090004646; US Patent Application 20050272065; US Patent Application 20050158739; US Patent Application 20050153316; methods reviewed in: Jörg Tost, 2009).

Unfortunately, only a tiny fraction of methylated cytosines can be targeted using these assays. For example, only 3.9% of all nonrepeat CGs in the human genome reside within recognition sites of the HpaII enzyme (Fazzari & Greally, 2004). Furthermore, HpaII and other methylation-sensitive enzymes are not suitable for analysis of methylated bases within contexts other then CG (for instance, CHG or CHH). The same is true for methylation-specific Type IIM enzymes GlaI, GluI, BisI, BlsI and PcsI which recognize symmetric targets of 4-6 nucleotides in length. In contrast, Type IV enzyme McrBC, which DNA recognition target is RmC, recognizes ~50% of all CG, CHH and CHG targets containing m5C. However, McrBC recognizes two remote RmC dinucleotides and cleaves both DNA strands between these two sites at a non specified position. Therefore, the cleavage position does not provide information which could be used for prediction of modified cytosine, and McrBC cannot be used for such type of analysis.

In summary, it may be concluded that all major approaches which are used today for investigation of DNA methylation status suffer from various drawbacks. In case of methylation-dependent restriction enzymes the major drawback of m5C-specific Type IIM enzymes is their relatively long specific recognition sequence (4-6 nt in length) and a need for presence of two or more modified cytosines within the target, limiting their usage down to the small fraction of m5C-containing regions. The Type IV enzyme McrBC has a potential to recognize up to 50% of all modified cytosines, but it suffers from cleavage at a non-specified position, making it impossible to identify modified cytosines from analysis of cleavage reaction products. Thus, a need exists for methylation-dependent restriction enzymes which do not suffer from these drawbacks.

SUMMARY OF THE INVENTION

In a first aspect, the present invention provides a methylation-specific restriction endonuclease for a DNA duplex substrate, which endonuclease recognizes in a strand of the duplex a 2 to 6 nucleotide recognition sequence comprising a 5-methylcytosine, and cleaves each strand of the duplex at a fixed position outside the recognition sequence.

A new class of restriction endonucleases has been discovered and characterised. Enzymes belonging to this class recognise those short specific DNA targets which comprise a C5-methylated nucleotide in one DNA strand and yet cleave both DNA strands at a fixed position. Thus, both fully methylated and hemi-methylated double-stranded DNA targets are recognised and cleaved at a fixed position, yielding reaction products which may be easily characterised.

The methylation-specific restriction endonucleases of the present invention may be used in multiple applications. One such application is site-specific cleavage of fully- and hemi-methylated DNA duplexes in all techniques where differentiation between methylated and non-methylated DNA duplexes is required, for instance in site-directed mutagenesis experiments. Here there is a need to remove fully methylated parental double-stranded DNA molecules and hemi-methylated DNA molecules, i.e. newly synthesized strands which are combined with parental strands. Another important field of application is epigenetic studies. The present invention describes three major types of research and/or diagnostics which may be realized exploring unique properties of restriction enzymes of present invention: (i) analysis of the level of global cytosine methylation at the 5 position; (ii) genome-wide analysis of individual 5-methylcytosines; and (iii) whole genome analysis of DNA methylation patterns.

A restriction endonuclease according to the invention cleaves each strand of the duplex at a fixed position outside the recognition sequence typically to form a "sticky" end where there is an overhang of one or more nucleotides in the double-stranded reaction product. Preferably, the DNA duplex substrate is cleaved in the strand comprising the 5-methylcytosine at a position which is 12 nucleotides from the 5-methylcytosine in the 3' direction. Advantageously, the strands are cleaved so as to produce a 5' overhang which is preferably 4 nucleotides. Thus, the DNA strand complementary to the strand cleaved at 12 nucleotides from the 5-methylcytosine in the 3' direction is cleaved at a position which is preferably 16 nucleotides away in the 5' direction from the corresponding G base. Advantageously, the restriction endonuclease is a recombinant molecule.

According to one arrangement, the recognition sequence is m5CNNG where N denotes any nucleotide. According to another arrangement, the recognition sequence is Cm5C. Restriction endonucleases according to the present invention may be obtainable from *Streptomyces*, such as *Streptomyces griseoflavus* and *Streptomyces griseus*. One enzyme capable of recognizing recognition sequence m5CNNG may be obtainable from *Streptomyces griseoflavus* strain RFL11. This enzyme preferably comprises a primary amino acid sequence SEQ ID NO:1 or a sequence which is at least 90% identical thereto. Restriction endonucleases according to the invention may be encoded by the nucleotide sequence SEQ ID NO:2 or sequence which is at least 90% identical thereto. One enzyme capable of recognizing recognition sequence Cm5C may be obtained from *Streptomyces griseus* strain RFL12. An enzyme according to the invention may have a primary amino acid sequence which is at least 50% identical to the amino acid sequence of SEQ ID NO:1 or a nucleotide sequence which is at least 50% identical to the nucleotide sequence of SEQ ID NO:2. A restriction endonuclease may be obtainable from *Micromospora*, particularly *Micromospora aurantiaca*. Sequence SEQ ID NO:3 shows an amino acid sequence from *Micromospora aurantiaca* which possesses approximately 50% identity with SEQ ID NO:1.

In a further aspect, the present invention provides the use of a restriction endonuclease as described herein for the site-specific cleavage of a sample comprising double-stranded DNA which contains 5-methylcytosine in one or both strands, wherein the double-stranded DNA is completely digested.

There is further provided a method for site-specific cleavage of double-stranded DNA which contains 5-methylcytosine in one or both strands, which method comprises the steps of mixing DNA with buffer and enzyme as defined herein and the incubation of the reaction mixture so as to digest the double-stranded DNA completely.

This use or method may be applied to samples which further comprise target double-stranded DNA which is free of 5-methylcytosine. The target double-stranded DNA remains undigested. Thus, a means is provided for removing from samples double-stranded DNA which contains 5-methylcytosine in one or both strands such as in the case where a site-specific mutagenesis operation has been performed and there is a need to select from the sample non-parental DNA molecules for further processing. Detection of double-stranded 5-methylcytosine free DNA molecules which remain intact may be effected by various approaches including transformation and amplification such as polymerase chain reaction (PCR).

In a further aspect, the present invention provides use of a restriction endonuclease as described herein, for determining in a test DNA sample the level of methylation of cytosine at the 5 position, wherein the sample is treated with the restriction endonuclease to cleave DNA containing 5-methylcytosine into reaction products, the reaction products are treated with a DNA polymerase in the presence of at least one labelled deoxynucleotide or analogue thereof capable of being incorporated into the reaction products by the DNA polymerase, and the amount of incorporated label is measured to indicate the level of methylation of cytosine at the 5 position. In this way the level of global cytosine methylation at the 5 position may be determined.

A method for determining the level of methylation of cytosine at the 5-position is also provided wherein at least one restriction enzyme as described herein is used to cleave the DNA sample and the reaction products are incubated with a DNA polymerase in the presence of at least one labelled deoxynucleotide or analogue thereof capable of being incorporated into the reaction products by the DNA polymerase. The amount of incorporated label is measured.

Preferably, the amount of incorporated label is measured to indicate the level of methylation of cytosine at the 5-position by comparison with the amount of label incorporated into a control DNA sample which is the same as the test sample (a) without treatment with the restriction endonuclease; and (b) which was pretreated with SssI methyltransferase to modify all cytosines within CG dinucleotides. Thus, the amount of label resulting after the treatment with DNA polymerase is compared with a situation where cleavage does not take place, and where all cytosines are methylated.

Alternatively, the amount of incorporated label may be measured to indicate the level of methylation of cytosine at the 5 position by comparison with the amount of label incorporated into a control DNA sample which is the same as the test sample (a) without treatment with the restriction endonuclease, (b) which was digested with methylation-non sensitive Type II restriction endonuclease having a constant number of targets within the genome and resulting in 5'-protruding termini instead of the methylation-specific restriction endonuclease, and (c) which was digested with a Type II restriction endonuclease simultaneously with the methylation-specific restriction endonuclease. Thus, a method may be provided wherein the sample is incubated with DNA polymerase in the presence of at least one labeled deoxynucleotide or its analogue and the amount of label incorporation measured under conditions (a), (b) and (c) above.

In one arrangement, the at least one labeled deoxynucleotide or analogue thereof is a DNA synthesis terminator so that only one labeled deoxynucleotide is incorporated into the end of each DNA cleavage reaction product.

The label of the deoxynucleotide may be any label commonly used with DNA polymerase, including a radioactive label, such as $^{32}P$, $^{33}P$; a fluorescent label such as Cy3, Cy5, or fluoresceine; or a covalently coupled chemical compound labels such as biotin or digoxigenin.

The DNA under investigation may be isolated from a single cell.

In a further aspect, the present invention provides use of a restriction endonuclease as described herein for genome-wide analysis of individual 5-methylcytosines, wherein a DNA sample is treated with the restriction endonuclease to cleave DNA containing 5-methylcytosine into reaction products, the reaction products are included with a nucleic acid ligase in the presence of a synthetic nucleic acid of known sequence to generate ligated molecules comprising the synthetic nucleic acid and an individual reaction product, the ligated molecules are individually sequenced using the nucleotide sequence information from the ligated synthetic nucleic acid, and individual 5-methylcytosines are identified which are (a) at the correct distance from the 5'-end of ligated synthetic nucleic acid, based on the cleavage behavior of the methylation-specific restriction endonuclease and (b) which occur in the correct sequence context.

A method for genome-wide analysis of individual 5-methylcytosines is also provided, which comprises cleaving the DNA sample under investigation with at least one restriction enzyme as described herein, incubating the cleaved reaction products with a nucleic acid ligase in the presence of a synthetic nucleic acid; analyzing the sequence of individual ligated molecules using the nucleic sequence information provided by the ligated synthetic nucleic acid; identifying individual m5-cytosines which are (a) at the correct distance from the 5'-end of ligated synthetic nucleic acid, and (b) which occur in the correct sequence context, representing the target of the methylation-specific restriction enzyme as described herein.

In the use or method of this aspect of the invention the reaction products may advantageously be treated by phosphatase so as to remove 5'-phosphates from the resulting fragments of DNA under investigation.

In one arrangement, the nucleic acid ligase is DNA ligase, which catalyses the formation of a phosphodiester bond between juxtaposed 5'-phosphate and 3'-hydroxyl termini of nucleic acids.

The synthetic nucleic acid may be in single stranded form and preferably has four unspecified bases (5'-NNNN) at the 5' end.

Alternatively, the synthetic nucleic acid may be in double-stranded linear form such as in double-stranded hairpin form.

The synthetic nucleic acid typically comprises DNA or may comprise a mixture of deoxyribonucleotides and other types of nucleic acids such as RNA or LNA. In addition, the synthetic nucleic acid may be modified by a covalently coupled fluorescent label such as Cy3, Cy5 or fluoresceine or by a covalently coupled chemical compound such as biotin or digoxigenin.

The ligated DNA molecules may be amplified by any existing amplification technique such as PCR, isothermal amplification or transcription-mediated amplification. The ligated DNA molecules may be treated with bisulphite before single-molecule sequencing or they may be treated with bisulphite before amplification.

Again, the DNA under investigation may be isolated from a single cell.

In a further aspect, the present invention provides the use of a restriction endonuclease as defined herein for whole genome analysis with DNA methylation, wherein a DNA sample is treated with the restriction endonuclease to cleave DNA containing 5-methylcytosine into reaction products, the reaction products are treated with a nucleic acid ligase in the presence of a synthetic nucleic acid of known sequence to generate ligated molecules, the ligated molecules are amplified using the nucleotide sequence information from the ligated synthetic nucleic acid and the amplified products are detected.

A method for whole genome analysis of DNA methylation patterns is also provided, the method comprising the steps of cleaving the DNA sample under investigation with at least one restriction enzyme as defined herein, incubating the reaction products with a nucleic acid ligase in the presence of a synthetic nucleic acid; amplifying the ligation reaction products using the nucleotide sequence information provided by the ligated synthetic nucleic acid; and detecting of the amplified DNA fragments using any suitable platform.

In the use or method of this aspect of the invention, suitable detection platforms include filter hybridization and microarrays.

The reaction products may be treated with phosphatase so as to remove 5'-phosphates.

The nucleic acid ligase may be a DNA ligase which catalyses the formation of a phosphodiester bond between juxtaposed 5'-phosphate and 3'-hydroxyl termini of nucleic acids. In one arrangement, the synthetic nucleic acid is in single-stranded form and preferably has four unspecified bases (5'-NNNN) at the 5' end. Alternatively, the synthetic nucleic acid is in a double-stranded linear form such as a double-stranded hairpin form. The synthetic nucleic acid may comprise DNA or a mixture of deoxyribonucleotides and other types of nucleic acids such as RNA or LNA.

The synthetic nucleic acid may be modified by a covalently coupled fluorescence label such as Cy3, Cy5 or fluoresceine or by covalently coupled chemical compound such as biotin or digoxigenin.

The ligated molecules may be treated with bisulphite before amplification.

The ligated DNA molecules may be amplified by any existing amplification techniques including polymerase chain reaction, isothermal amplification and transcription-mediated amplification.

The DNA sample may be from a single cell.

Those skilled in the art will recognize that the provided teaching can readily be applied to methylation-specific restriction endonucleases other than those described in this invention, but possessing similar primary structure and similar biochemical properties. They will also recognize that the provided teaching describes only major points of practical applications, while non-essential improvements of the experimental outline and/or technical details cannot alter the essence of the invention and the scope of applications described therein.

The present invention will now be described in further detail, by way of example only, with reference to the accompanying Figures and the following Experiments and Examples.

DETAILED DESCRIPTION

Figure 1:
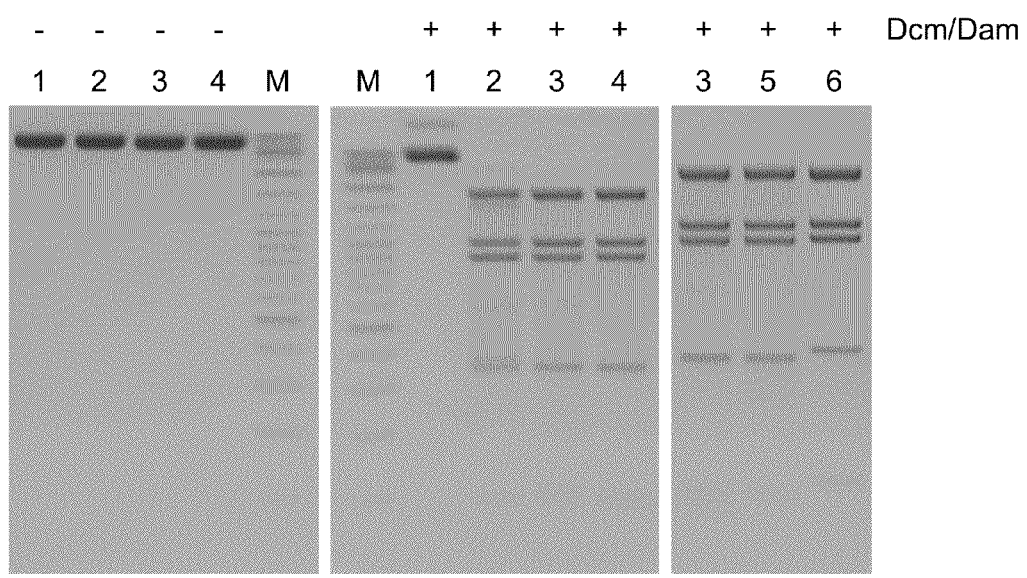
FIG. 1 shows the activity of partially purified preparations of restriction endonucleases from natural bacterial isolates Ds2-324, Tur2-TS24 and Sa27-m20 on plasmid DNA substrates which are either not methylated (pSEAd6/BamHI) or Dam and Dcm modified (pBR322). Lane 1—control DNA; lane 2, DNA incubated with partially purified REase from Ds2-324; lane 3, DNA incubated with partially purified REase from Tur2-TS24; lane 4, DNA incubated with partially purified REase from Sa27-m20; lane 5, DNA incubated with REase from Tur2-TS24 in presence of REase MvaI; lane 6, DNA incubated with REase MvaI; lane M, GeneRuler™ DNA Ladder Mix. "+", DNA of pBR322 is Dam and Dcm methylated; "−", DNA of pSEAd6/BamHI is not methylated.

The current specification describes the discovery, partial purification and characterization of a group of methylation-specific restriction endonucleases of a new type which recognize very short DNA targets containing 5-methylcytosine (m5C) in one DNA strand and cleave both DNA strands at a fixed position outside the recognition sequence. Enzymes of this group cleave the DNA strand which contains m5C preferably twelve nucleotides away from the modified nucleotide to the 3' direction, whereas the opposite DNA strand is cleaved preferably sixteen nucleotides away from the G base, which is complementary to the m5C, to the 5' direction. The double-stranded DNA cleavage results in products with a 5' overhang of four nucleotides. One enzyme of this group is methylation-specific restriction endonuclease SgeI from natural microbial isolate Tur2-TS24, later on identified as *Streptomyces griseoflavus* (strain RFL11), which preferably recognizes the target sequence m5CNNG. The other example of this group is restriction endonuclease SguI from natural microbial isolate Ds2-324, later on identified as *Streptomyces griseus* RFL12, which preferably recognizes the target sequence Cm5C.

*Streptomyces griseus* strain RFL12 was deposited on 19 Feb. 2010 at the Microbial Strain Collection of Latvia under the Budapest Treaty and has been given accession number P930. A sample of *E. coli* GMMG2163 (pUC-Sge1) was deposited on 19 Feb. 2010 at the Microbial Strain Collection of Latvia under the Budapest Treaty and has been given accession number P931. As discussed in further detail below, the pUC-Sge1 construct comprises pUC19NS into the full sequence of Sge1 has been ligated following NotI-SmiI digestion.

There is also described cloning and sequence analysis of gene which codes for SgeI as well as synthesis and purification of SgeI from *E. coli* cells.

Finally, there is described multiple uses of discovered methylation-specific restriction endonucleases, all of which are based on their unique properties. One such described application shows site-specific cleavage of fully- and hemi-methylated circular DNA duplexes, leaving not methylated DNA molecules intact. The other described application demonstrates usage of enzymes of this invention for analysis of the level of global cytosine methylation at $5^{th}$ position. The third described application demonstrates genome-wide analysis of individual 5-methylcytosines. Finally, the fourth described application demonstrates usage of enzymes for whole genome analysis of DNA methylation patterns.

In the experimental disclosure, which follows, the following bacterial strains, plasmids, media, enzymes, kits and markers were used:

Bacterial Strains, Plasmids, Media and Transformation

Tur2-TS24, Ds2-324 and Sa27-m20 are bacterial strains isolated from environmental samples. Tur2-TS24 was identified as *Streptomyces griseoflavus* with assigned collection number RFL11 (*Streptomyces griseoflavus* RFL11), whereas Ds2-324 was identified as *Streptomyces griseus* with assigned collection number RFL12 (*Streptomyces griseus* RFL12). *Escherichia coli* strain DH10B F$^-$ mcrA Δ(mrr-hsdRMS-mcrBC) φ80lacZΔM15 ΔlacX74 recA1 endA1 araD139 Δ(ara, leu) 7697 galU galK λ$^-$ rpsL nupG (Invitrogene) was used as a host for propagation and isolation of plasmids methylated at their Dam and Dcm targets (dam$^+$ dcm$^+$). *Escherichia coli* strain GMMG2163 is identical to the strain GM2163 except that the activity of Dcm has been completely abolished by insertion of tet gene which ensures resistance to tetracycline into dcm-6 gene. The genotype of GMMG2163 is F$^-$ dam-13::Tn9 dcm-6::tet (Tc$^R$) hsdR2 leuB6 hisG4 thi-1 araC14 lacY1 galK2 galT22 xylA5 mtl-1 rpsL136 fhuA31 tsx-78 glnV44 mcrA mcrB1. GMMG2163 was used as a host for propagation and isolation of plasmids which are not methylated at their Dam and Dcm targets (dam$^-$ dcm$^-$) and as a host for cloning and expression of gene coding for active SgeI restriction endonuclease. *Escherichia coli* strain XL1-Blue (F'::Tn10 proA$^+$B$^+$lacI$^q$ Δ(lacZ)M15/recA1 endA1 gyrA96 thi-1 hsdR17 glnV44 relA1 lac) was used as a host for cloning of PCR-amplified fragments of gene coding for 16S rRNA. *Escherichia coli* strain ER2267 (F' proA⁺B⁺ lacI$^q$ Δ(lacZ)M15 zzf::mini-Tn10)/Δ(argF-lacZ)U169 glnV44 e14⁻(McrA⁻) rfbD1? recA1 relA1? endA1 spoT1? thi-1 Δ(mcrC-nmr)114::IS10) from New England Biolabs was used as a cloning host in genome walking and inverse PCR experiments. *Escherichia coli* strain Top 10 (F⁻ mcrA Δ(mrr-hsdRMS-mcrBC) φ80lacZΔM15 ΔlacX74 recA1 araΔ139 Δ(ara-leu)7697 galU galK rpsL endA1 nupG) from Invitrogene was used as a cloning host in experiments used to investigate SgeI specificity and its cleavage properties. pSEAd6 (Fermentas collection) is a multicopy plasmid which contains an inserted fragment of adenovirus-2. pUC19NS (Fermentas collection) is a multicopy expression plasmid which is specially designed for directional cloning of DNA fragments (resulting after the cleavage with SmiI and NotI) very close to the efficient ribosome binding site under the control of plasmid-encoded P$_{lac}$ promoter. DNA of phage λ (dam⁺ dcm⁺), DNA of phage λ (dam⁻ dcm⁻), DNA of phage phiX174 (dam⁺ dcm⁺) and DNAs of pBR322 (dam⁺ dcm⁺) and pUC57 (dam⁺ dcm⁺) are commercial products of Fermentas International. All strains were grown in LB medium containing ampicillin (Ap, 100 mg/l) and/or kanamycin (Km, 50 mg/l) as required. Cells were transformed using the CaCl$_2$-heat shock method (Sambrook, 1989) or by electroporation. Transformants were selected by plating onto LB agar supplemented with appropriate antibiotics. IPTG and X-Gal were added to LB agar following standard procedures (Sambrook, 1989) in cases when blue-white screening was required.

Enzymes, Kits, Markers, Primers

All enzymes, kits, molecular weight markers, primers and other reagents, unless indicated otherwise, were from Fermentas. All enzymatic reactions were performed according to the manufacturer's instructions.

Experimental Outline

Identification of Methylation-Specific Restriction Endonucleases and their Partial Purification Screening of bacterial strains isolated from various environmental samples for those, which produce methylation-specific restriction endonucleases was carried out by incubating crude extracts of strains under investigation with modified (dam⁺ dcm⁺) and not modified (dam⁻ dcm⁻) DNA of phage λ as a substrate in parallel at 37° C. and varying both the amount of crude extract added and the reaction incubation time. After analysis of reaction products by agarose gel electrophoresis at least three bacterial strains, Ds2-324, Tur2-TS24 and Sa27-m20, were identified which digested the modified DNA substrate but not the non-modified one. The activity of methylation-specific restriction endonucleases in crude extracts was hardly detectable (only traces of DNA cleavage were observed after the overnight incubation) and too low for specificity studies; therefore all three enzymes were partially purified following the scheme which was applied for purification of restriction enzyme from Tur2-TS24 (see below) and then, with small modifications, for purification of enzymes from two remaining bacterial isolates (not shown). Partial purification of restriction endonuclease from Tur2-TS24 was done as follows.

13 g of Tur2-TS24 biomass were suspended in 52 ml buffer A (10 mM potassium phosphate buffer, pH 7.0; 1 mM EDTA, 1 mM DTT) containing 0.1 M KCl, and then cells were disrupted by sonication. After sonication, cell debris was removed by centrifugation (0.5 h, 48000×g, 4°C.). The supernatant was subjected to chromatography on a Heparin Sepharose CL-6B column (1×15 cm). Elution was conducted by gradually increasing KCl concentration from 0.1 to 1.0 M in buffer A. Chromatographic fractions, collected during purification, were assayed for restriction endonuclease activity by incubating samples (1 μl) of individual fractions with 1 μg of λ DNA (dam⁺ dcm⁺) substrate at 37° C. for 16 h in Tango™ 1× buffer (commercial product of Fermentas). Reaction products were analyzed by agarose gel electrophoresis. The fractions containing restriction endonuclease activity (eluted at 0.5-0.6 M KCl) were pooled, dialyzed against buffer A which contained 0.1 M KCl, and then loaded onto Q Sepharose® Fast Flow column (1×9 cm). Restriction endonuclease activity was found in flow through fractions. The pooled fractions were directly applied onto Blue Sepharose CL-6B column (1×7 cm), elution from column was conducted by gradually increasing KCl concentration from 0.1 to 1.0 M in buffer A. The fractions, eluted at 0.6-0.7 M KCl, contained restriction endonuclease activity. They were again pooled, dialyzed against Storage buffer (10 mM Tris-HCl, pH 7.5, 100 mM KCl, 1 mM DTT, 0.1 mM EDTA, 0.2 mg/ml BSA and 50% glycerol) and stored at −20° C.

DNA Cleavage Properties of Restriction Endonucleases Partially Purified from Ds2-324, Tur2-TS24 and Sa27-m20

Initial evaluation of DNA cleavage properties of partially purified restriction enzymes from Ds2-324, Tur2-TS24 and Sa27-m20 isolates was carried out using two alternative plasmid DNA substrates, of which one (supercoiled DNA of plasmid pBR322) was in vivo modified at Dam and Dcm targets, while the other one (BamHI-linearized DNA of plasmid pSEAd6)—did not. Activity assays were done using 20 μl of Tango™ 1× buffer which contained 1-2 μl of partially purified preparations of enzymes and 1 μg of substrate DNA. Reactions proceeded 16 h at 37° C., and then reaction products were analyzed by agarose gel electrophoresis. FIG. 1 shows that all three enzymes were not active on non modified substrates. On the other hand, cleavage patterns of the dam⁺ dcm⁺DNA substrate generated by all three partially purified restriction enzymes were identical and resembled that of restriction endonuclease MvaI (FIG. 1, lane 6). The latter recognizes the same DNA sequence as Dcm methyltransferase (CCWGG) and is not sensitive to Dcm-specific methylation. Double digestion with REase from Tur2-TS24 and MvaI resulted in the same DNA cleavage pattern (FIG. 1, lane 5), suggesting that targets of both enzymes completely overlap. Of note, testing of another Dam/Dcm-modified substrate, DNA of phage phiX174 which contains only two Dcm targets, revealed the site-specific cleavage at Dcm targets as well (data not shown). Based on this information it was concluded, that (1) all three enzymes under investigation need modified DNA targets, (2) Dcm-catalyzed modification of the second cytosine (Cm5CWGG) is recognized by all three enzymes, and (3) all Dcm-modified targets are digested, suggesting that recognition sequences of all three enzymes should include only the nucleotide sequences which are within modified Dcm targets.

Figures 2A, 2B:
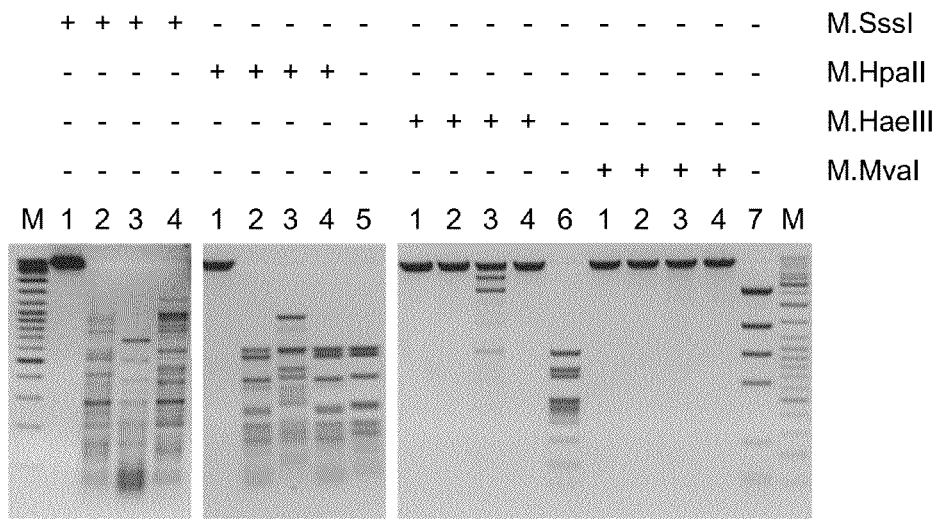
FIG. 2 demonstrates the effect of cytosine methylation type and sequence context on cleavage properties of partially purified restriction endonucleases from Ds2-324, Tur2-TS24 and Sa27-m20. (A) Cleavage patterns of pSEAd6/BamHI pre-methylated with methyltransferases shown on the right of the picture. Lane 1—not cleaved DNA; lane 2, DNA incubated with REase from Ds2-324; lane 3, DNA incubated with REase from Tur2-TS24; lane 4, DNA incubated with REase from Sa27-m20; lane 5, DNA incubated with REase HpaII; lane 6, DNA incubated with REase HaeIII; lane 7, DNA incubated with REase MvaI; lane M, GeneRuler™ DNA Ladder Mix. (B) Summary of cleavage experiments.

In order to shed more light on sequence- and substrate specificity of isolated methylation-dependent restriction endonucleases, DNA (dam⁻ dcm⁻) of BamHI-linearized pSEAd6 was in vitro modified at specific targets using four different cytosine-specific methyltransferases (MTases) and incubated with restriction enzymes under investigation (FIG. 2A) following conditions described above. Three out of four explored MTases are m5C-specific (M.HpaII, M.SssI and M.HaeIII), while the last one, MvaI, modifies the second cytosine within the CCWGG target like Dcm, but, in contrast to Dcm, yields m4C instead of m5C (FIG. 2B). The completeness of methylation reactions was evaluated by incubating the modified DNA substrates with cognate restriction endonucleases which are sensitive to the introduced modification; the absence of DNA cleavage was assumed as an indication of complete methylation (data not shown). FIG. 2A shows that all three enzymes act on M.SssI-modified DNA and have a lot of recognition targets on this substrate, resulting in a smear of DNA fragments. Methylation by M.HpaII creates targets for all three REases as well. However, in the case of M.HpaII-modified DNA substrate cleavage patterns of two types were observed. Enzymes isolated from Ds2-324 and Sa27-m20 generated the same set of DNA products, which resembled the pattern of HpaII-cleaved DNA fragments (FIG. 2A, compare lanes 2 and 4 with lane 5), while the pattern of DNA fragments resulting after the cleavage with enzyme from Tur2-TS24 was different (lane 3). In case of M.HaeIII-modified DNA substrate enzymes from Ds2-324 and Sa27-m20 were unable to cleave the substrate, while enzyme from Tur2-TS24 produced several cleavage products. Finally, all tested enzymes had no activity of M.MvaI-modified DNA substrate. Based on these and previous results it was concluded that: (1) m5C, but not m4C is recognized by all three enzymes; (2) enzymes from Ds2-324 and Sa27-m20 recognize and cleave all M.HpaII-modified targets, suggesting that recognition sequences of these two enzymes should include only those sequences which are within modified M.HpaII targets; (3) among tested, there are at least two different specificities of enzymes acting on modified DNA. One specificity is exhibited by enzyme isolated from Tur2-TS24, the other one—by enzymes isolated from Ds2-324 and Sa27-m20; (4) the information is not enough to predict either enzymes from Ds2-324 and Sa27-m20 posses identical, or different, specificity.

Further experiments were carried out with a pair of methylation-specific restriction enzymes which exhibited clearly different specificities, namely REases from bacterial isolates Tur2-TS24 and Ds2-324.

Characterization of Bacterial Isolates Tur2-TS24 and Ds2-324

0.2 ml of fresh overnight cultures of bacterial isolates Tur2-TS24 and Ds2-324 were used for isolation of their genomic DNAs using Genomic DNA Purification Kit (Fermentas). The taxonomic identification of bacterial isolates Tur2-TS24 and Ds2-324 was based on analysis of their genes coding for 16S rRNA. PCR amplification of 16S rRNA genes using genomic DNAs as templates and primers w001 (AGTTTGATCMTGGCTC (SEQ ID No: 19)) and w002 (GNTACCTTGTTACGACTT (SEQ ID No: 20)) was done following Godon et al. (Godon et al., 1997). In order to avoid the impact of accidental PCR-generated point mutations on results of taxonomic identification, three parallel polymerase chain reactions were carried out in case of both strains. The cloning of amplification products of ~1450 bp in length was done using the InsTAclone™ PCR cloning kit (Fermentas), sequencing of isolated recombinant plasmids—using CycleReader™ Auto DNA Sequencing Kit and Cy5 labelled primers: M13/pUC Sequencing Primer (−46), 22-mer, and M13/pUC Reverse Sequencing Primer (−46), 24-mer (Fermentas). Sequencing data were collected on ALFexpressII (Amersham Pharmacia Biotech), alignment of sequences was done using ClustalW program (Larkin et al., 2007), similarity searches were performed using the BLAST program (Altschul et al., 1990). Comparison of sequences revealed the similarity of 99% between the DNA fragment amplified from Tur2-TS24 and the sequence of 16S rRNA gene from *Streptomyces griseoflavus*. Based on this information Tur2-TS24 was identified as *Streptomyces griseoflavus*, strain RFL11, and methylation-specific restriction endonuclease was named SgeI. Likewise, similarity of 99% was found between the DNA fragment amplified from Ds2-324 and the sequence of 16S rRNA gene from *Streptomyces griseus*. Therefore, Ds2-324 was identified as *Streptomyces griseus*, strain RFL12, and methylation-specific restriction endonuclease was named SguI.

Cloning and Expression of Gene Coding for SgeI

Cloning and expression experiments were done in several subsequent steps, which are described below.

Figures 3A, 3B, 3C:
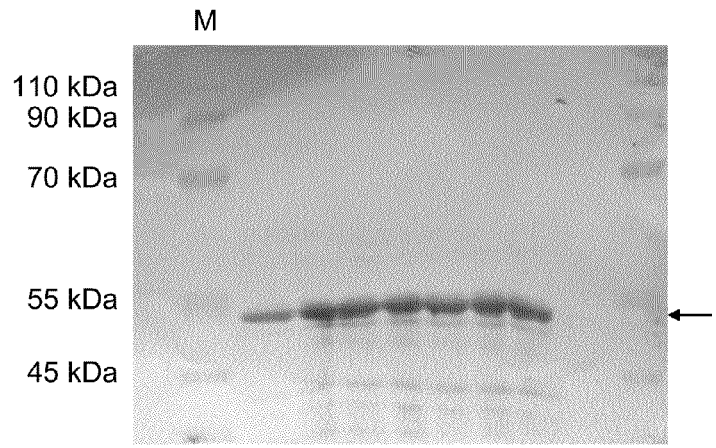
FIG. 3 shows the membrane which was used as a source of protein for N-terminal sequencing of the presumable REase SgeI from Streptomyces griseoflavus RFL11 and the design of primers used for cloning of respective gene. (A) Coomassie blue—stained membrane which was used for N-terminal sequencing of the most abundant protein (shown by arrow) present within the partially purified preparation of SgeI. Lane M, Prestained protein ladder, 10-160 kDa; (B) the N-terminal sequence (SEQ ID No: 5, shown as black letters on a grey background; "/" stands for no signal, amino acid abbreviations in parenthesis show weak or uncertain signal) determined after 26 cycles of Edman degradation, and nucleotide sequences of degenerate PCR primers which were designed based on the identified amino acid sequence (Turbt (SEQ ID No: 4); TurN1 (SEQ ID No: 6); and TurN2 (SEQ ID No: 7)). Letter "Y" stands for C or T, "R"—for G or A, "N"—for G, A, T or C; (C) sequences of primers used for genome walking (WP1 (SEQ ID No: 8); WP2 (SEQ ID No: 9); WP3 (SEQ ID No: 10); WP4 (SEQ ID No: 11); and WP5 (SEQ ID No: 12)).

Identification of the N-Terminal Amino Acid Sequence of Presumable SgeI Restriction Endonuclease Approximately 300 µl of partially purified preparation of SgeI was applied to seven lanes of SDS-polyacrylamide (8%) gel and subjected to electrophoresis. Fractionated proteins were then electroblotted to a PVDF membrane (Immunoblot P, Sigma) at 50V, 100 mA for 30 min. The membrane was stained with Coomassie Blue R-250 in 40% MeOH/1% acetic acid. One major band of ~50 kDa and several bands of other, smaller proteins were observed on the dried membrane (FIG. 3A). Based on comparison of results of SDS-PAGE analysis of proteins in individual chromatographic fractions with the presence or the absence of restriction endonuclease activity within these fractions (data not shown), the presumption was made that the most abundant protein may be the restriction endonuclease SgeI. All subsequent experiments, shown in this chapter, were dedicated for testing of this hypothesis. The membrane was used for N-terminal sequencing of the most abundant protein shown in FIG. 3A by arrow, expecting to use gathered sequence information for gene cloning purposes. Sequencing was performed in ZMMK Servicelabor (Köln, Germany). Twenty six cycles of Edman degradation resulted in amino acid sequence shown in FIG. 3B (black letters on a grey background).

Directional Genome Walking Experiments

Figure 4A:
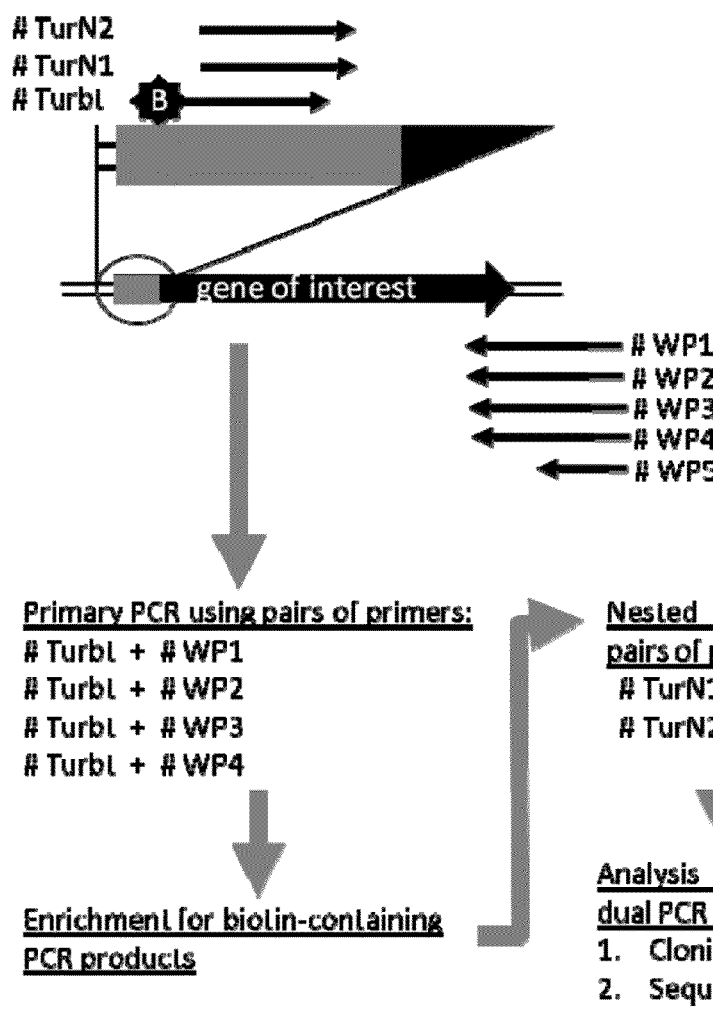
FIG. 4 illustrates the genome walking experiment used to clone the 5'-terminal region of gene coding for presumable REase SgeI (A) and shows patterns of PCR fragments obtained after nested PCRs (B). Primary PCR products served as templates for nested PCR. The nested PCR products which were chosen for further analysis are shown by white arrows and marked by letters. Lane M, GeneRuler™ DNA Ladder Mix.

Protein sequence-based gene cloning techniques require the amino acid sequence of good quality which is long enough to design appropriate amplification primers. Unfortunately, only 11 contiguous and unambiguously characterized amino acid residues were identified in case of presumable SgeI restriction endonuclease (FIG. 3B, the sequence YAKT-KDPSNEV (SEQ ID No: 21)), reducing the region suitable for designing of primers down to 33 nucleotides (11 amino acid residues×3 nt). Cloning of DNA fragment which encodes the identified amino acid sequence was carried out following the method of directional genome walking which is based on the use of two steps of PCR and a set of primers of special design (Mishra et al., 2002). For primary PCR a sequence-specific degenerate biotinylated primer (# Turbt; FIG. 3B and FIG. 4A) was used along with four different walker primers (# WP1 through # WP4), differing from each other by four nucleotides at their very 3'-ends (FIG. 3C). Products of four parallel amplification reactions were enriched for DNA fragments which contain biotin label using paramagnetic streptavidin-coated beads, and then used as templates for nested PCR using two primers, one of which is locus-specific (# TurNI or # TurN2; FIG. 3B and FIG. 4A) and the other one is a universal walking primer # WP5 which corresponds to the common 5'-terminal part of walker primers used in primary PCR (FIG. 3C and FIG. 4A). Of note, the reason of appearance of two alternative sequence-specific primers (# TurNI or # TurN2) in nested PCR is the existence of two types of codons (TCN and AGY) that are able to encode Serine. All primers used were synthesized at MWG Biotech. Details of genome walking experiment are described below.

To prepare large amount of *Streptomyces griseoflavus* RFL11 genomic DNA, 1 g of cell paste was resuspended in 10 ml of 50 mM Tris-HCl, 10 mM EDTA (pH 8). Then 1 ml of 2 mg/ml lysozyme in 50 mM Tris-HCl, 10 mM EDTA (pH 8) was added and incubated for 60 minutes at 37° C. After that SDS was added to the final concentration of 1%, and suspension was left at 37° C. for additional 90 minutes. The mixture was then extracted with phenol and twice with phenol-chloroform, and DNA was precipitated by adding NaCl to 0.2 M and layering 1 volume of isopropyl alcohol on top. The precipitated DNA was spooled onto a glass stick, washed with 75% ethanol for 1 hour, than dried for 30 minutes at room temperature and dissolved in 2 ml of water to a final concentration of approx. 500 µg/ml.

Primary PCR (FIG. 4A) was carried out using approx. 1 µg of S. griseoflavus RFL11 genomic DNA as a template in 100 µl of reaction mixture containing 7.5 units of recombinant Taq polymerase, pairs of primers shown in FIG. 4A, Taq buffer with $(NH_4)_2SO_4$, dNTPs at 0.3 mM concentration and varying $MgCl_2$ concentration (from 2 mM to 8 mM). The concentration of primers was different—0.2 µM for #Turbt and 1 µM for #WP1-WP4. Cycling conditions were as follows: initial denaturation at 94° C. for 4 min, and then 30 cycles of denaturation at 94° C. for 1 min, annealing at 47° C. for 1 min and extension at 72° C. for 4 min.

Primary PCR products were immobilized on streptavidin-linked paramagnetic beads (Dynabeads kilobase BINDER™ kit, Dynal) following recommendations of manufacturer. The non bound DNA was washed off 3 times using Taq buffer with $(NH_4)_2SO_4$.

Figure 4B:
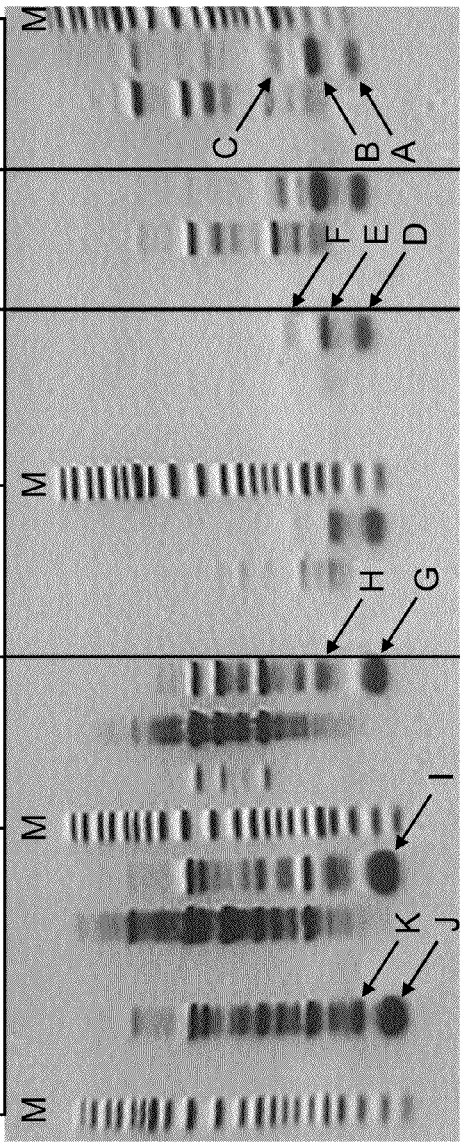

Nested PCR was carried out using 2 µl of immobilized primary PCR products as templates along with pairs of primers #TurN1/#WP5 and #TurN2/#WP5 (FIG. 4A). In order to distinguish between PCR products which are generated from individual primers and those DNA fragments which appear as a result of synthesis from two different primers, polymerase chain reactions omitting one of two primers were carried out in parallel as controls. The concentration of all primers was 1 µM, while cycling conditions were the same as used in primary PCR. Amplification products were analyzed by electrophoresis in 1% agarose gel (FIG. 4B). Eleven amplification products (FIG. 4B, A to K) in range between 100 and 500 base pairs were chosen for cloning experiments.

Selected DNA fragments were gel-purified using Silica Bead DNA Gel extraction Kit and cloned using InsTAclone™ PCR cloning kit. Competent ER2267 cells were transformed with ligation mixtures using the $CaCl_2$-heat shock method and spread onto LB-agar plates supplemented with ampicillin. Plates were incubated overnight at 37° C. Colonies of several transformants from each transformation were picked by sterile toothpicks and used as templates in PCR using standard primers: M13/pUC sequencing primer (–46), 22-mer and M13/pUC reverse sequencing primer (–46), 24-mer. PCR products were visualized on a 1% agarose gel. In case when the size of PCR-amplified DNA fragment matched the expected one, the PCR product was directly sequenced using standard primers. At least three independent PCR products of appropriate size from each ligation/transformation reaction were sequenced. However, analysis of more than 30 determined nucleotide sequences revealed only two overlapping DNA fragments (B-8, 396 bp long, and H-35, 334 bp long) which had a potential to encode the sequenced N-terminal part of presumable SgeI restriction endonuclease.

Cloning and Analysis of Missing Parts of Gene Coding for Presumable SgeI Restriction Endonuclease Cloning of missing parts of gene of interest was based on nucleotide sequence information of the B-8 fragment (396 bp) and followed the inverse PCR approach (Ochman et al., 1988). Two outward primers (R1T and D1T), annealing close to ends of the known nucleotide sequence, were designed and used in inverse PCR:

| R1T | 5'-GTTACGTGCCAAAAGTTCGG | (SEQ ID No: 22) |
| D1T | 5'-GTGTGTTGGCAGAACCGTTG | (SEQ ID No: 23) |

To provide the template for inverse PCR, genomic DNA of S. griseoflavus RFL11 (~10 µg) was completely digested in parallel reactions with RsaI and with AluI (both enzymes do not have recognition targets within the known DNA sequence). Then REases were heat-inactivated, reaction products were diluted with T4 DNA ligase buffer to the final concentration of 2 µg per ml and circularized by incubating DNA fragments overnight at room temperature in presence of T4 DNA ligase.

Inverse polymerase chain reactions were carried out using 2 µl of either RsaI or AluI ligation reaction mixtures as templates in 50 µl of Taq buffer containing 2 mM $MgCl_2$, 0.2 mM dNTPs, 5% DMSO, 1 µM of primers R1T and D1T and 2.5 units of Taq polymerase. PCR conditions were as follows: initial denaturation at 94° C. for 4 min, and then 30 cycles of denaturation at 94° C. for 45 sec, annealing at 55° C. for 45 sec and extension at 72° C. for 4 min. Amplification products were analyzed by electrophoresis on a 1% agarose gel. The 0.8 kb fragment, amplified using AluI-digested and self-ligated DNA fragments as a template, was gel-purified using Silica Bead DNA Gel extraction Kit and cloned using InsTAclone™ PCR cloning kit. Transformation and analysis of individual clones was carried out as described in previous section. Two recombinant plasmids were purified following the slightly modified method of Birnboim and Doly (1979), and cloned DNA fragments of 0.8 kb were sequenced using M13/pUC sequencing primer (–46), 22-mer and M13/pUC reverse sequencing primer (–46), 24-mer. The newly determined nucleotide sequence was compared with the already known sequence, and then both sequences were merged into one 1154 bp contig. Analysis of contig for open reading frames (ORFs) revealed a large ORF which was 1116 bp long, encoded a protein starting with the amino acid sequence which matched perfectly the sequence determined during Edman sequencing (FIG. 3B), but missed the 3' terminal part. In order to identify the missing 3'-terminal region of identified ORF, a new pair of outward primers, annealing close to the 3'-end of ORF under investigation, was synthesized for inverse PCR purposes:

| d2T | 5'-CGTCACGACCGGATCCTTC | (SEQ ID No: 24) |
| r2T | 5'-CCGCGACGCAGACGAGCC | (SEQ ID No: 25) |

Preparation of circular templates of genomic DNA for inverse PCR followed the scheme described above, with the exception that REases Cfr10I, Hin1I, MbiI, MluI and EheI were used instead of RsaI and AluI. Set-up of inverse PCR also followed the above-described scheme, with the exception that a new pair of primers, d2T and r2T, was used. Amplification products were analyzed by electrophoresis on a 1% agarose gel. Polymerase chain reaction using Hin1I-cleaved and self-ligated genomic DNA resulted in appearance of DNA fragment of 1.2 kb in size, while amplification with EheI-cleaved and self-ligated DNA as a template resulted in synthesis of a DNA fragment of 0.8 kb. Both DNA fragments were purified, cloned and sequenced following techniques described above. The nucleotide sequence of 1174 bp, determined after the sequencing of cloned DNA fragment of 1.2 kb, was compared with the already known sequence, and then both sequences were merged into one 2132 bp contig. The contig encompassed the full-length ORF (1305 bp in length) and adjacent downstream region. The open reading frame encoded a protein of 434 amino acid residues with the calculated mass of 48.5 kDa, the latter being in good agreement with the mass of protein used for N-terminal sequencing (FIG. 3A). In addition, the sequence of 27 N-terminal amino acid residues of the encoded protein (MTKWLRIGQVLRY-AKTKDPSNEVEGGF (SEQ ID No: 26)) matched perfectly the amino acid sequence determined during protein sequencing (FIG. 3B), clearly indicating that the identified ORF codes for a sequenced protein and may be a sgeIR gene. However, the final contig was generated by merging sequences of several independently cloned overlapping DNA fragments. Therefore cloning and expression of the full-length gene was necessary to answer the question if the sequenced protein indeed is methylation-specific restriction endonuclease SgeI.

Cloning of the Full-Length Presumable sgeIR Gene

A pair of PCR primers of special design was synthesized for cloning purposes:

```
                                            (SEQ ID No: 27)
    Turpr      5'-TATTTAAATGACCAAATGGTTGCGGATC (SEQ ID No: 28)
    Turgal     5'-TGCGGCCGCCAAGCTCAGTCGGACGA
```

The Turpr primer anneals to the 5' end of presumable sgeIR gene, contains the introduced target for SmiI REase (underlined) and translation initiation codon ATG (boxed), whereas Turgal anneals downstream of the translation termination codon of sgeIR and contains NotI target (underlined).

In order to prevent the cleavage of intracellular Dcm-modified DNA in cells expressing the active SgeI REase, the *E. coli* strain GMMG2163 with the knock down dcm gene was used as a host for cloning and expression.

Verification of the nucleotide sequence of presumable sgeIR gene was done by three parallel amplifications of the 5' part of the gene (Turpr and r2T primers; fragment length 1096 bp) and three parallel amplifications of the 3' part of the gene (Turgal and D1T primers; fragment length 930 bp), in all cases using DNA of *S. griseoflavus* RFL11 as a template. Amplified DNA fragments were cloned and sequenced following procedures described above, and then all collected sequences were compared internally and with the previously determined sequence. After computational analysis of all sequencing data the final nucleotide sequence of the full-length gene of 1305 bp (termination codon included) was established.

PCR amplification (reaction volume—100 µl) of the full-length gene was carried out using approx. 0.5 µg of *S. griseoflavus* DNA, 1 µM of primers Turpr and Turgal, Taq buffer with $(NH_4)_2SO_4$, 2 mM $MgCl_2$, 0.2 mM dNTPs and 5 units of High Fidelity PCR Enzyme Mix. PCR conditions were as follows: initial denaturation at 94° C. for 4 min, and then 25 cycles of denaturation at 94° C. for 45 sec, annealing at 55° C. for 45 sec and extension at 72° C. for 2 min for 25 cycles. The amplified DNA fragment of 1.2 kb was purified from agarose gel using Silica Bead DNA Gel extraction Kit and cloned using InsTAclone™ PCR cloning kit. Transformation of competent GMMG2163 cells, analysis of individual colonies for recombinant plasmids as well as their isolation followed procedures described above. Inserted fragments of four isolated plasmids were sequenced using standard sequencing primers (M13/pUC sequencing primer and M13/pUC reverse sequencing primer) as well as two internal primers D1T and r2T which have been used in cloning experiments (see above). Sequence analysis revealed that one recombinant plasmid contains a presumable sgeIR gene of correct structure.

Expression of sgeIR

In order to place cloned gene under the control of $P_{lac}$, the plasmid which contains the sgeIR gene of correct structure was digested with SmiI and NotI, and the resulting fragment of 1.3 kb was ligated to the NotI-SmiI digested and phosphatase-treated expression plasmid pUC19NS. Ligation mixture was used to transform competent cells of GMMG2163. Recombinant plasmids of correct structure were identified by restriction mapping, and two clones harboring these plasmids were cultivated overnight in a small volume of LB medium supplemented with ampicillin. The cells were thereafter harvested by centrifugation and disrupted by sonication to produce a crude cell extract. Incubation of a sample of crude cell extract with the Dcm-modified substrate DNA revealed the presence of substantial amount of SgeI activity, confirming that the cloned gene codes for SgeI restriction endonuclease. In order to provide biomass for pilot-scale purification experiments, one clone was grown in 5 l of LB overnight, and harvested biomass (13 grams) was used for purification of recombinant SgeI.

Purification and DNA Cleavage Properties of Recombinant SgeI

The obtained biomass (13 grams) was suspended in 52 ml of buffer A (10 mM potassium phosphate buffer, pH 7.0; 1 mM EDTA, 1 mM DTT) containing 0.1 M KCl, and then cells were disrupted by sonication. The cell debris was removed by centrifugation (0.5 h, 48000×g, 4° C.). The crude extract was subjected to chromatography on a Heparin Sepharose CL-6B column (1.6×14 cm) pre-equilibrated with buffer A containing 0.1 M KCl. 72 ml of wash buffer A, containing 0.1 M KCl, was applied and then 240 ml of buffer A with gradient of KCl from 0.1 to 1 M was loaded onto the column. Fractions, collected during all purification steps, were assayed for SgeI activity by incubating sample (1 µl) of individual fraction (10-fold diluted in buffer A with 0.1 M KCl) with 1 µg of Dam/Dcm-modified pBR322 DNA as a substrate at 37° C. for 5 minutes in 30 µl buffer containing 10 mM Tris-HCl (pH 8.5 at 37° C.), 10 mM $MgCl_2$, 100 mM KCl and 0.1 mg/ml BSA. Reaction products were analyzed by agarose gel electrophoresis. Fractions after Heparin Sepharose CL-6B column containing SgeI activity (eluted at 0.55-0.65 M KCl) were pooled, dialyzed against buffer A (supplemented with 0.1 M KCl) and then loaded onto Blue Sepharose CL-6B column (1.6×10 cm) pre-equilibrated with buffer A containing 0.1 M KCl. 54 ml of wash buffer A, containing 0.1 M KCl, was applied, and then 180 ml of buffer A with gradient of KCl from 0.1 to 1 M was loaded onto the column and individual fractions of eluate were collected. Fractions containing SgeI activity (eluted at 0.4-0.5 M KCl) were pooled, dialyzed against buffer A containing 0.1 M KCl and then loaded onto Phosphocellulose P11 column (1×14 cm) pre-equilibrated with buffer A which contains 0.1 M KCl. 22 ml of wash buffer A, containing 0.1 M KCl, was applied, and then 110 ml of buffer A with gradient of KCl from 0.1 to 1 M was loaded and fractions were collected. Fractions with SgeI activity (eluted at 0.6-0.7 M KCl) were dialyzed against Storage buffer (10 mM Tris-HCl, pH 7.5, 100 mM KCl, 1 mM DTT, 0.1 mM EDTA, 0.2 mg/ml BSA and 50% glycerol) and stored at −20° C. In order to evaluate the activity of purified SgeI, decreasing amount of serially diluted SgeI preparation was incubated with 1 mg of Dam/Dcm methylated DNA of pBR322 for 1 h at 37° C. in 50 µl of reaction buffer: 10 mM Tris-HCl (pH 8.0), 5 mM $MgCl_2$, 100 mM KCl, 0.02% Triton X-100, 0.1 mg/ml BSA. One unit is defined as an amount of SgeI at which no change in the fragmentation pattern is observed with further increase of enzyme. The yield of recombinant SgeI obtained following the above-described scheme was found to be approx. 60 000 units per 1 gram of biomass.

Figure 5:
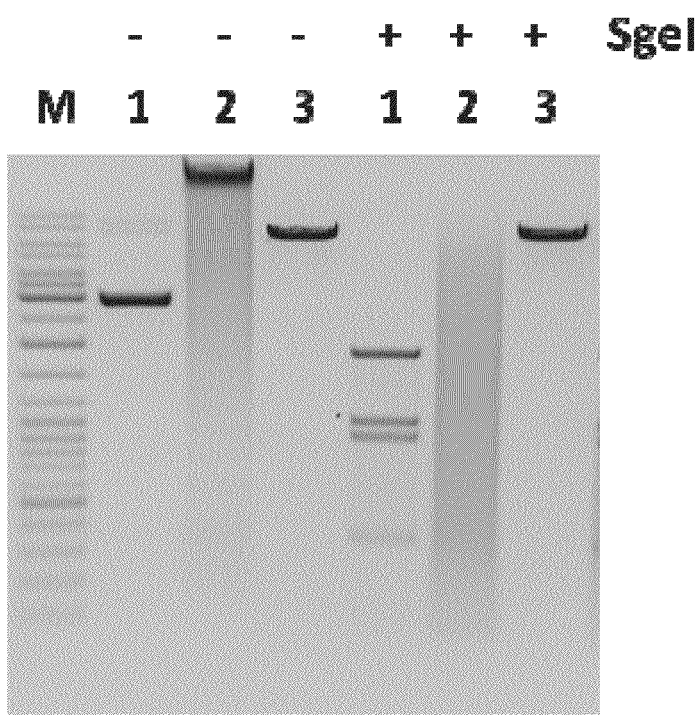
FIG. 5 shows DNA cleavage properties of recombinant SgeI purified from E. coli cells. Lane 1, Dam and Dcm methylated DNA of plasmid pBR322; lane 2, human genomic DNA isolated from blood; lane 3, not methylated DNA of pSEAd6/BamHI; lane M, GeneRuler™ DNA Ladder Mix. "+", SgeI restriction endonuclease added; "−", SgeI not added.

DNA cleavage properties of purified recombinant SgeI were assayed using 20 µl of reaction buffer (described above) which contained 3 units of SgeI restriction enzyme and 1 mg of one out of three types of substrates: Dam and Dcm methylated DNA of pBR322, not methylated and BamHI-linearized DNA of plasmid pSEAd6 or human genomic DNA isolated from blood cells. Reactions were incubated for 1 h at 37° C. and then analyzed by agarose gel electrophoresis. FIG. 5 shows that the purified SgeI enzyme has no detectable activity on non modified DNA substrate (lane 3), completely cleaves the Dam/Dcm modified substrate (lane 1) and produces multiple DNA fragments of genomic DNA isolated from blood cells (lane 2).

Figure 6:
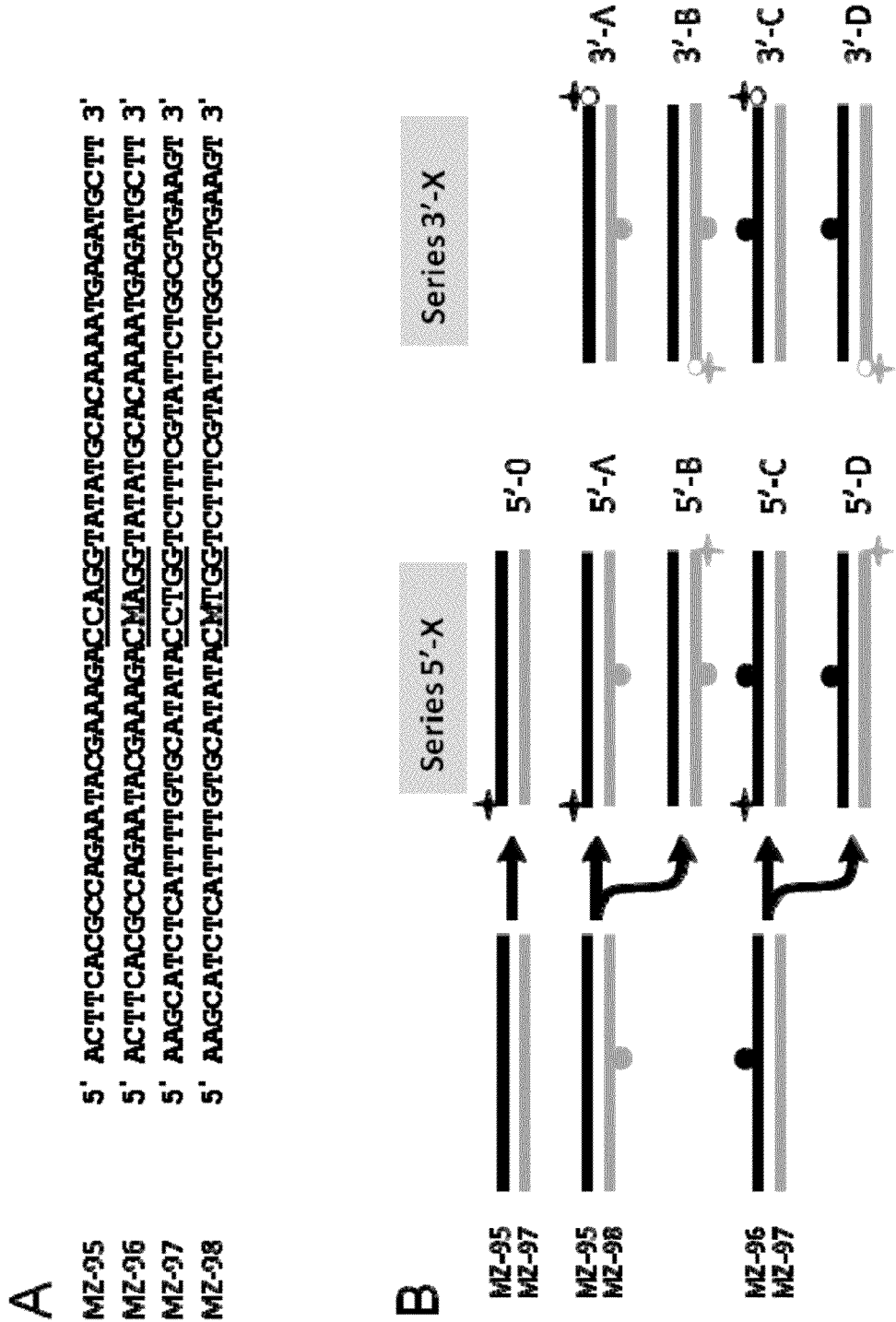
FIG. 6 shows sequences and structures of synthetic oligonucleotides used to determine the exact cleavage position of recognized methylated DNA targets. (A) nucleotide sequences of top-strand oligonucleotides MZ-95 (SEQ ID No: 13) and MZ-96 (SEQ ID No: 14) and bottom-strand oligonucleotides MZ-97 (SEQ ID No: 15) and MZ-98 (SEQ ID No: 16). The sequence CCWGG recognized by Dcm is underlined, "M" shows the position of m5C; (B) structures of oligoduplexes which were radiolabeled either at their 5' ends (Series 5'-X) or at their 3' ends (Series 3'-X). The 4-point star shows the position of radioactive label, filled circle marks the position of m5C, open circle—an extra nucleotide added during the 3'-end labeling.

Determination of Position of DNA Breaks Introduced by Discovered Methylation-Specific Restriction Endonucleases As mentioned previously, SgeI, SguI and restriction endonuclease from bacterial isolate Sa27-m20 digested Dcm-methylated DNA of pBR322 (FIG. 1) and phage phiX174 (data not shown) efficiently at all Dcm targets. In order to answer the question about methylation requirements and cleavage positions of all three enzymes, a set of oligonucleotides of 51 nt in length, containing a unique Dcm target CCWGG at a central position and identical to the phiX174 nucleotide sequence from nt position 3477 to nt position 3527 was synthesized at Metabion GmbH, Germany (FIG. 6A). Of these, one out of two top-strand primers and one out of two bottom strand primers contained a single 5-methylcytosine at the second position of Dcm target (MZ-96 and MZ98, respectively), allowing generation of all possible variants of double-stranded DNA. All four oligonucleotides were additionally size-purified by electrophoresis in 1×TBE buffer using denaturing 8% polyacrylamide gel (8M urea). The elution from gel slices was accomplished by their incubation in water at 37° C. for 16 hours followed by extraction with chloroform-ethanol. The oligonucleotides were labeled either at their 5' ends using T4 polynucleotide kinase and [γ-$P^{33}$]ATP from Hartmann analytic GmbH (Germany) or at their 3' ends by incorporating labeled nucleotide 3'-[α-$^{32}$P]-Cordycepin 5'-triphosphate from PerkinElmer Inc. (USA) using terminal deoxynucleotidyl transferase following standard protocols.

Figure 7A:
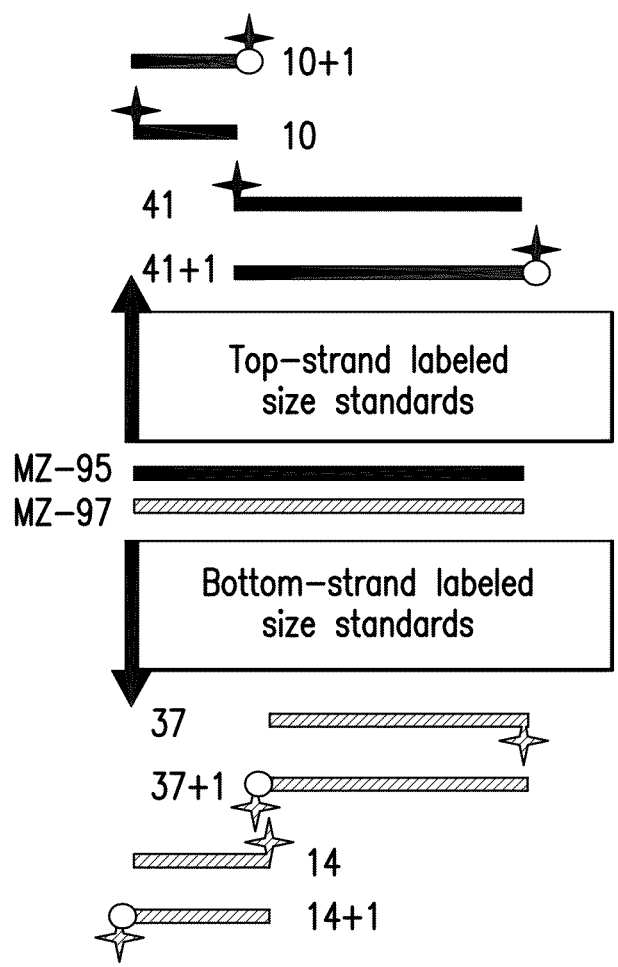
FIG. 7 demonstrates identification of cleavage positions of SgeI and partially purified restriction endonucleases from Streptomyces griseus RFL12 (SguI) and Sa27-m20. (A) structure and length (in nucleotides) of single-stranded oligonucleotides which were labeled either at their 5' ends (10, 14, 37 and 41) or 3' ends (10+1, 14+1, 37+1 and 41+1) and used as size standards. The 4-point star shows the position of radioactive label, open circle marks the extra nucleotide added during the 3'-end labeling; (B) cleavage patterns of double-stranded, 5'-labeled oligoduplexes 5'-0, 5'-A, 5'-B, 5'-C and 5'-D resulting after their incubation with SgeI or restriction enzymes from strains shown above the gel picture (refer to FIG. 6 for detailed structure of substrates used). Lane S, size standards shown in (A) part of the figure. Dotted arrow shows DNA fragment resulting after SgeI cleavage at alternative position shifted by 1 nt; (C) cleavage patterns of double-stranded, 3'-labeled oligoduplexes 3'-A, 3'-B, 3'-C and 3'-D; (D) SgeI cleavage positions within the top and the bottom strand of double-stranded DNA substrates possessing m5C within the bottom strand (oligoduplex MZ-95/MZ-98 (SEQ ID No: 13/SEQ ID No: 16)) or within the top strand (oligoduplex MZ-96/MZ-97 (SEQ ID No: 14/SEQ ID No: 15)). "M" shows the position of m5C. Dotted arrow shows the position of alternative cleavage observed in case of substrates 5'-D and 3'-D.
Figure 7C:
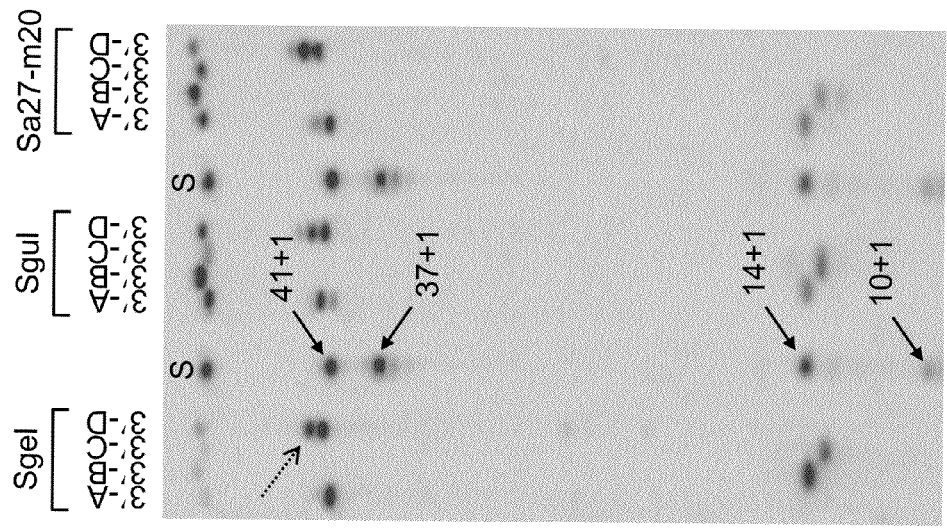
Figure 7B:
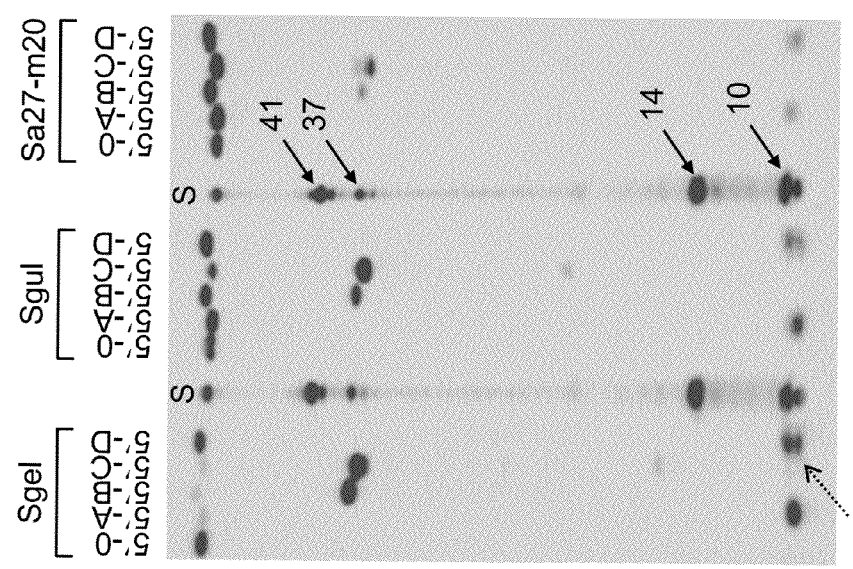
Figure 7D:
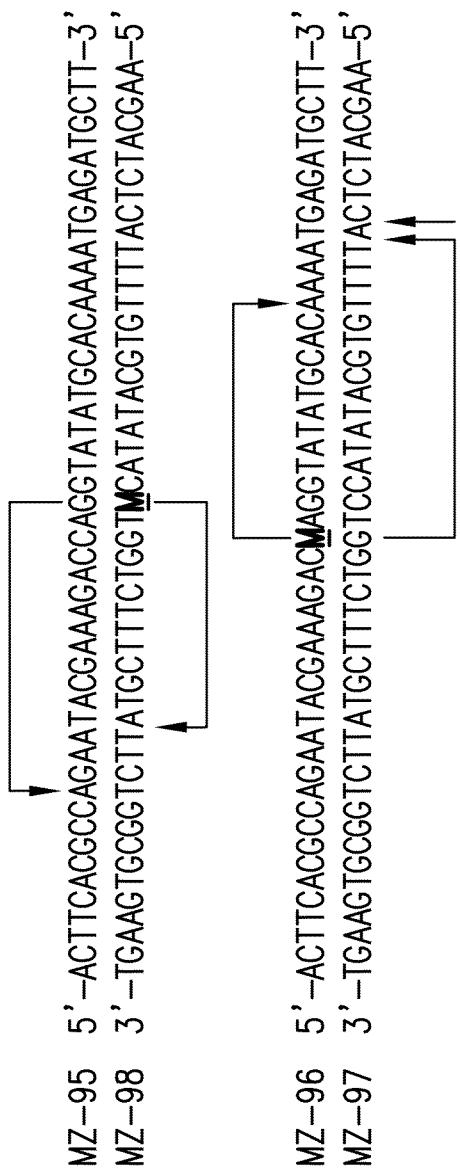

Radiolabeled double-stranded DNA substrates shown in FIG. 6B were prepared by mixing 100 pmol of individual not labeled top-strand and bottom-strand oligonucleotides with 1 pmol of specifically labeled oligonucleotide in 20 µl of water. Annealing of complementary oligonucleotides was accomplished by heating the mixture to 95° C. in a beaker of water and then allowing the beaker to cool to the room temperature. Two series of labeled substrates were constructed (FIG. 6B): 5'-X series encompassed non methylated and hemi-methylated DNA substrates labeled at their 5'-ends, whereas all DNA substrates from 3'-X series were hemi-methylated and labeled at their 3' ends. Of note, the mobility of single-stranded oligonucleotides in denaturing polyacrylamide gels depends not only on their length, but also on their nucleotide composition and sequence. Therefore, after preliminary analysis of cleavage products a set of single-stranded oligonucleotides corresponding to particular cleavage products of top or bottom strand of known size was synthesized at Metabion, labeled either at their 5' ends or at their 3' ends and then used as size standards (FIG. 7A).

Cleavage assays were performed by combining the prepared labeled oligoduplex (500 nM) with endonuclease under investigation (3 units of SgeI, 2 µl of SguI and 2 µl of partially purified REase from bacterial isolate Sa27-m20) in 10 µl of reaction buffer containing 10 mM Tris-HCl (pH 8.0), 5 mM $MgCl_2$, 100 mM KCl, 0.02% Triton X-100 and 0.1 mg/ml BSA in case of SgeI, or in 10 µl of reaction buffer containing 10 mM Tris-HCl (pH 8.5 at 37° C.), 10 mM $MgCl_2$, 100 mM KCl and 0.1 mg/ml BSA in case of two other enzymes. The reactions were incubated at 37° C. either for 60 min (SgeI) or for 16 hours (SguI and REase from Sa27-m20) and terminated by adding 10 µl of STOP solution followed by incubation at 95° C. for 3 min and then by chilling of reaction mixtures in an ice-water bath. The samples were loaded onto 8% polyacrylamide gel containing 8 M urea and 1×TBE. Following electrophoresis, the glass-bound gel was soaked in 10% acetic acid solution for 10 min and then washed out in flawing water for 5 min. The gel was then dried under a hot air stream and radioautographed using the Typhoon™ Trio variable mode imager from GE Healthcare Inc. (USA).

FIG. 7 shows reaction products resulting after the cleavage of 5'-labeled DNA substrates (FIG. 7B) or 3'-labeled DNA substrates (FIG. 7C) with all three REases under investigation. As expected, the m5C-free DNA substrate (FIG. 7B, lane 5'-0) was not cleaved by methylation-specific REases and remained intact. In contrast, both strands of all hemi-methylated DNA substrates were cleaved. In case of SgeI the double-stranded cleavage was nearly complete in case of all tested hemi-methylated substrates except 5'-D, whereas the activity of two other enzymes was extremely low and they were able to cleave only a small fraction of substrates despite very long reaction incubation time (16 h). SgeI results shown in FIGS. 7B and 7C allowed to determine the exact cleavage position in both strands of two substrates differing in m5C location (FIG. 7D). In both substrates the enzyme generated a break in modified DNA strand exactly 12 nucleotides away from m5C, resulting in a single product band in case of substrates 5'-B and 3'-B (m5C located in bottom DNA strand) or in case of substrates 5'-C and 3'-C (m5C located in top strand). However, the cleavage of m5C-free DNA strand of hemi-methylated substrates was not so uniform. In all substrates SgeI disrupted m5C-free DNA strand 16 nucleotides away from G base which is complementary to the m5C, but in case of 5'-D and 3'-D substrates (m5C located in top strand) an additional cleavage position which is shifted by one nt was observed (shown as dotted arrow in FIGS. 7B, 7C and 7D), suggesting that the nucleotide sequence context may have some impact on cleavage variability. Analysis of cleavage products of two other enzymes revealed that both of them share DNA cleavage properties with SgeI. In all cases cleavage products of the same size as those seen in case of SgeI can be identified, suggesting that both enzymes cleave two strands of hemi-methylated DNA substrates 12/16 nucleotides away from m5C like SgeI. However, in case of SguI and partially purified REase from bacterial isolate Sa27-m20 additional bands of products are visible, especially in case of 3'-modified substrates (FIG. 7C). This phenomenon could be explained by the presence of minute amounts of contaminating exonucleases in preparations used, however, the possibility can't be excluded that variable cleavage is intrinsic property of these two enzymes. Based on experiments of cleavage of hemi-methylated substrates it was concluded, that: (1) all three enzymes cleave hemi-methylated DNA substrates; (2) cleavage, at least in case of SgeI, is double-stranded; (3) discovered enzymes cleave the m5C-containing DNA strand predominantly 12 nucleotides away from the modified base to the 3' direction; m5C-free DNA strand is cleaved predominantly 16 nucleotides away from G which is complementary to m5C to the 5' direction; (4) double-stranded DNA cleavage results in fragments which have 5'-protruding ends of predominantly four nucleotides; (5) in case of DNA sequences which are modified by Dcm in both strands each Dcm-methylated pentanucleotide target creates two targets for all three investigated enzymes, one of them residing in one DNA strand and the other one—in complementary DNA strand. Therefore, double-stranded cleavage on both sides of recognized Dcm targets should occur. In accordance with this presumption, cleavage of Dcm-modified DNA substrate indeed resulted in slightly shortened products compared to those resulting after the cleavage within Dcm targets with MvaI (see FIG. 1).

Determination of Specificities of SgeI and SguI

Figure 8:
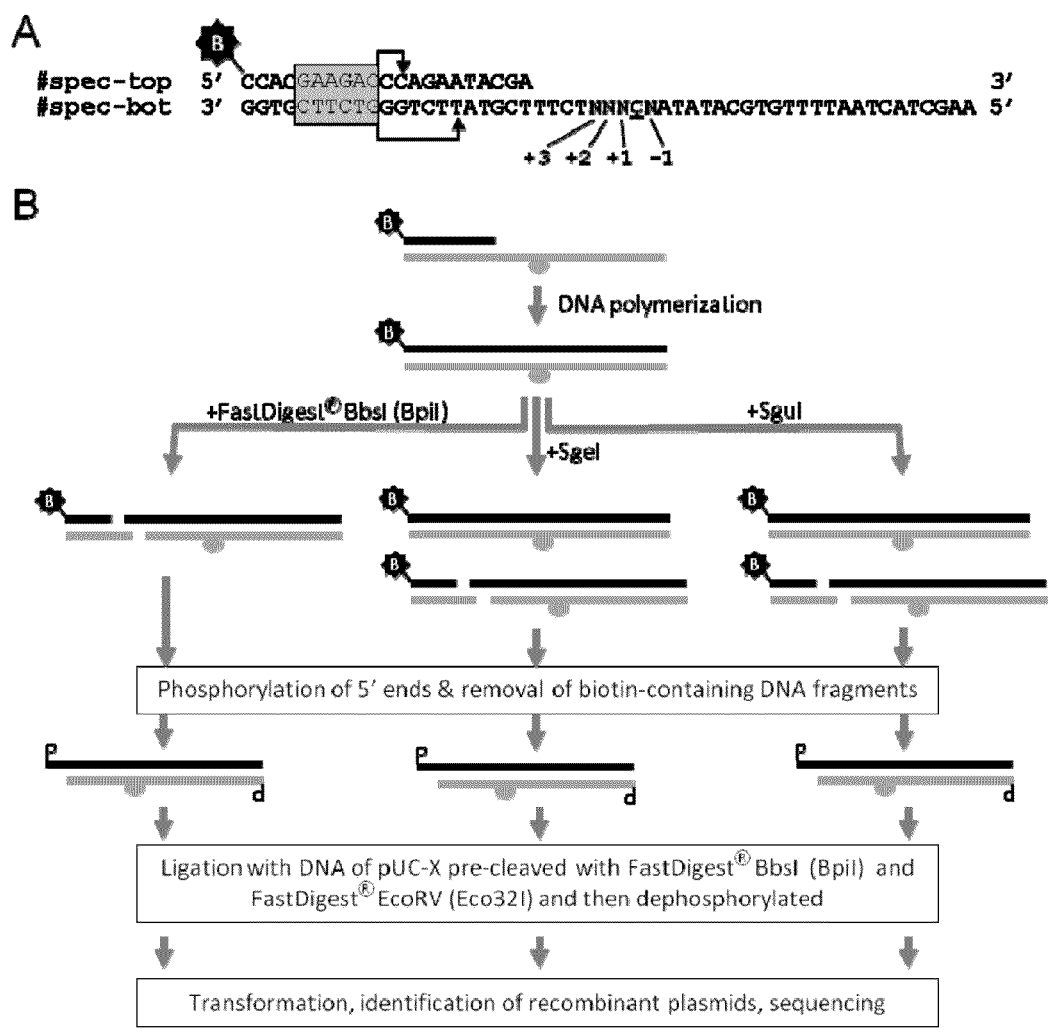
FIG. 8 presents a scheme of experiments used to determine recognition sequences of SgeI and SguI restriction endonucleases. (A) nucleotide sequences of complementary oligonucleotides used in specificity studies. "N" stands for G, A, T or C, "B"—for biotin, underlined C shows the location of m5C. "−1", "+1", "+2" and "+3" shows the position of variable nucleotide N with respect to m5C. FastDigest® BbsI (BpiI) target is shown as a grey box, arrows show cleavage positions within both DNA strands (spec-top (SEQ ID No: 17) and spec-bot (SEQ ID No: 18)); (B) experimental outline. "B" marks biotin, "P"—phosphate group, filled circle marks the position of m5C.

Previous cleavage experiments of DNA substrates, pre-methylated with methyltransferases of various specificities (FIGS. 1 and 2), revealed that all three REases recognize and cleave all Dcm-methylated DNA targets and a fraction of M.SssI-modified targets. In addition, SguI and partially purified REase from bacterial isolate Sa27-m20 digested all M.HpaII-methylated targets, while SgeI digested only their fraction. This information was not enough to predict the exact specificity of tested methylation-specific REases. Therefore, a new approach based on cleavage of randomized collection of potential DNA substrates followed by analysis of cleaved and directionally cloned individual cleavage products was applied for specificity studies (FIG. 8B). A pair of oligonucleotides shown in FIG. 8A was synthesized at Metabion. The 53-nt long template oligonucleotide (#spec-bot) contained a single 5-methylcytosine which is flanked by four unspecified bases (N) at positions mimicking the Dcm target, resulting in $4^4=256$ possible substrate variants. In order to ensure DNA cleavage of randomized DNA substrates as efficient as it was observed in case of hemi-methylated oligoduplex MZ-95/MZ-98 (FIG. 7D), stretches of 14 nucleotides upstream the NCNNN region and 15 nt downstream of this region matching perfectly the sequence of MZ-98 which surrounds the Dcm target were introduced into the structure of degenerate oligonucleotide. In addition, the target of Type IIS restriction endonuclease FastDigest® BbsI (BpiI) was introduced into the structure of #spec-bot in such a way to ensure the cleavage of both DNA strands at positions coinciding with those of methylation-specific restriction endonucleases (FIG. 8A) and resulting the same cohesive end of four nucleotides in length. Finally, the biotin moiety was introduced into the top-strand oligonucleotide #spec-top in order to facilitate removal of not cleaved substrates and unwanted reaction products from reaction mixtures.

The double-stranded DNA substrate shown in FIG. 8A was prepared by mixing 500 pmol of # spec-top with 500 pmol of # spec-bot in 84 µl of water, heating the mixture to 95° C. in a beaker of water and then allowing the beaker to cool to the room temperature. Investigation of recognition sequences of SgeI and SguI was carried out following the experimental scheme shown in FIG. 8B. First of all the upper strand of annealed DNA duplex was filled by adding to the annealing mixture 10 µl of reaction buffer containing 100 mM Tris-HCl (pH 8.0), 50 mM MgCl$_2$, 1 M KCl, 0.2% Triton X-100, 1 mg/ml BSA, 5 µl dNTP mix (2 mM each) and 5 units of T4 DNA polymerase and incubating the reaction mixture at 11° C. for 20 min. Polymerase was then inactivated by heating reaction mixture at 75° C. for 10 min. Cleavage of polymerase-treated DNA substrate was carried out by combining DNA duplexes (500 nM) with restriction endonucleases SgeI (6 units), SguI (4 µl of partially purified preparation) or FastDigest® BbsI (BpiI) (1 µl) in 20 µl of reaction mixture containing 10 mM Tris-HCl (pH 8.0), 5 mM MgCl$_2$, 100 mM KCl, 0.02% Triton X-100 and 0.1 mg/ml BSA in case of SgeI and FastDigest® BbsI (BpiI) or in 20 µl of reaction mixture containing 33 mM Tris-acetate (pH 7.9), 10 mM Mg-acetate, 66 mM K-acetate and 0.1 mg/ml BSA in case of SguI. Reaction mixtures were incubated at 37° C. either for 60 min (SgeI and FastDigest® BbsI (BpiI)) or for 16 hours (SguI) and were terminated by heating at 65° C. for 10 min. Phosphorylation of 5' ends of restriction fragments was performed by adding 10 units of T4 polynucleotide kinase and 2 µl of 10 mM ATP and incubating the reaction mixture at 37° C. for 20 min. Kinase was then inactivated by heating at 75° C. for 10 min. Removal of biotin-tagged intact DNA substrates as well as unwanted reaction products was performed by incubating a half of reaction mixtures with streptavidin-coupled magnetic beads (Dynabeads® M-280 Streptavidin, Invitrogen Inc., USA). The unbound DNA fragments were then purified using the GeneJET™ PCR Purification Kit and ligated to the specially designed pUC-X vector. The latter was constructed by inserting the DNA duplex 5'-CTAGATATCCCGAA-GACTTTTCTCG-3'/3'-TATAGGGCTTCTGAAAAGAGC-CTAG-5' (SEQ ID No: 29/SEQ ID No: 30) into XbaI and BamHI digested pUC57. The resulting plasmid pUC-X contains adjacent sites for blunt-end cutter FastDigest®EcoRV (Eco32I) (see below, boxed) and for Type IIS REase FastDigest®BbsI (BpiI) (see below, underlined). The latter cleaves DNA outside the target (shown by arrows) and leaves 4-nt long cohesive ends which are complementary to ends of fragments generated by enzymes under investigation:

In order to use pUC-X as a cloning vector, DNA of plasmid was first digested with FastDigest®BbsI (BpiI) and FastDigest®EcoRV (Eco32I) and then 5'-phosphates were removed using FastAP™ Thermosensitive Alkaline Phosphatase. Ligation of gel-purified vector with purified cleavage products was accomplished using the Rapid DNA Ligation Kit. Transformation of competent TOP10 cells was done according to standard CaCl$_2$-heat shock protocol.

Screening of transformants containing recombinant plasmids of expected structure was carried out performing colony PCR in 40 µl of DreamTaq™ Green PCR Master Mix supplemented with 100 pM of M13/pUC sequencing primer (−46), 22-mer, and 100 pM of M13/pUC reverse sequencing primer (−46), 24-mer. PCR conditions were as follows: initial denaturation at 95° C. for 1 min, and then 29 cycles of denaturation at 95° C. for 30 sec, annealing at 65° C. for 30 sec and extension at 72° C. for 30 sec, followed by final extension at 72° C. for 60 sec. Amplification products were analyzed by electrophoresis on a 3% agarose gel. DNA fragments longer than 200 bp were sequenced using the same standard primers. In case of each REase which was used to cleave the randomized DNA substrate a hundred of individual cloned fragments was sequenced and analyzed.

Figure 9:
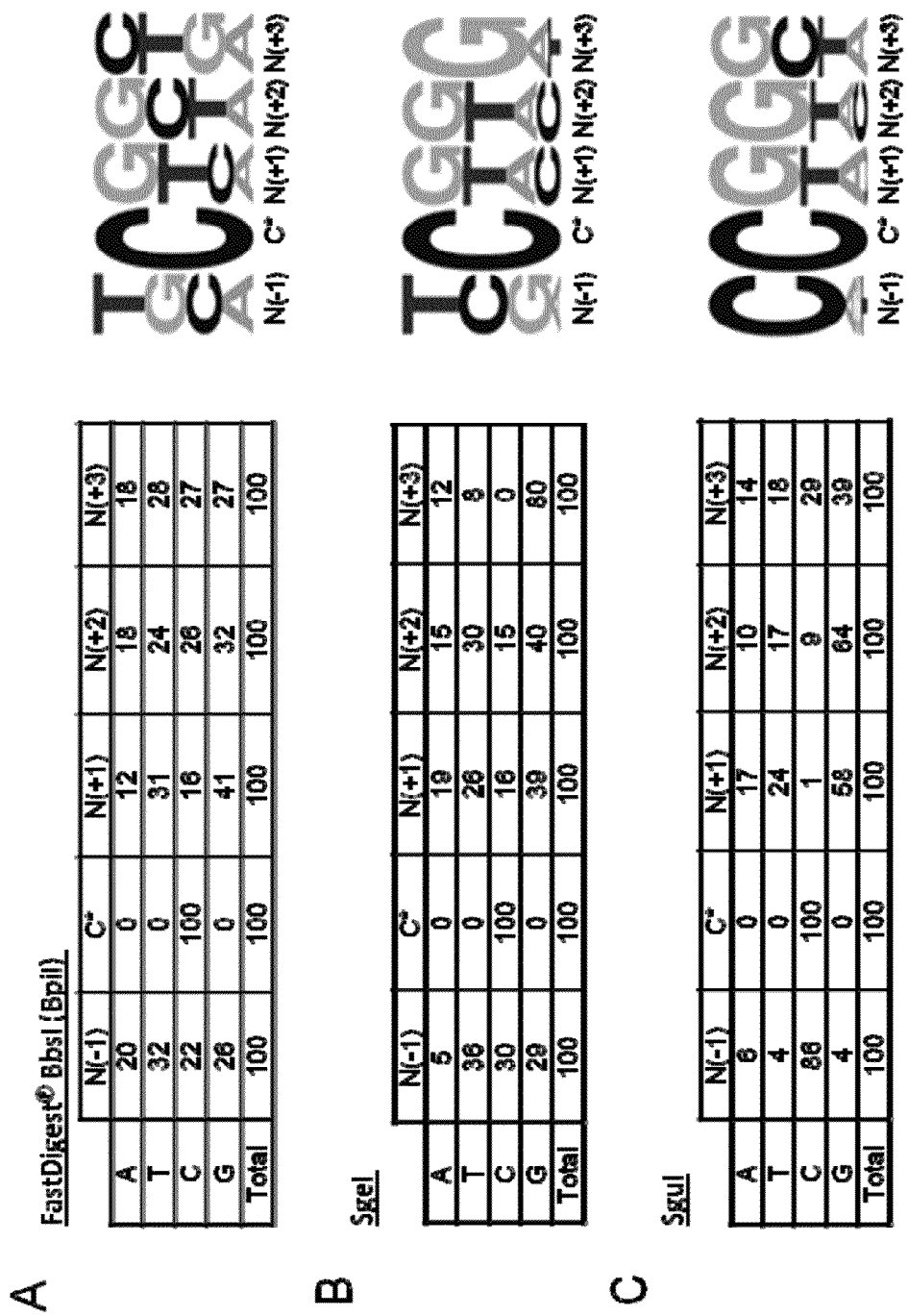
FIG. 9 shows distribution of G, A, T and C nucleotides at variable positions in cloned fragments resulting after the cleavage of substrate, shown in FIG. 8, with: FastDigest® BbsI (BpiI) (A); SgeI (B); SguI (C). "C*" shows the position of m5C within the substrate DNA, numbers "−1", "+1", "+2" and "+3" indicate positions of variable nucleotides with respect to m5C.

FIG. 9 shows summary of sequencing results. Cleavage of randomized DNA substrate with FastDigest® BbsI (BpiI) was used as an internal control to evaluate the frequency of appearance of individual G, A, T and C bases at unspecified N positions within the population of substrates (FIG. 9A). The control revealed quite good distribution of four bases at N(−1) position preceding the m5C, slightly increased frequency of G and decreased frequency of A at N(+1) position which follows the modified nucleotide, and again good distribution of four bases at N(+2) and N(+3) positions. Analysis of SgeI-generated DNA fragments (FIG. 9B) demonstrated that the enzyme strongly prefers DNA substrates which contain G at N(+3), but also is able to recognize and cleave DNA targets having A or T at that position. In addition, it appears that SgeI avoids DNA targets which contain A at N(−1) position. In case of SguI very strong preference for C at N(−1) position was observed, however, there was a small fraction of digested substrates which contained A, T or G instead of C at N(−1). Also, it appears that the enzyme avoids those targets which contain C base at N(+2) and especially at N(+1) position and has some preference for targets which contain G at N(+1) and, to higher extent—at N(+2) position. Based on these experiments it was concluded, that: (1) SgeI preferential recognition target is the sequence m5CNNG; (2) SguI preferential recognition target is the sequence Cm5C; (3) both enzymes have some additional preferences which may result in different cleavage rates of different targets.

Examples described below demonstrate the utility of discovered methylation-specific restriction endonucleases in applications which are based on their unique properties. One such application is site-specific cleavage of fully- and hemi-methylated circular DNA duplexes, leaving not methylated DNA molecules intact. The other application demonstrates the usage of enzymes of this invention for analysis of the level of global cytosine methylation at $5^{th}$ position. The third application demonstrates the genome-wide analysis of individual 5-methylcytosines, and the fourth application demonstrates the usage of enzymes for whole genome analysis of DNA methylation patterns.

From the examples described herein, one skilled in the art can easily ascertain the essential principles of this invention and without departing from the spirit and scope thereof, can make various modifications and changes of the invention in adapting to specific uses and conditions.

EXAMPLE 1

Figure 10:
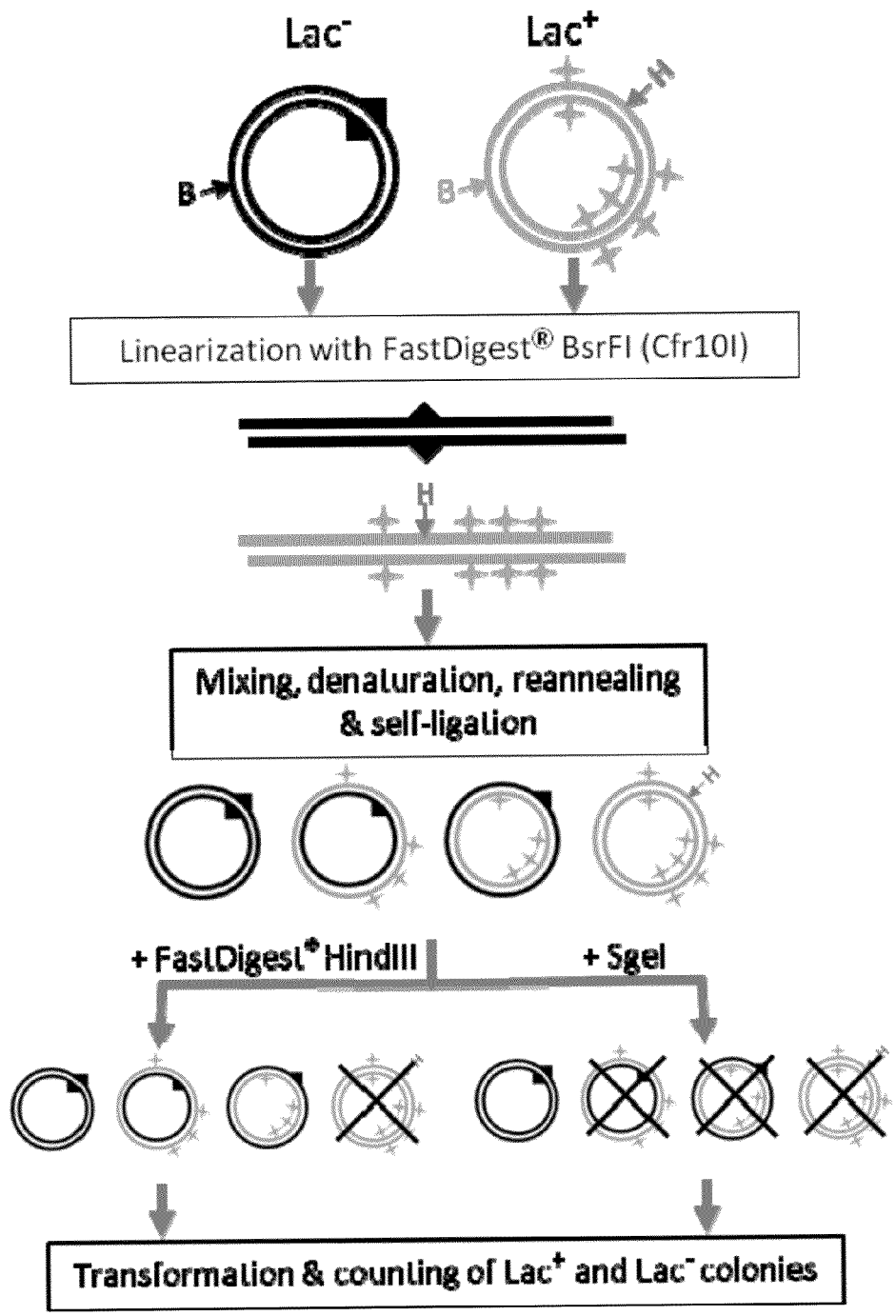
FIG. 10 illustrates the scheme of experiment used to evaluate the effect of methylation-specific restriction endonuclease SgeI on a mixture of double-stranded DNA molecules which are either not modified, or hemi-methylated, or completely Dcm methylated. Grey circles show DNA strands of pUC57 (Lac+ phenotype), black circles—DNA strands of pUC57mut (Lac− phenotype), 4-point stars show 5-methylcytosines which are modified within Dcm targets, arrows represent DNA targets recognized either by FastDigest® BsrFI (Cfr10I) (shown as "B") or by FastDigest® HindIII (marked as "H"). Triangles show the mutation which introduces the translation termination codon within the coding reading frame of lacZ'.

Cleavage of Hemi-Methylated and Completely Methylated DNA Substrates in Presence of Non Modified DNA Substrates To determine how well the discovered methylation-specific restriction enzymes would perform in site-specific cleavage of methylated DNA molecules when they are alongside with not modified DNA molecules, the model experiment shown in FIG. 10 was performed. The two plasmids used, pUC57 and pUC57mut, are identical except one point mutation (CCA.AGC.TTG was changed to CCA.AGC.TAG) within the multiple cloning site of pUC57mut which disrupted the target of HindIII restriction endonuclease (see above, underlined) and introduced a translation termination codon (see above, bolded) into the 5'-terminal part of the lacZ gene which codes for the N-terminal fragment of beta-galactosidase. This fragment, whose synthesis can be induced by inducer of lac operon isopropyl beta-D-thiogalactopyranoside (IPTG), is capable of intra-allelic (or alfa) complementation with a defective form of LacZ encoded by a host carrying the mutation lacZΔM15 (Messing et al., 1977; Messing et al., 1981). In the presence of IPTG bacteria synthesize both oligopeptides and produce functional beta-galactosidase which metabolizes the indicator dye 5-bromo-4-chloro-3-indolyl-beta-D-galactoside (XGAL), resulting in Lac⁺ phenotype and in blue color of colonies. Appearance of translation termination codon disrupted the integrity of N-terminal fragment of beta-galactosidase, abolished alfa-complementation and resulted in Lac⁻ phenotype (and white color) of cells transformed with pUC57mut.

DNA substrates, used for preparation of all possible types of circular DNA molecules shown in FIG. 10, were isolated from different hosts. In order to keep pUC57mut not methylated, DNA of this plasmid was isolated from GMMG2163 strain, while Dam and Dcm methylated DNA of pUC57 was isolated from DH10B cells. Plasmids were purified using the GeneJET™ Plasmid Miniprep Kit, and 2 μg of both substrates were digested in parallel with 2 μl of FastDigest® BsrFI (Cfr10I) REase in 100 μl of FastDigest buffer at 37° C. for 60 min. The completeness of digestion was confirmed by electrophoresis, and then FastDigest® BsrFI (CHOI) was removed by chloroform extraction. Formation of heteroduplexes was carried out by mixing digested DNA molecules of pUC57 and pUC57mut at a ratio 1:1 (375 ng of each) in 150 μl of 1× FastDigest buffer, while two parallel control reactions contained either 750 ng of pUC57 or 750 ng of pUC57mut. Denaturation and annealing steps were performed on PCR device using the initial denaturation at 95° C. for 5 min and then gradually decreasing the temperature by 5 degrees after 1 minute of incubation (90° C. for 1 min, then 85° C. for 1 min, then 80° C. for 1 min and so on) until the temperature reached 5° C. Products of annealing were analyzed by electrophoresis on a 1% agarose gel. Circularization of annealed DNA molecules was performed by adding 6 μl of 10 mM ATP and 15 units of T4 DNA ligase to 120 μl of each annealing mixture and then incubating reactions at room temperature for 60 min. Reactions were stopped by heating at 65° C. for 10 min.

In order to check if the population of circularized DNA molecules contains not only initial double-stranded DNA molecules, but also heteroduplexes in which one DNA strand is modified as shown in FIG. 10, samples of ligation reaction mixtures (5 μl) were mixed with 14 μl of 1× FastDigest buffer and 1 μl of FastDigest® HindIII, reactions were incubated at 37° C. for 60 min and then samples of 5 μl were used to transform competent Top10 cells. The same amount of undigested mixtures served as controls. Transformants were plated onto LB-agar plates supplemented with ampicillin, IPTG and XGAL. Blue (Lac⁺) and white (Lac⁻) colonies were counted. Theoretically, the 1:1 mixture of parental DNA molecules should yield comparable numbers of blue (Lac⁺) and white (Lac⁻) transformants, while cleavage of this mixture with HindIII should eliminate or sharply reduce the population of Lac⁺ colonies because pUC57 but not pUC57mut has a target for this enzyme. However, in case if heteroduplexes are formed the population of annealed DNA molecules should contain 25% of homoduplexes corresponding to one type of parental molecules, 25%—to the other type of parental molecules and 50% should be heteroduplexes as shown in FIG. 10. Of note, one out of two DNA strands of each heteroduplex contains the lacZ' gene of wild-type, and each heteroduplex has a chance to confer Lac⁺ phenotype. More important, heteroduplexes should be resistant to HindIII cleavage. Therefore, it was expected that the formation of heteroduplexes will be manifested by increased ratio between Lac⁺ (blue) and Lac⁻ (white) colonies and only limited reduction of this ratio after HindIII cleavage. Results of transformation were as follows:

| Plasmids used | HindIII uncleaved: white (W)/blue (B) colonies Lac⁻:Lac⁺ ratio | HindIII digested: white (W)/blue (B) colonies Lac⁻:Lac⁺ ratio |
|---|---|---|
| pUC57mut + pUC57 | 980 W/3280 B 1:3.3 ratio | 2000 W/3480 B 1:1.7 ratio |
| pUC57mut | 8980 W | 8790 W |
| pUC57 | 10820 B | 1200 B |

Results demonstrated that HindIII reduces the number of colonies more than tenfold in case of pUC57, but, as expected, has no impact on efficiency of transformation by pUC57mut. Transformation by mixed, denatured, annealed and self-ligated plasmids revealed the ratio 1:3.3 of Lac⁻ to Lac⁺ transformants which is close to the theoretical 1:3 distribution in model where all molecules of heteroduplexes result in Lac⁺ phenotype. Incubation of ligation mixture with HindIII reduced this ratio down to 1:1.7, and this ratio is again close to the theoretical 1:2 ratio of model where one third of molecules resulting in Lac⁺ phenotype contains HindIII target and thus are destroyed.

Taken together, results of transformation confirmed the existence of heteroduplexes alongside with parental DNA molecules in prepared ligation reaction mixture. In order to test how efficiently SgeI cleaves hemi-methylated heteroduplexes, 1 µl of SgeI (3 units) was added to 39 µl of ligation reaction mixtures, reactions incubated at 37° C. temperature for 60 min and then samples of 2.5 µl were used to transform competent Top10 cells. The same amount of undigested mixtures served as controls. Again, blue (Lac⁺) and white (Lac⁻) colonies were counted. Results of transformation were as follows:

| Plasmids used | SgeI uncleaved: white (W)/blue (B) colonies Lac⁻:Lac⁺ ratio | SgeI digested: white (W)/blue (B) colonies Lac⁻:Lac⁺ ratio |
|---|---|---|
| pUC57mut + pUC57 | 3000 W/10000 B 1:3.3 ratio | 2000 W/148 B 13.5:1 ratio |
| pUC57mut | 11000 W | 10000 W |
| pUC57 | 14240 B | 1 B |

The experiment demonstrated that SgeI greatly reduces the efficiency of Dcm-methylated pUC57 transformation, but has low impact on efficiency of transformation of non modified pUC57mut. When both plasmids were mixed, the enzyme cleaved modified molecules of pUC57 (which confers Lac⁺ phenotype) efficiently, reducing the initial 1:3.3 ratio of Lac⁻ to Lac⁺ colonies down to 13.5:1 ratio. Based on decrease of this ratio the 45-fold enrichment of not modified homoduplexes of pUC57mut was calculated. All these results show that SgeI and other discovered methylation-specific enzymes cleave hemi-methylated and completely methylated DNA substrates in complex reaction mixtures which also include not modified DNA substrates, and thus may be used for enrichment of not modified DNA molecules.

EXAMPLE 2

Figure 11:
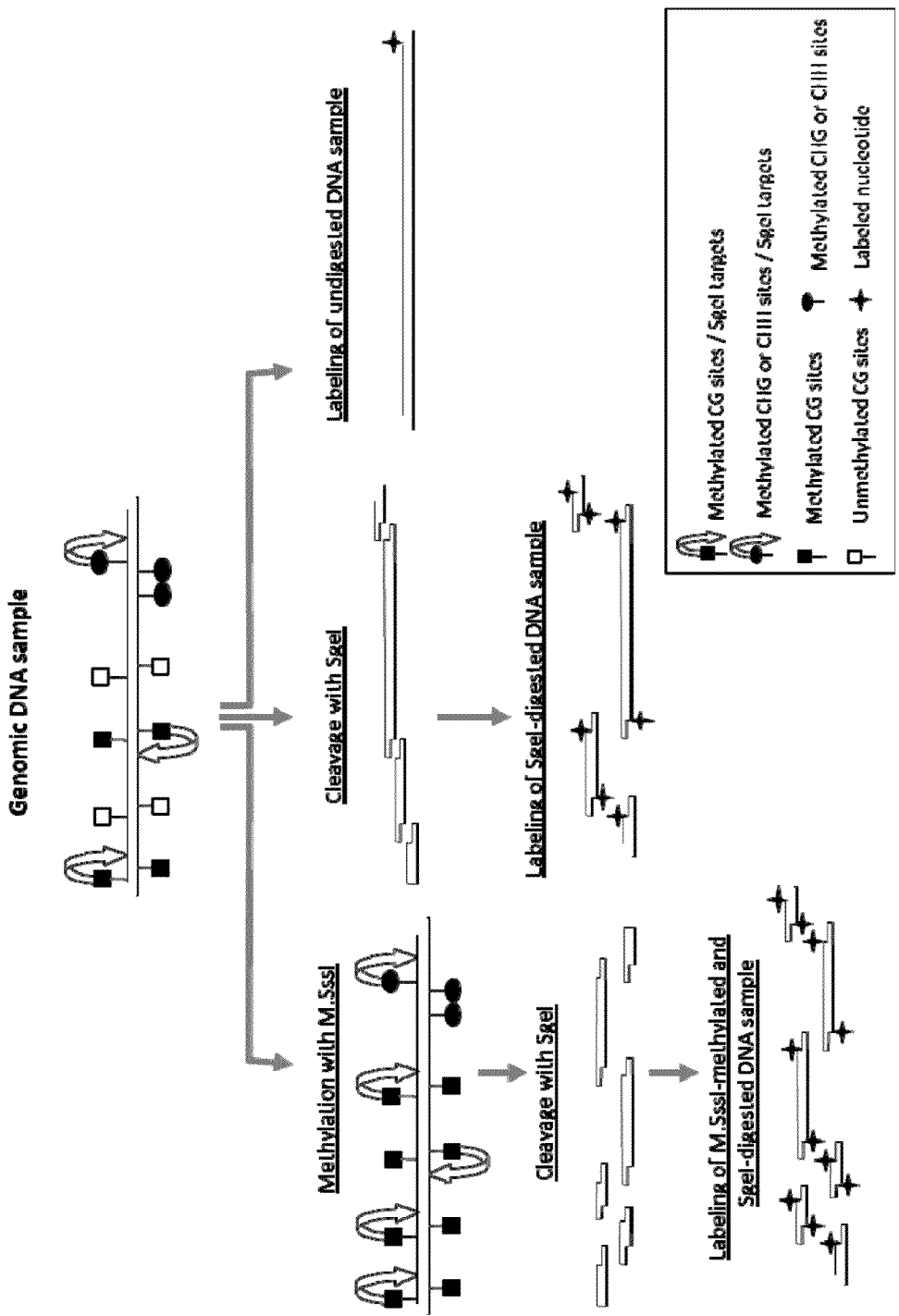
FIG. 11 shows the experimental outline of analysis of global DNA methylation levels using methylation-specific restriction endonuclease SgeI and the 3'-terminal labeling. Legend for used symbols is boxed.

Analysis of Global DNA Methylation Levels Using Methylation-Specific Restriction Endonucleases The detailed scheme of this application is shown in FIG. 11.

EXAMPLE 3

Figure 12:
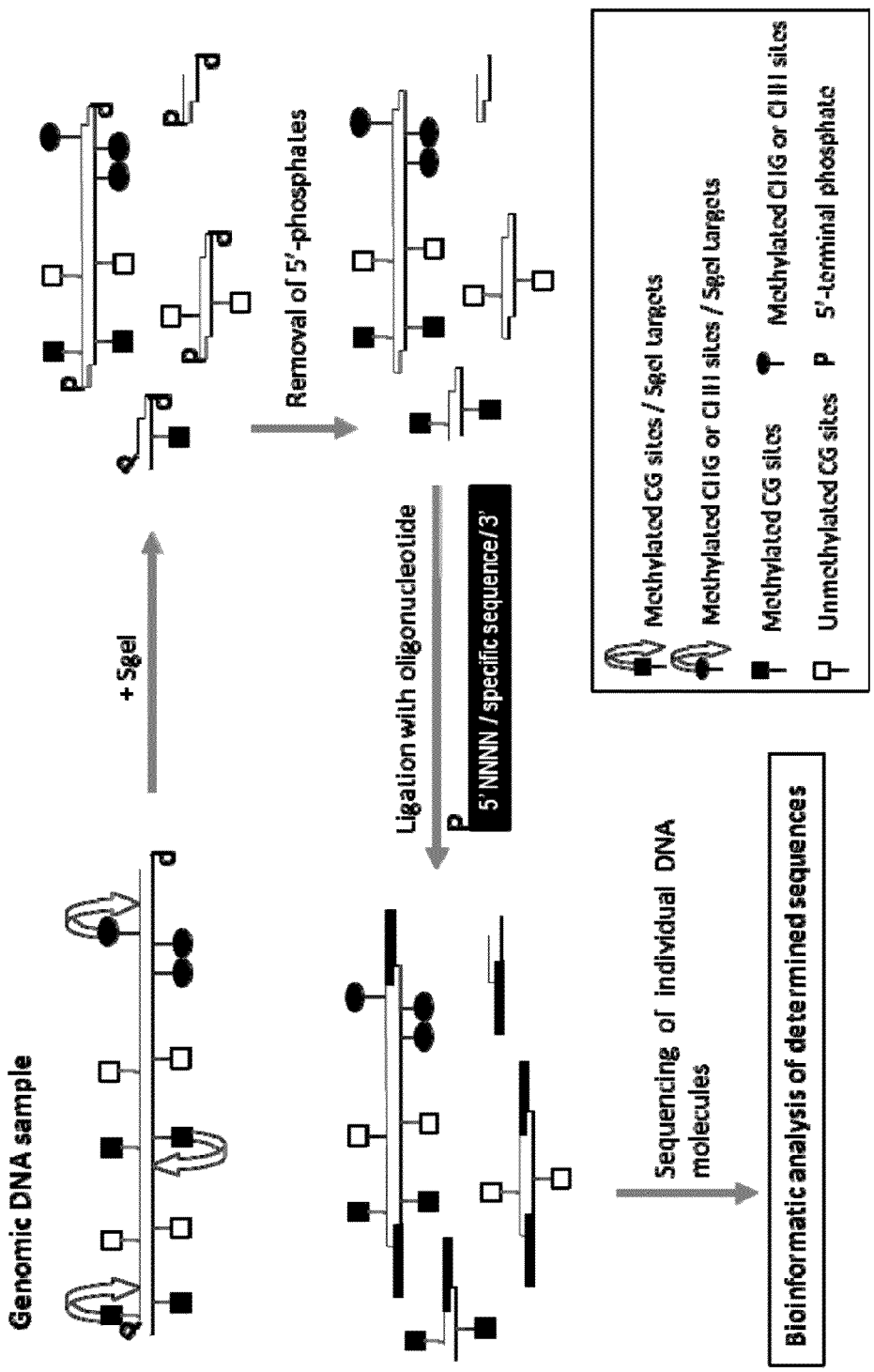
FIG. 12 shows the experimental outline of genome-wide analysis of individual 5-methylcytosines using methylation-specific restriction endonuclease SgeI. Sequencing of individual DNA molecules (either directly or, if necessary, after bisulfate conversion of cytosines to uraciles and amplification) is carried out using the primer which is complementary to the specific sequence of ligated oligonucleotide. Legend for symbols used is boxed.
Figure 14:
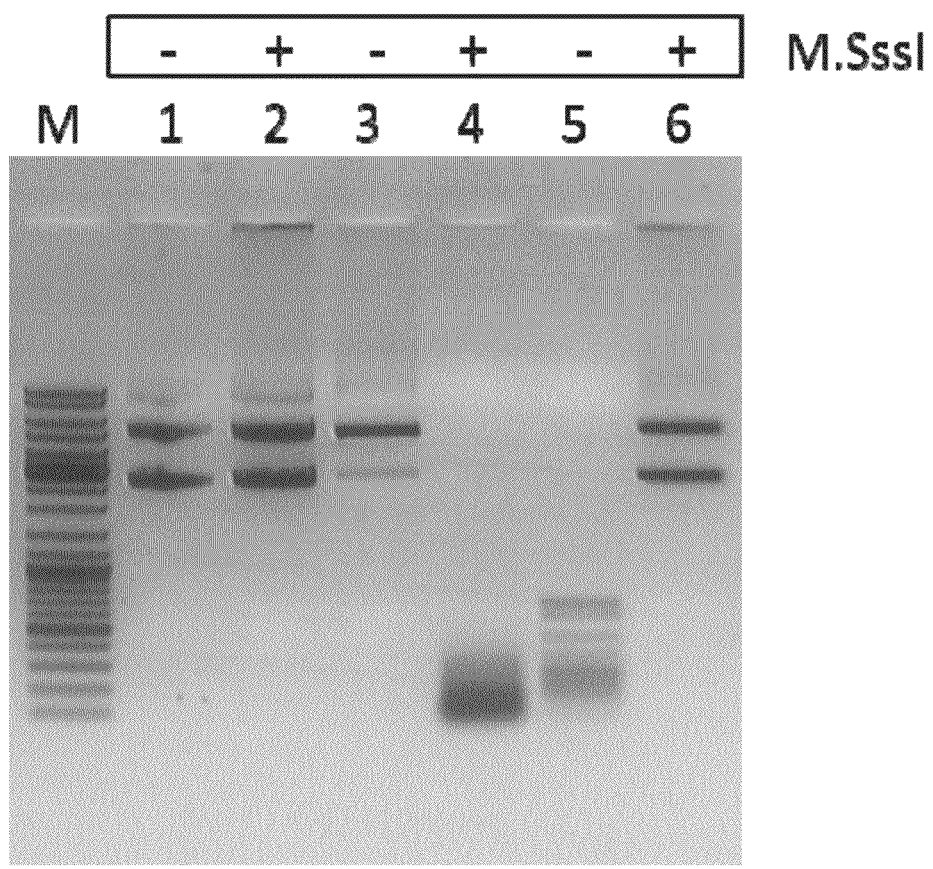
FIG. 14 provides an evaluation of the completeness of pBR322 DNA modification by M.SssI methyltransferase. Lanes 1 and 2, DNA of pBR322 before and after M.SssI treatment, respectively; lanes 3 and 5, reaction products resulting after incubation of unmodified pBR322 with SgeI and HpaII, respectively; lanes 4 and 6, reaction products resulting after incubation of M.SssI-treated pBR322 with SgeI and HpaII, respectively; lane M, GeneRuler™ DNA Ladder Mix. "–", pBR322 DNA (dam$^-$ dcm$^-$); "+", DNA of pBR322 (dam$^-$ dcm$^-$) modified by M.SssI.

Genome-Wide Analysis of Individual 5-Methylcytosines Using Methylation-Specific Restriction Endonucleases The detailed scheme of this application for genome-wide analysis of modified cytosines is shown in FIG. 12. In order to demonstrate the utility of methylation-specific restriction endonucleases for precise identification of modified bases through nucleotide sequencing in more straightforward way, a mixture of two DNA substrates (one, DNA of pBR322, was modified in all CpG targets with M.SssI methyltransferase, while the other one, DNA of phage lambda, was not modified) was used in the model experiment instead of a complex natural genomic DNA modification status of which is unique, locus-specific and yet needs to be determined experimentally. DNA (dam dcm) of pBR322 was modified with M.SssI (Fermentas) as follows: 10 µg of DNA was incubated with 100 u of enzyme in 200 µl reaction buffer (33 mM Tris-acetate (pH 7.9 at 37° C.), 10 mM Mg-acetate, 66 mM K-acetate, 0.1 mg/ml BSA) supplemented with 0.16 mM S-adenosylmethionine for 1 h at 37° C. After incubation the reaction mixture was extracted with equal volume of chloroform and precipitated by isopropanol. DNA pellets were dissolved in 50 µl of water and DNA concentration was measured using Nano-Drop™. The completeness of the methylation reaction was evaluated by incubating the modified DNA with restriction endonuclease HpaII which is sensitive to the introduced modification, but cleaves non-modified DNA. In contrast, SgeI cleaves only methylated DNA. Incubations were as follows: 0.5 µg of M.SssI-modified pBR322 DNA as well as the control DNA (modification-free pBR322) were incubated with 3 u of SgeI in SgeI reaction buffer or with 1 µl of FD HpaII in FastDigest™ buffer for 1 h at 37° C. After heat inactivation (65° C., 20 min) the reaction products were analysed on a 1% agarose gel (FIG. 14). HpaII cleaved unmodified pBR322 DNA (FIG. 14, lane 5), but not the methylated one (FIG. 14, lane 6). This result was interpreted as an indication of complete DNA modification. In contrast, SgeI cleaved methylated DNA, while unmodified DNA remained generally intact (FIG. 14. lanes 4 and 3, respectively).

The M.SssI-modified DNA of pBR322 was mixed with unmodified (dam⁻ dcm⁻) DNA of phage λ and used as a substrate for cleavage with SgeI as follows: 200 µl of the mixture containing 2 µg of M.SssI-modified pBR322 DNA, 2 µg of phage λ (dam dcm) DNA and SgeI reaction buffer (10 mM Tris-HCl (pH 8.0), 5 mM MgCl$_2$, 100 mM KCl, 0.02% Triton X-100 and 0.1 mg/ml BSA) was divided into two equal parts. One of them was left at 4° C. as SgeI-untreated control, while the other one was supplemented with 3 u of SgeI and incubated for 20 min at 37° C. SgeI was then heat inactivated at 65° C. for 20 min. Dephosphorylation of 5' ends of reaction products was done by adding 15 u of FastAP Thermosensitive alkaline phosphatase and incubating the reaction mixture 20 min at 37° C. Identical parallel control reactions were performed except that they contained either only M.SssI-modified pBR322 DNA or only phage λ (dam⁻ dcm⁻) DNA. After incubation the reaction mixtures as well as SgeI-untreated controls were extracted with equal volumes of chloroform and precipitated by isopropanol. The DNA pellets were dissolved in 20 µl of water. The DNA cleavage pattern was evaluated by analysis of samples on 1% agarose gel (not shown) and DNA concentrations were measured using Nano-Drop™.

Dissolved DNA samples were used in ligation reaction with single-stranded oligonucleotide Rand-30-1 (5'-phosphate-NNNNAAGCGTGATAGAGCGATTCTGGCTCG (SEQ ID No: 33)). Ligation reactions were done using Rapid Ligation™ buffer. In all cases 50 µl of the reaction mixture contained 8 µl (~300 ng) of purified DNA, 90 pmol of the oligonucleotide Rand-30-1 and 10 u of T4 DNA ligase. The reactions were incubated for 1 h at 22° C., purified using the GeneJET™ PCR Purification Kit and analysed on a 1% agarose gel (not shown). Purified ligation reaction products were diluted to the final concentration of approx 0.5 ng per µl and used as templates in PCR reactions.

Figure 15:
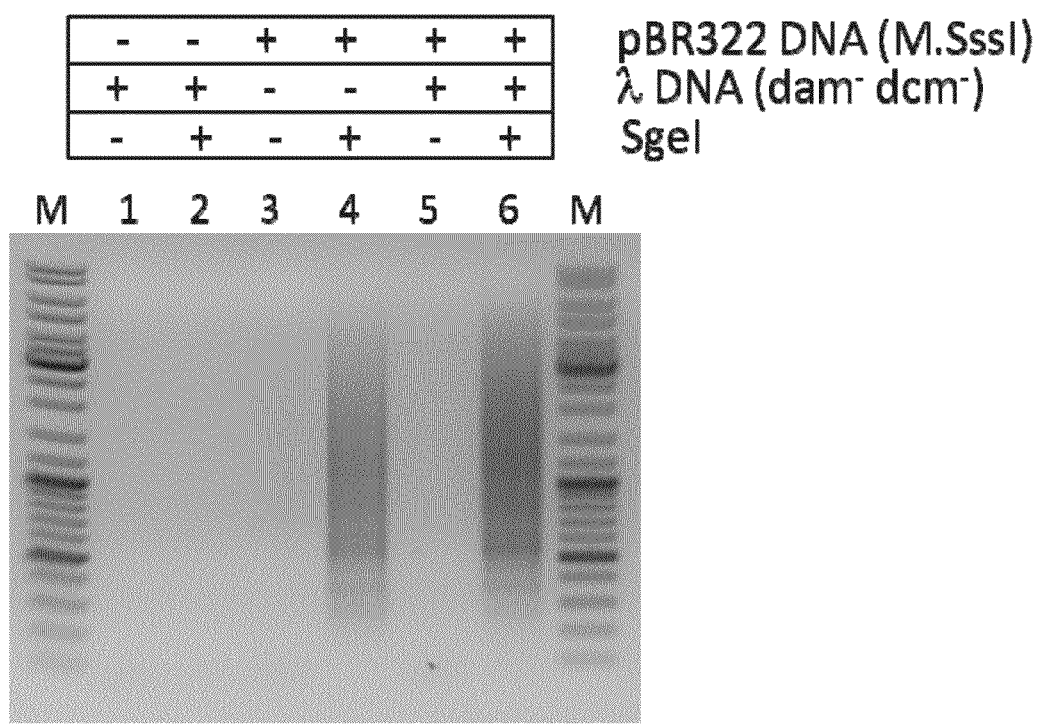
FIG. 15 shows the results of PCR amplification from ligated DNA templates from Example 3. Lanes 1, 3, 5—DNA substrates used for ligation with single-stranded oligonucleotide were SgeI-untreated; lanes 2, 4, 6—DNA substrates used for ligation were treated with SgeI. "+" and "–" indicates the presence or absence, respectively, of indicated DNA substrates in individual ligation reactions; lane M, GeneRuler™ DNA Ladder Mix.

Polymerase chain reactions were carried out using 1 µl of purified ligation reaction products as templates in 20 µl of DreamTaq™ buffer containing 2 mM $MgCl_2$, 0.2 mM dNTPs, 0.5 µM of primer Rand-30-1-rev (5'-CGAGCCAGAATCGCTCTATCACGCTT (SEQ ID No: 34)) which is complementary to the ligated oligonucleotide Rand-30-1, and 1 unit of DreamTaq™ polymerase. Following PCR conditions were used: initial denaturation at 95° C. for 5 min, and then 30 cycles of denaturation at 94° C. for 20 sec, annealing at 64° C. for 30 sec and extension at 72° C. for 3 min. Amplification products were analyzed by electrophoresis on a 1% agarose gel (FIG. 15). Under conditions used DNA amplification products were observed only when ligation reactions contained DNA of pBR322 which was M.SssI-modified and then SgeI-cleaved either in the absence or in the presence of accompanying unmodified λ DNA (FIG. 15, lanes 4 and 6, respectively). Of note, the pattern of amplified fragments was very similar in both cases, suggesting that all these fragments originated from pBR322. No PCR products were detected in cases when SgeI-untreated DNA samples were used for ligation with single-stranded oligonucleotide (FIG. 15, lines 1, 3 and 5) or when SgeI was incubated with unmodified DNA of λ phage (FIG. 15, line 2). These results indicate that the single-stranded oligonucleotide Rand-30-1 was ligated by T4 DNA ligase to variant 4 nt long sticky ends generated by SgeI on M.SssI-modified DNA of pBR322, and ligated molecules served as templates in PCR amplification using complementary oligonucleotide Rand-30-1-rev. Taken together, these results support the idea that the ligation reaction may be followed by direct sequencing (or amplification and sequencing) of individual molecules generated during the ligation reaction.

SgeI restriction endonuclease cleaves DNA targets at a fixed distance from modified cytosines. Therefore, one could expect that nucleotide sequence information gathered by (i) cleavage of modified DNA under investigation with SgeI, (ii) ligation of cleavage reaction products with single-stranded oligonucleotide, and (iii) either direct sequencing of ligation reaction products or, alternatively, their cloning followed by sequencing of resulting recombinant plasmids should allow to predict C bases which have been modified within SgeI targets and thus served as parts of recognition sites. In order to test this assumption, 1 µl of PCR fragments amplified using the mixture of ligated DNA substrates as templates (FIG. 15, lane 6) was ligated with pJET1.2 cloning vector using CloneJET™ PCR Cloning Kit (Fermentas) following manufacturer recommendations. Competent *E. coli* DH10B cells were transformed with ligation mixture using the $CaCl_2$-heat shock method and spread onto LB-agar plates supplemented with ampicillin. Plates were incubated overnight at 37° C. Screening of recombinant plasmids was done by colony PCR using 20 µl of PyroStart™ Fast PCR Master Mix supplemented with 4 pmol of pJET1.2 Forward Sequencing Primer and 4 pmol of pJET1.2 Reverse Sequencing Primer. PCR conditions were as follows: initial denaturation at 95° C. for 4 min, and then 25 cycles of denaturation at 94° C. for 10 sec, annealing at 60° C. for 10 sec and extension at 72° C. for 1 min. Amplification products were analyzed by electrophoresis on a 1% agarose gel. 64 recombinant plasmids carrying cloned fragments were purified using GeneJET™ Plasmid Miniprep Kit and then sequenced using either pJET1.2 Forward Sequencing Primer or pJET1.2 Reverse Sequencing Primer, or both.

Examination of sequencing data revealed poor quality of 5 sequenced plasmids, and they were discarded from further analysis. Remaining 59 plasmids contained DNA fragments originating from pBR322. Of these, 50 plasmids contained DNA fragments of the expected structure (i.e. flanked by sequences originating from Rand-30-1 on both sides) and were analysed in details, while 9 plasmids had DNA fragments with the sequence of Rand-30-1 on only one side of the cloned fragment. Having in mind that the mixture of two DNA substrates (unmodified DNA of phage λ and M.SssI-modified DNA of pBR322) was used in SgeI cleavage reaction followed by ligation with single-stranded oligonucleotide Rand-30-1, sequencing results clearly indicate that modified substrates were preferentially PCR-amplified following the approach described in this example.

Nucleotide sequences of 50 cloned DNA fragments as well as nt sequences which surround these fragments in pBR322 were analyzed for the presence of either preferential SgeI recognition sequence 5'-CNNG or alternative recognition sequence 5'-CNNA, both located at the distance of 8, 9 or 10 nucleotides away from the ligated single-stranded oligonucleotide Rand-30-1 and overlapping the DNA sequence 5'-CG which is recognized by M.SssI. Table below summarizes results of bioinformatic analysis.

| Putative modified target | Distance from the last base of the target to the first base of the ligated single-stranded oligonucleotide | No of variants found |
|---|---|---|
| 5'-m5CGNG | 9 | 84 |
| 5'-m5CGNA | 9 | 2 |
| 5'-m5CGNG | 10 | 2 |
| 5'-m5CGNA | 10 | 0 |
| 5'-m5CGNG | 8 | 10 |
| 5'-m5CGNA | 8 | 2 |

As expected, analysis of sequenced fragments and regions which surround cloned fragments in pBR322 revealed the presence of properly situated putative SgeI target for each cleavage event (50 fragments; in total 100 cleavage events). Of note, 96% putative targets contained the structure 5'-CGNG, while remaining 4% had the alternative structure 5'-CGNA. The dominating distance between the target and the cleavage point, as expected, was found to be 9 bp (86%), 2% of putative targets were at a distance of 10 bp and 12%— at a distance of 8 bp. Collectively, sequencing results confirmed that (1) SgeI cleaves modified targets, (2) DNA targets cleaved by SgeI are in the context of either 5'-CGNG or 5'-CGNA, (3) cleavage occurs predominantly 12 nucleotides away from the 5-methylcytosine in the 3' direction, (4) resulting cohesive ends can be ligated with single-stranded oligonucleotides, (5) ligated DNA molecules can be amplified using the primer which is complementary to the ligated single-stranded oligonucleotide, (6) sequencing results can be used to predict the C base which was modified.

EXAMPLE 4

Figure 13:
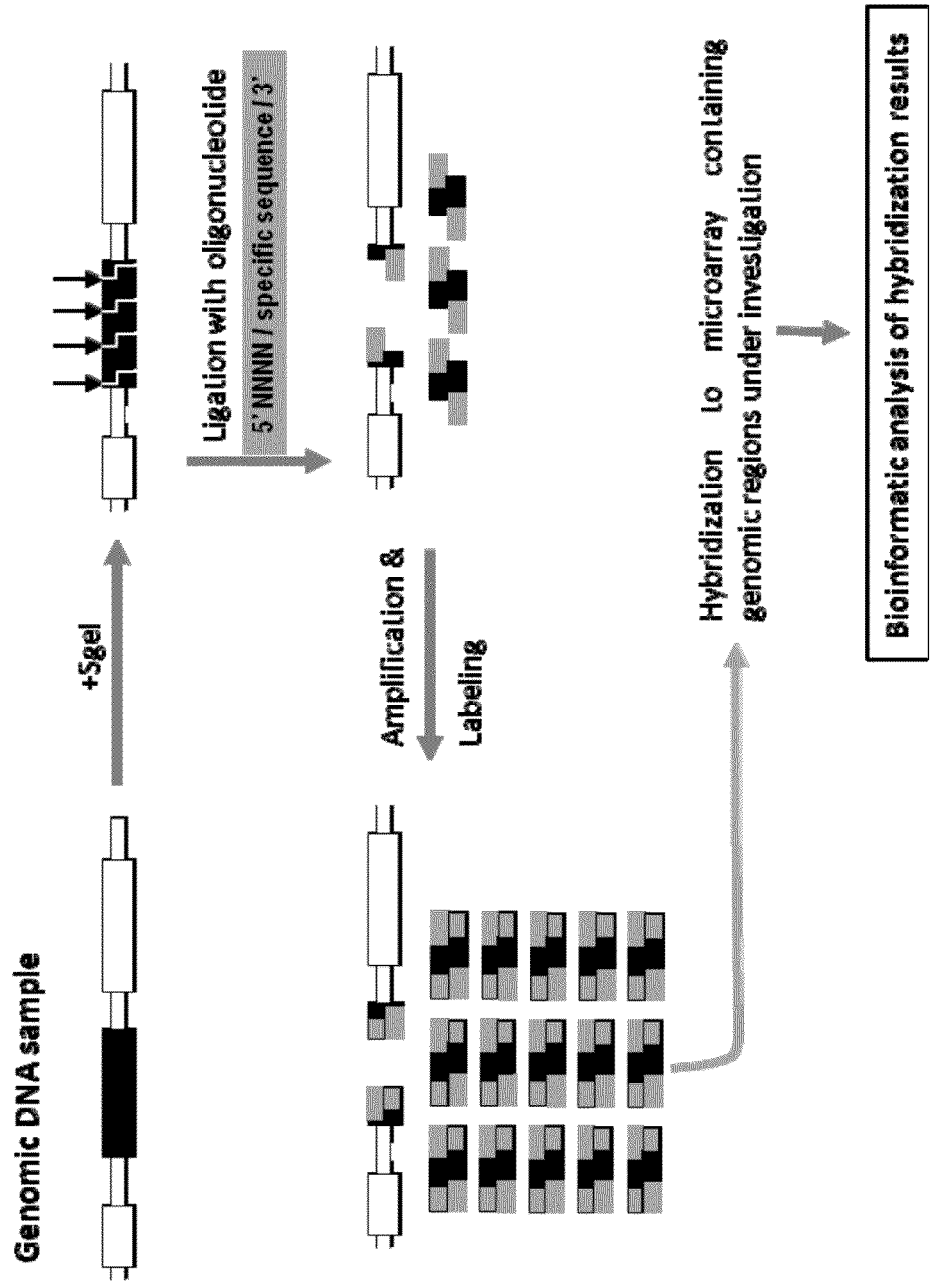
FIG. 13 shows the experimental outline of whole genome analysis of DNA methylation patterns using methylation-specific restriction endonuclease SgeI. Open boxes represent not methylated CG islands, filled—methylated CG island, arrows show positions of double-stranded DNA cleavage by SgeI. Amplification of DNA fragments is carried out using the primer which is complementary to the specific sequence of ligated oligonucleotides.

Whole Genome Analysis of DNA Methylation Patterns Using Methylation-Specific Restriction Endonucleases The detailed scheme of this application is shown in FIG. 13. In order to demonstrate the utility of methylation-specific restriction endonucleases for analysis of DNA methylation patterns by hybridization in more straightforward way, the model experiment used a mixture of two DNA substrates described in previous Example instead of a complex natural genomic DNA which modification status is unique, locus-specific and yet needs to be determined experimentally. Also, Southern hybridization was used as a tool for identifying DNA fragments which were amplified in polymerase chain reaction under conditions described in previous Example. In its essence, analysis of DNA samples by hybridization to DNA microarrays closely resembles Southern hybridization, and two approaches differ by the mode how DNA for hybridization was prepared: in case of DNA microarrays individual DNA fragments (either single-stranded or double-stranded) representing individual regions of genome under investigation are spotted onto surface of glass or another solid support, while in case of Southern hybridization individual DNA fragments are generated by cleaving of genomic DNA under investigation with restriction endonucleases, electrophoretic separation of resulting individual fragments according to their size in agarose gel, and then transfer of DNA fragments onto membrane. Therefore, both approaches should be regarded as equivalent methods.

In order to generate radiolabelled hybridization probes three individual DNA samples representing the methylated DNA (M.SssI-modified DNA of pBR322), the unmethylated DNA (DNA of phage λ) and their 1:1 mixture were treated with SgeI, purified and ligated with the single stranded DNA oligonucleotide following conditions described in the previous example. Purified products of ligation reactions were diluted 10-fold, and diluted DNA samples (1 µl) served as templates for PCR. 30 cycles of PCR were carried out using 5 units of DreamTaq™ DNA polymerase in 100 µl of 1× DreamTaq buffer containing 0.5 µM of primer Rand-30-1-rev (5'-CGAGCCAGAATCGCTCTATCACGCTT (SEQ ID No: 34)) which is complementary to the ligated oligonucleotide Rand-30-1, 0.2 mM dNTPs and 0.925 MBq radioactively labelled α[$^{33}$P] dATP (80 nM). 1 µl aliquots of PCR mixtures were taken after amplification in order to determine the extent of label incorporation in three polymerase chain reactions. It was found that labelling of PCR products amplified using both the mixture of modified/unmodified DNAs and modified DNA alone as templates were similar ($2\times10^5$ cpm/µl and $1\times10^5$ cpm/µl, respectively), while incorporation of radioactive label into products amplified from unmodified λ DNA substrate was lower by more than two orders of magnitude ($0.5\times10^3$ cpm/µl). These results confirmed that the single-stranded oligonucleotide Rand-30-1 can be ligated to variant sticky ends generated by SgeI, and that ligated oligonucleotide serves as a primer binding site for PCR amplification.

In order to answer the question whether DNA fragments which were methylated and thus cleaved by SgeI could be unambiguously identified by hybridization, Southern hybridization experiment using individual fragments of either pBR322 or phage λ DNA, or their mixture was done as follows. 10 µg of pBR322 DNA was digested (in parallel) with 10 µl of Fast Digest® SfcI and Fast Digest® FspI in 100 µl of Fast Digest buffer at 37° C. for 30 min, resulting in DNA fragments of 2600, 892, 678, 191 bp and 2132, 1096, 1035, 98 bp, respectively. DNA fragments were purified using Gene-Jet™ Gel extraction Kit (Fermentas), and concentration was determined spectrofotometrically. Both sets of fragments were mixed at a ratio 1:1. For λ DNA representation the λ DNA/Eco91I marker (Fermentas) was used. Three replicates of DNA fragments originating either from pBR322, or from λ DNA, or their mixture (15.6 fmol of each set of fragments per lane) were loaded onto 1% agarose gel in 1×TAE buffer and fractionated by gel electrophoresis. Gel was stained with ethidium bromide, DNA fragments visualized with UV light, photographed (FIG. 16, part I) and then transferred to HyBond N+ nylon membrane (GE Healthcare) following manufacturer's recommendations. Transferred DNA fragments were fixed to the membrane by exposing it to UV light for 2 min. The membrane was cut into 3 pieces bearing all three fractionized and immobilized sets of fragments and placed into separate hybridization bags. Sonicated salmon sperm DNA was denatured by boiling for 5 min. and chilled on ice. The bags were filled with 3 ml of pre-hybridization solution containing 100 µg/ml denaturized sonicated salmon sperm DNA, and sealed. Pre-hybridization was carried at 42° C. for 2 hours with constant agitation. Labeled DNA probes were denatured by boiling for 5 min. and then immediately chilled on ice. Hybridization solutions were prepared by adding 50 µl of individual labelled probes to 3 ml of pre-hybridization solutions. Then, pre-hybridization solutions were discarded from hybridization bags, and hybridization solutions (3 ml) containing individual labeled probes derived from unmethylated SgeI-treated λ DNA substrate (FIG. 16, part II, A), from unmethylated λ DNA substrate which was mixed with M.SssI-methylated DNA of pBR322 before SgeI treatment (FIG. 16, part II, B), and SgeI-treated DNA of pBR322 modified by M.SssI (FIG. 16, part II, C) were added to membranes. The bags were sealed and incubated at 42° C. for 12 hours with constant agitation. Hybridization was followed by washing of membranes twice in 2×SSC+0.1% SDS for 10 min at room temperature, twice in 0.1 SSC+0.1% SDS for 10 min at room temperature and twice in 0.1 SSC+0.1% SDS for 10 min at 65° C. Then membranes were dried on Whatman™ 3 MM paper, wrapped in Saran Wrap™ and exposed to an imaging plate for 16 hours. The plate was scanned with phosphorimager, results of radioautography are shown in FIG. 16.

Figure 16:
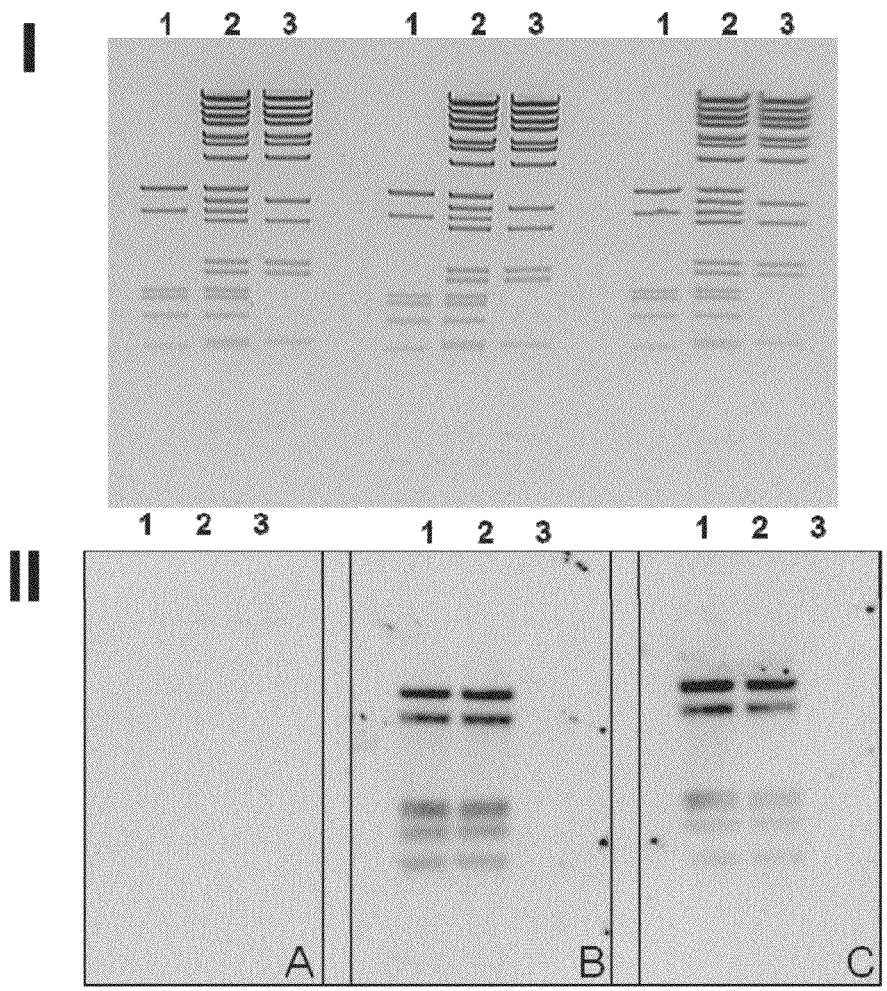
FIG. 16 shows agarose gel-fractionated DNA fragments used for transfer on HyBond N+ nylon membrane according to Southern blotting procedure (I) and results of radioautography after hybridization of membranes with radioactively labeled probes. Lane 1, pBR322 DNA fragments after parallel digestion with FastDigest® FspI and with FastDigest® SfcI; lane 2, pBR322 DNA fragments resulting after parallel digestion with FastDigest® FspI and with FastDigest® SfcI and mixed with λ DNA fragments after cleavage with Eco91I; lane 3, λ DNA fragments after cleavage with Eco91I. (A) membrane was hybridized with probe which was generated by PCR using unmethylated SgeI-treated λ DNA; (B) membrane was hybridized with probe which was generated by PCR using SgeI-treated mixture of M.SssI-modified pBR322 DNA and unmethylated λ DNA; (C) membrane was hybridized with probe which was generated by PCR using SgeI-treated M.SssI-modified pBR322 DNA.

Hybridization results clearly show that all bands, identified during Southern hybridization experiment, correspond to DNA fragments originating exclusively from pBR322 (FIG. 16, part II, B&C, lanes 1 and 2). On the other hand, the presence of hybridization signals depends on the presence of M.SssI-modified DNA of pBR322 in SgeI cleavage reaction (FIG. 16, part II, B and C), but not on the presence of unmodified λ DNA (FIG. 16, part II, A and B). Based on these observations it may be concluded that DNA fragments amplified by PCR in the presence of radioactive label originate from M.SssI-modified and SgeI-cleaved DNA of pBR322 but not from unmodified phage λ DNA. Therefore, SgeI and related methylation-specific restriction endonucleases may be used for analysis or methylation pattern by hybridization approach.

REFERENCES

Roberts, R. J., and Halford, S. E. (1993) *Nucleases* (Linn, S. M., Lloyd, R. S., and Roberts, R. J., eds) pp. 35-88, Cold Spring Harbor Laboratory, Cold Spring Harbor, N.Y.

Raleigh, E. A., and Brooks, J. E. (1998) In *Bacterial Genomes* (De Bruijn, F. J., Lupski, J. R. and Weinstock, G. M., eds) pp. 78-92, Chapman&Hall, NY Wilson, G. G. (1991) *Nucleic Acid Res.,* 19, 2539-2566

Arber, W. (2000) *FEMS Microbiol. Rev.* 24, 1-7

Kobayashi, I (2001) *Nucleic Acid Res.* 29, 3742-3756

Naito, T., Kusano, K., and Kobayashi, I. (1995) Selfish behavior of restriction-modification systems. *Science* 267: 897-899

Messer, W., and Noyer-Weidner, M. (1988) *Cell,* 54, 735-737

Barras, F., and Marinus, M. G. (1989) *Trends Genet.* 5, 138-143

L. L. Christensen and J. Josephsen The Methyltransferase from the L1aDII Restriction-Modification System Influences the Level of Expression of Its Own Gene J. Bacteriol., Jan. 15, 2004; 186(2): 287-295

Beletskaya, Irina V., Zakharova, Marina V., Shlyapnikov, Michael G., Semenova, Lidiya M., Solonin, Alexander S. DNA methylation at the CfrBI site is involved in expression control in the CfrBI restriction-modification system. Nucl. Acids Res. 2000 28: 3817-3822

Ann Reisenauer, and Lucy Shapiro DNA methylation affects the cell cycle transcription of the CtrA global regulator in *Caulobacter* EMBO J. 2002 21: 4969-4977

Yogitha N. Srikhanta, Tina L. Maguire, Katryn J. Stacey, Sean M. Grimmond, and Michael P. Jennings The phasevarion: A genetic system controlling coordinated, random switching of expression of multiple genes PNAS 2005 102: 5547-5551

Roberts, D., Hoopes, B. C., McClure, W. R., and Kleckner, N. (1985) Cell 43, 117-130

Modrich, P. (1989) *J. Biol. Chem.* 264, 6579-6600

Roberts R J, Belfort M, Bestor T, Bhagwat A S, Bickle T A, Bitinaite J, Blumenthal R M, Degtyarev S Kh, Dryden D T, Dybvig K et al. A nomenclature for restriction enzymes, DNA methyltransferases, homing endonucleases and their genes. Nucleic Acids Res. 2003 31(7):1805-12

Raleigh, E. A. and Wilson, G. (1986) *Escherichia coli* K-12 restricts DNA containing 5-methylcytosine. Proc. Natl. Acad. Sci. USA, 83, 9070-9074

Stewart, F. J. and Raleigh, E. A. 1998 Biol Chem 379, 611-616

Geier G E, Modrich P. Recognition Sequence of the Dam Methylase of *E-Coli-*K12. *Clin Res.* 1979; 27: A604-A604

U.S. Pat. No. 5,789,166 "Circular site-directed mutagenesis" 1995

United States Patent Application 20060228786 "Polymerase-based protocols for the introduction of deletions and insertions"

Edelheit O, Hanukoglu A, Hanukoglu I. Simple and efficient site-directed mutagenesis using two single-primer reactions in parallel to generate mutants for protein structure-function studies. BMC Biotechnol. 2009 9:61

Liu H, Naismith J H. An efficient one-step site-directed deletion, insertion, single and multiple-site plasmid mutagenesis protocol. BMC Biotechnol. 2008 8:91

Li J, Li C, Xiao W, Yuan D, Wan G, Ma L. Site-directed mutagenesis by combination of homologous recombination and DpnI digestion of the plasmid template in *Escherichia coli*. Anal Biochem. 2008 373(2):389-91

Wei D, Li M, Zhang X, Xing L. An improvement of the site-directed mutagenesis method by combination of megaprimer, one-side PCR and DpnI treatment. Anal Biochem. 2004 331 (2):401-3

Bichet A, Bureik M, Lenz N, Bernhardt R. The "Bringer" strategy: a very fast and highly efficient method for construction of mutant libraries by error-prone polymerase chain reaction of ring-closed plasmids. Appl Biochem Biotechnol. 2004 117 (2):115-22

Li S, Wilkinson M F. Site-directed mutagenesis: a two-step method using PCR and DpnI. *Biotechniques.* 1997 23 (4): 588-90

Shareef M M, Dancea H C, Gross J L, Myers T T, Griggs W W, Ahmed M M, Sheldon D G. A noncommercial polymerase chain reaction-based method to approach one hundred percent recombinant clone selection efficiency. *Anal Biochem.* 2008 382 (1):75-6

Wood R J, Maynard-Smith M D, Robinson V L, Oyston P C, Titball R W, Roach P L. Kinetic Analysis of *Yersinia pestis* DNA Adenine Methyltransferase Activity Using a Hemimethylated Molecular Break Light Oligonucleotide PLoS One. 2007 2 (8):e801

Li J, Yan H, Wang K, Tan W, Zhou X. Hairpin fluorescence DNA probe for real-time monitoring of DNA methylation. Anal Chem. 2007 79 (3):1050-6

Vovis G F, Lacks S. Complementary action of restriction enzymes endo R-DpnI and Endo R-DpnII on bacteriophage fl DNA. *J Mol. Biol.* 1977; 115:525-538

Wood R J, Maynard-Smith M D, Robinson V L, Oyston P C, Titball R W, Roach P L. Kinetic analysis of *Yersinia pestis* DNA adenine methyltransferase activity using a hemimethylated molecular break light oligonucleotide. *PLoS One.* 2007 2 (8):e801 http://www.neb.com

Russian patent application RU 2270859 (C1)

http://www.sibenzyme.com/products/m2 type

Bird, A. (1992) The essentials of DNA methylation. Cell, 70, 5-8

Finnegan E. J. The role of DNA methylation in plant development. In: Russo V., et al., editors. *Epigenetic mechanisms of gene regulation.* Cold Spring Harbor Laboratory Press; Cold Spring Harbor, N.Y.: 1996. pp. 127-140

Jörg Tost, editor. *Methods in Molecular Biology.* Humana Press, vol. 507: DNA Methylation: Methods and Protocols, 2009

Clark S J, Harrison J, Paul C L, Frommer M. High sensitivity mapping of methylated cytosines Nucleic Acids Res. 1994 Aug. 11; 22 (15):2990-7

Lister, R. et al. Highly integrated single-base resolution maps of the epigenome in *Arabidopsis*. Cell 133, 523-536 (2008)

Cokus, S. J. et al. Shotgun bisulphite sequencing of the *Arabidopsis* genome reveals DNA methylation patterning. Nature 452, 215-219 (2008)

Lister R, Pelizzola M, Dowen R H, Hawkins R D, Hon G, Tonti-Filippini J, Nery J R, Lee L, Ye Z, Ngo Q M Edsall L, Antosiewicz-Bourget J, Stewart R, Ruotti V, Millar A H, Thomson J A, Ren B, Ecker J R. Human DNA methylomes at base resolution show widespread epigenomic differences. *Nature.* 2009 462 (7271):315-22

Grunau, C., Clark, S. J., Rosenthal, A. (2001) Bisulfite genomic sequencing: systematic investigation of critical experimental parameters. *Nucleic Acids Res* 29, e65

United States Patent Application 20060275806

United States Patent Application 20090004646

United States Patent Application 20050272065

United States Patent Application 20050158739

United States Patent Application 20050153316

Fazzari, M. J., Greally, J. M. (2004) Epigenomics: beyond CpG islands. *Nat Rev Genet.* 5, 446-455

Sambrook, 1989

Godon, J. J., Zumstein, E., Dabert, P., Habouzit, F., Moletta, R. 1997. Molecular Microbial Diversity of an Anaerobic Digestor as Determined by Small-Subunit rDNA Sequence Analysis. Appl. Environ. Microbiol. 63:2802-2813

Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. (2007) ClustalW and ClustalX version 2. Bioinformatics 2007 23(21): 2947-2948

Altschul S F, Gish W, Miller W, Myers E W, Lipman DJ (1990). "Basic local alignment search tool". *J Mol Biol* 215 (3): 403-410

R. N. Mishra et al., Biotechniques 33, 2002

Ochman H, Gerber A S, Hartl D L. Genetic applications of an inverse polymerase chain reaction. Genetics. 1988 November; 120 (3):621-3

Birnboim H C, Doly J. A rapid alkaline extraction procedure for screening recombinant plasmid DNA. Nucleic Acids Res. 1979 Nov. 24; 7 (6):1513-23

Messing et al., 1977, Proc. Natl. Acad. Sci. USA 74:3642-3646

Messing et al., 1981, Nucl. Acids Res. 9:309-321

SEQUENCES

SEQ ID NO: 1

R. SgeI (protein sequence):
Mtkwlrigqvlryaktkdpsneveggfpnfwhvtgtpganrallekginpigeldvqsvvrrpavlirsspwkagsdqtpwhd vfdlehghvryfgdhkhglakptgategnaallraferhrapsreqrvlaepllvfrsvtrgkspkghvefcgvglieraeri vqwgganretfvnyvydfamldlseegdqldwawiearrnveftaeqalkaaprswrawvegghatlpkvrrrvaqtryvkvk dqkptpgtaeskdldtiyhhfdgrkhdfeavastvaarilsfgasyrhgwltrrsgdggadfvgrldvgrglagtslvvlgqa kcvkpestisaegiarvvarlrrgwigvfvttgsfsdaaglemvedgypialvngrelardlrmmanehyhgdliaclddihq khgtgtviterrpeeille

SEQ ID NO: 2 sgeIR (gene sequence):
atgaccaaatggttgcggatcggtcaggtgcttcgatacgcgaagaccaaagacccatccaacgaagttgaaggcggcttccc gaacttttggcacgtaaccggactcccggcgctaatcgggcgctcttggagaagggatcaaccccattggtgagttggacg tccagagtgtggtgcgtcgaccagcggtgctcatcaggtccagtccttggaaggctgggagtgatcagacgccgtggcacgac gtgttcgaccttgaacatggacacgttcgctacttcggggaccataagcatggtttggcgaaacccaccggcgctaccgaggg caacgctgccctgcttcgggcattcgagcggcaccgtgcaccgtcaagagaacaacgtgtgttggcagaaccgttgctcgtat ttcggtccgtcacccgtggtaagagccctaaggggcatgtcgagttctgcggtgtgggcttgatcgaacgtgccgagcgcatc gttcagtggggcggggccaaccgagagacgttcgtcaactatgtgtatgacttcgccatgcttgatctctcggaagagggaga ccaactcgactgggcatggatcgaggcacggcgcaacgttgagttcacggcagagcaggcgttgaaggccgctccgcggtctt ggcgggcatgggttgaggtggtcacgcaaccttgccaaaggttcgacgacgtgtcgctcagacgcgtgtggtgaaggtgaag gaccagaagccaacgccgggcactgctgagtcgaaggatctcgacacgatctaccaccactttgacggtcgcaagcacgactt cgaggccgtcgcgtccacggtggccgctcgaatcctcagtttcggagcctcctaccgacatggctggctcactcgtcgttcgg gtgacggggcgccgacttcgttggccgactcgatgtcggccgaggactggcaggcacgagtcttgtggttctcggccaagcc aagtgcgtgaagccggagagcaccatcagtgccgagcagatcgcccgggttgtggctcgtctgcgtcgcggctggatcggggt gttcgtcacgaccggatccttctccgacgctgcccagcttgagatggtcgaggatcagtacccccatcgcgctggtcaacgggc gggaactagcccgtgatctacggatgatggccaacgagcactaccacggggacttgatcgcttgcctcgatgacattcaccag aagcatggacgggcacggtcataactgaacgtcggcccgaagagatcctgcttgagtag

SEQ ID NO: 3

Comparison with amino acid sequence from *Micromospora aurantiaca*:
```
SgeI      MTKWLRIGQVLRYAKTKDPSNEVEGGFPNFWHVTGTPGANRALLEKGINPIGELDVQSVV           60
EFA33149  ----MRMNAVLRYGRVAIDLP-IADGYPNLHYLSTGPIGTRVLLESGINPVRSIGAQGRQ           55
              :*:. ****.::      : .*:**: ::: * ..*.***.****. :..:.*.

SgeI      RRPAVLIRSSPWKAGSDQTPWHDVFDLEHGHVRYFGDHKHGLAKPTGATEGNAALLRAFE          120
EFA33149  RRPVIALRSSPWKAGGEDTPWHDVFDLDHGHVRYFGDHKVSTDGPLGSTTGNKALLEAWP          115
          ***.:  :********.::********.*********** .   *  *:.*  **.*.*:

SgeI      RHRAPSREQRVLAEPLLVFRSVTRGKSPKGHVEFCGVGLIERAERIVQWGGANRETFVNY          180
EFA33149  QHRGSTPETRAAAPPLLLFRSVSVGRALKGYIEFCGVAVLDRLEHVVQRDPSTGQSFANY          175
          :**..: * *.  * ***:****: :.  **::*****.::* *::**  . :.::*.**
```

```
SgeI      VYDFAMLDLSEEGDQLDWAWIEARRNVEFTAEQALKAAPRSWRAWVEGGHATLPKVRRRV    240
EFA33149  AFDLTVLSLAEEAEAIDWRWIDDRRDPGLSLQETHRHAPRSWRRWVEHGDPILPRLRRRV    235
          .:*.::::*.*:**.: :** **: **:   ::  :::  :  ****** ***  *..  ** :****

SgeI      AQTRVVKVKDQKPTPGTAESKDLDTIYHHFDGRKHDFEAVASTVAARILS-FGASYRHGW    299
EFA33149  ATSRVRSKSDQRPEAGSVEAQILRRIYEFYQGRQHRFELLAARVAARVFRGQGAVYHEGW    295
          * :**  . .**:* .:*:.*::  * **...::**.* ** *:: ****::    ** *:.**

SgeI      LTRRSGDGGADFVGRLDVGRGLAGTSLVVLGQAKCVKPESTISAEQIARVVARLRRGWIG    359
EFA33149  LTRGSGDRGVDFVGRLDVGSEDAITSLVVLGQAKCR-LDKSVSAEELARVVARLRRGWIG    354
          *** *** *.********* * *********** . .::.:***:**************

SgeI      VFVTTGSFSDAAQLEMVEDQYPIALVNGRELARDLRMMANEHYHGDLIACLDDIHQKHGT    419
EFA33149  AYVTTSDYSRNAQEEMMDDQYPIVLIDGRRLAEEVRRMASDSHGGNLNTFLSELAS--GY    412
          .:**  ..:*  ** **:*****.*::**.**:::  *:.. .:* : *.:: . *

SgeI      GTVITERRPEEILLE                                                 434
EFA33149  EEAVTSRRPEEILSL                                                 427
          .:*.*******
```

---

The invention claimed is:

1. A methylation-specific restriction endonuclease for a DNA duplex substrate, which endonuclease comprises SEQ ID NO: 1 or a variant thereof at least 90% identical to SEQ ID NO: 1.

2. A methylation-specific restriction endonuclease for a DNA duplex substrate, which endonuclease comprises SEQ ID NO: 1, and recognizes in a strand of the duplex a recognition sequence comprising a 5-methylcytosine, and cleaves each strand of the duplex at a fixed position outside the recognition sequence.

3. The restriction endonuclease according to claim 2, which cleaves the strands of the duplex at positions so as to produce a 5' overhang of 4 nucleotides.

4. The restriction endonuclease according to claim 2, wherein the recognition sequence is m5CNNG.

5. The restriction endonuclease according to claim 4, which is obtainable from *Streptomyces griseoflavus* strain RFL11.

6. A method for the site-specific cleavage of double-stranded DNA which contains 5-methylcytosine in one or both strands, which method comprises mixing a sample comprising the double-stranded DNA, a buffer, and a methylation-specific restriction endonuclease according to claim 2 to form a reaction mixture, and incubating the reaction mixture so as to digest the double-stranded DNA completely.

7. The method according to claim 6, wherein the sample further comprises target double-stranded DNA which is free of 5-methylcytosine, which target double-stranded DNA is undigested.

8. A method for determining in a test DNA sample the level of methylation of cytosine at the 5-position, which method comprises:
   (i) treating the test DNA sample with a restriction endonuclease according to claim 2 to cleave DNA containing 5-methylcytosine into reaction products;
   (ii) incubating the reaction products with a DNA polymerase in the presence of at least one labeled deoxynucleotide or analogue thereof capable of being incorporated into the reaction products by the DNA polymerase; and
   (iii) measuring the amount of incorporated label to indicate the level of methylation of cytosine at the 5 position.

9. The method according to claim 8, wherein the amount of incorporated label is measured to indicate the level of methylation of cytosine at the 5 position by comparison with the amount of label incorporated into a control DNA sample which is the same as the test sample (a) without treatment with the restriction endonuclease; and (b) which was pretreated with SssI methyltransferase to modify cytosines within CG dinucleotides.

10. The method according to claim 8, wherein the amount of incorporated label is measured to indicate the level of methylation of cytosine at the 5 position by comparison with the amount of label incorporated into a control DNA sample which is the same as the test sample (a) without treatment with the restriction endonuclease, (b) which was digested with a type II restriction endonuclease instead of the methylation-specific restriction endonuclease, or (c) which was digested with a type II restriction endonuclease simultaneously with the methylation-specific restriction endonuclease.

11. The method according to claim 8, wherein the at least one labeled deoxynucleotide or analogue thereof is a DNA synthesis terminator so that only one labeled deoxynucleotide is incorporated into the end of each reaction product.

12. The method according to claim 8, wherein the label comprises a radioactive label, a fluorescent label or a covalently-coupled chemical compound label.

13. A method for genome-wide analysis of individual 5-methylcytosines, which comprises:
   (i) treating a DNA sample with a restriction endonuclease according to claim 2 to cleave DNA containing 5-methylcytosine into reaction products,
   (ii) incubating the reaction products with a nucleic acid ligase in the presence of a synthetic nucleic acid of known sequence to generate ligated molecules comprising the synthetic nucleic acid and an individual reaction product;
   (iii) analyzing the sequence of individual ligated molecules using the nucleotide sequence information from the ligated synthetic nucleic acid; and
   (iv) identifying individual 5-methylcytosines which are (a) at the correct distance from the 5'-end of ligated synthetic nucleic acid, based on the cleavage behaviour of the methylation-specific restriction endonuclease and (b) which occur in the correct sequence context.

14. The method according to claim 13, wherein the reaction products are treated with phosphatase to remove 5'-phosphates.

15. The method according to claim 13, wherein the nucleic acid ligase is DNA ligase which catalyzes the formation of a phosphodiester bond between juxtaposed 5'-phosphate and 3'-hydroxyl termini of nucleic acids.

16. The method according to claim 13, wherein the synthetic nucleic acid is in a single-stranded form.

17. The method according to claim 16, wherein the synthetic nucleic acid has four unspecified bases (5'-NNNN) at the 5' end.

18. The method according to claim 13, wherein the synthetic nucleic acid is in a double-stranded linear form.

19. The method according to claim 13, wherein the synthetic nucleic acid is in a double-stranded hairpin form.

20. The method according to claim 13, wherein the synthetic nucleic acid comprises DNA or a mixture of deoxyribonucleotides with other nucleic acids.

21. The method according to claim 13, wherein the synthetic nucleic acid is modified by a covalently coupled fluorescent label or a covalently-coupled chemical compound label.

22. The method according to claim 13, wherein the ligated molecules are amplified.

23. The method according to claim 13, wherein the ligated molecules are treated with bisulfite before sequencing.

24. The method according to claim 23, wherein the ligated molecules are treated with bisulfite before amplification.

25. A method for whole genome analysis of DNA methylation patterns, the method comprising:
   (i) treating a DNA sample with at least one restriction endonuclease according to claim 2 to cleave DNA containing 5-methylcytosine into reaction products;
   (ii) incubating the reaction products with a nucleic acid ligase in the presence of a synthetic nucleic acid of known sequence to generate ligated molecules;
   (iii) amplifying the ligated molecules using the nucleotide sequence information from the ligated synthetic nucleic acid; and
   (iv) detecting the amplified products.

26. The method according to claim 25, wherein the reaction products are treated with phosphatase to remove 5'-phosphates.

27. The method according to claim 25, wherein the nucleic acid ligase is DNA ligase which catalyzes the formation of a phosphodiester bond between juxtaposed 5'-phosphate and 3'-hydroxyl termini of nucleic acids.

28. The method according to claim 25, wherein the synthetic nucleic acid is in a single-stranded form.

29. The method according to claim 28, wherein the synthetic nucleic acid has four unspecified bases (5'-NNNN) at the 5' end.

30. The method according to claim 25, wherein the synthetic nucleic acid is in a double-stranded linear form.

31. The method according to claim 25, wherein the synthetic nucleic acid is in a double-stranded hairpin form.

32. The method according to claim 25, wherein the synthetic nucleic acid comprises DNA or a mixture of deoxyribonucleotides with other nucleic acids.

33. The method according to claim 25, wherein the ligated molecules are amplified using polymerase chain reaction, isothermal amplification or transcription-mediated amplification.

34. The method according to claim 25, wherein the ligated molecules are treated with bisulfite before amplification.

35. The method according to claim 25, wherein the synthetic nucleic acid is modified by a covalently coupled fluorescent label or a covalently-coupled chemical compound label.

36. The method according to claim 8, wherein the DNA sample is from a single cell.

37. The method according to claim 13, wherein the DNA sample is from a single cell.

38. The method according to claim 25, wherein the DNA sample is from a single cell.

39. The restriction endonuclease according to claim 2, which cleaves the strand comprising the 5-methylcytosine at a position which is 12 nucleotides from the 5-methylcytosine in the 3' direction.

40. An isolated polypeptide comprising SEQ ID NO: 1 or a variant thereof at least 90% identical to SEQ ID NO: 1.

* * * * *